(12) United States Patent
MacDonald et al.

(10) Patent No.: US 11,017,352 B2
(45) Date of Patent: May 25, 2021

(54) MANAGEMENT OF PHARMACY KITS USING MULTIPLE ACCEPTANCE CRITERIA FOR PHARMACY KIT SEGMENTS

(71) Applicant: Kit Check, Inc., Washington, DC (US)

(72) Inventors: Kevin William MacDonald, Washington, DC (US); David Mario Pedra, Washington, DC (US); Timothy James Leo Kress-Spatz, Washington, DC (US); Christian Lee Doyle, Silver Spring, MD (US); Eric Brody, Reston, VA (US)

(73) Assignee: Kit Check, Inc., Alexandria, VA (US)

( * ) Notice: Subject to any disclaimer, the term of this patent is extended or adjusted under 35 U.S.C. 154(b) by 1130 days.

(21) Appl. No.: 15/269,371

(22) Filed: Sep. 19, 2016

(65) Prior Publication Data
US 2017/0132734 A1     May 11, 2017

Related U.S. Application Data

(63) Continuation of application No. 14/472,410, filed on Aug. 29, 2014, now Pat. No. 9,449,296, which is a
(Continued)

(51) Int. Cl.
*G06Q 10/08* (2012.01)
*G16H 20/10* (2018.01)
(Continued)

(52) U.S. Cl.
CPC ......... *G06Q 10/0875* (2013.01); *G16H 20/10* (2018.01); *G16H 40/20* (2018.01); *G16H 70/40* (2018.01)

(58) Field of Classification Search
CPC .... G06Q 50/22; G06Q 10/0875; G06Q 50/24; G16H 20/10; G16H 40/20; G16H 70/40
See application file for complete search history.

(56) References Cited

U.S. PATENT DOCUMENTS

| 4,884,827 A | 12/1989 | Kelley |
| 4,961,533 A | 10/1990 | Teller et al. |
| (Continued) |

FOREIGN PATENT DOCUMENTS

| CA | 2 722 328 | 10/2009 |
| CA | 2 790 220 | 6/2013 |
| (Continued) |

OTHER PUBLICATIONS

Baum, "How did RFID help University of MD Medical Center cut medication error rate?" Med City News, https://medcitynews.com/2013/12/rfid-help-university-md-medical-center-cut-medication-error-rate/?rf=1, Dec. 4, 2013, 2 Pages.
(Continued)

*Primary Examiner* — Eliza A Lam
(74) *Attorney, Agent, or Firm* — Knobbe, Martens, Olson & Bear, LLP

(57) ABSTRACT

A pharmacy kit is managed by defining multiple rules for determining whether a segment of a pharmacy kit is satisfactorily stocked, selecting at least one rule among the multiple rules according to a kit stocking contingency, an prompting a user to stock the segment of the pharmacy kit according to the selected at least one rule.

18 Claims, 36 Drawing Sheets

Related U.S. Application Data continuation-in-part of application No. 13/554,342, filed on Jul. 20, 2012, now Pat. No. 8,990,099.

(60) Provisional application No. 62/021,927, filed on Jul. 8, 2014, provisional application No. 61/514,231, filed on Aug. 2, 2011.

(51) Int. Cl.
  *G16H 40/20* (2018.01)
  *G16H 70/40* (2018.01)

(56) References Cited

U.S. PATENT DOCUMENTS

| | | |
|---|---|---|
| 5,713,485 A | 2/1998 | Liff et al. |
| 5,930,145 A | 7/1999 | Yuyama et al. |
| 5,963,134 A | 10/1999 | Bowers et al. |
| 5,986,662 A | 11/1999 | Argiro et al. |
| 6,112,502 A | 9/2000 | Frederick et al. |
| 6,249,299 B1 | 6/2001 | Tainer |
| 6,275,157 B1 | 8/2001 | Mays et al. |
| 6,294,999 B1 | 9/2001 | Yarin et al. |
| 6,330,351 B1 | 12/2001 | Yasunaga |
| 6,574,166 B2 | 6/2003 | Niemiec |
| 6,632,619 B1 | 10/2003 | Harrison et al. |
| 6,771,369 B2 | 8/2004 | Rzasa et al. |
| 6,825,864 B2 | 11/2004 | Botten et al. |
| 6,847,861 B2 | 1/2005 | Lunak et al. |
| 6,851,615 B2 | 2/2005 | Jones |
| 6,861,954 B2 | 3/2005 | Levin |
| 6,877,658 B2 | 4/2005 | Raistrick et al. |
| 6,879,876 B2 | 4/2005 | O'Dougherty et al. |
| 6,900,021 B1 | 5/2005 | Harrison et al. |
| 6,933,849 B2 | 8/2005 | Sawyer |
| 6,935,560 B2 | 8/2005 | Andreasson et al. |
| 6,952,681 B2 | 10/2005 | McQuade et al. |
| 6,985,870 B2 | 1/2006 | Martucci et al. |
| 6,992,574 B2 | 1/2006 | Aupperle et al. |
| 6,994,249 B2 | 2/2006 | Peterka et al. |
| 7,036,729 B2 | 5/2006 | Chung |
| 7,061,831 B2 | 6/2006 | De La Huerga |
| 7,111,780 B2 | 9/2006 | Broussard et al. |
| 7,116,343 B2 | 10/2006 | Botten et al. |
| 7,118,029 B2 | 10/2006 | Nycz et al. |
| 7,140,542 B2 | 11/2006 | Andreasson et al. |
| 7,146,247 B2 | 12/2006 | Kirsch et al. |
| 7,151,456 B2 | 12/2006 | Godfrey |
| 7,158,030 B2 | 1/2007 | Chung |
| 7,165,077 B2 | 1/2007 | Kalies |
| 7,175,081 B2 | 2/2007 | Andreasson et al. |
| 7,177,721 B2 | 2/2007 | Kirsch et al. |
| 7,178,729 B2 | 2/2007 | Shaffer et al. |
| 7,182,256 B2 | 2/2007 | Andreasson et al. |
| 7,212,100 B2 | 5/2007 | Terenna |
| 7,212,127 B2 | 5/2007 | Jacober et al. |
| 7,227,469 B2 | 6/2007 | Varner et al. |
| 7,232,066 B2 | 6/2007 | Andreasson et al. |
| 7,253,736 B2 | 8/2007 | Tethrake et al. |
| 7,256,699 B2 | 8/2007 | Tethrake et al. |
| 7,263,501 B2 | 8/2007 | Tirinato et al. |
| 7,264,323 B2 | 9/2007 | Tainer et al. |
| 7,268,684 B2 | 9/2007 | Tethrake et al. |
| 7,275,645 B2 | 10/2007 | Mallett et al. |
| 7,299,981 B2 | 11/2007 | Hickle et al. |
| 7,316,231 B2 | 1/2008 | Hickle |
| 7,317,393 B2 | 1/2008 | Maloney |
| 7,318,529 B2 | 1/2008 | Mallett et al. |
| 7,339,550 B2 | 3/2008 | Hayama et al. |
| 7,341,147 B2 | 3/2008 | Mallett et al. |
| 7,348,884 B2 | 3/2008 | Higham |
| 7,354,884 B2 | 4/2008 | Hada et al. |
| 7,362,228 B2 | 4/2008 | Nycz et al. |
| 7,375,737 B2 | 5/2008 | Botten et al. |
| 7,394,383 B2 | 7/2008 | Hager et al. |
| 7,440,818 B2 | 10/2008 | Handfield et al. |
| 7,446,747 B2 | 11/2008 | Youngblood et al. |
| 7,454,880 B1 | 11/2008 | Austin et al. |
| 7,486,188 B2 | 2/2009 | Van Alstyne |
| 7,492,257 B2 | 2/2009 | Tethrake et al. |
| 7,492,261 B2 | 2/2009 | Cambre et al. |
| 7,504,954 B2 | 3/2009 | Spaeder |
| 7,518,502 B2 | 4/2009 | Austin et al. |
| 7,518,516 B2 | 4/2009 | Azevedo et al. |
| 7,551,089 B2 | 6/2009 | Sawyer |
| 7,559,483 B2 | 7/2009 | Hickle et al. |
| 7,564,364 B2 | 7/2009 | Zweig |
| 7,630,791 B2 | 12/2009 | Nguyen et al. |
| 7,639,136 B1 | 12/2009 | Wass et al. |
| 7,644,016 B2 | 1/2010 | Nycz et al. |
| 7,672,872 B2 | 3/2010 | Shanton |
| 7,706,915 B2 | 4/2010 | Mohapatra et al. |
| 7,706,916 B2 | 4/2010 | Hilton |
| 7,712,670 B2 | 5/2010 | Sauerwein, Jr. et al. |
| 7,715,277 B2 | 5/2010 | De La Huerga |
| 7,729,597 B2 | 6/2010 | Wright et al. |
| 7,734,157 B2 | 6/2010 | Wright et al. |
| 7,737,858 B2 | 6/2010 | Matityaho |
| 7,747,477 B1 | 6/2010 | Louie et al. |
| 7,752,085 B2 | 7/2010 | Monroe |
| 7,772,964 B2 | 8/2010 | Tethrake et al. |
| 7,775,056 B2 | 8/2010 | Lowenstein |
| 7,783,163 B2 | 8/2010 | Wright et al. |
| 7,783,174 B2 | 8/2010 | Wright et al. |
| 7,801,422 B2 | 9/2010 | Wright et al. |
| 7,815,117 B2 | 10/2010 | Tuschel et al. |
| 7,834,765 B2 | 11/2010 | Sawyer |
| 7,834,766 B2 | 11/2010 | Sawyer |
| 7,837,093 B1 | 11/2010 | Leu et al. |
| 7,837,107 B1 | 11/2010 | Leu et al. |
| 7,858,841 B2 | 12/2010 | Krautkramer et al. |
| 7,860,730 B1 | 12/2010 | Goodall et al. |
| 7,868,754 B2 | 1/2011 | Salvat, Jr. |
| 7,893,876 B2 | 2/2011 | Brown et al. |
| 7,908,030 B2 | 3/2011 | Handfield et al. |
| 7,918,830 B2 | 4/2011 | Langan et al. |
| 7,928,844 B2 | 4/2011 | Mackenzie et al. |
| 7,933,033 B2 | 4/2011 | Ohishi et al. |
| 7,976,508 B2 | 7/2011 | Hoag |
| 7,985,711 B2 | 7/2011 | Tohmatsu et al. |
| 7,990,272 B2 | 8/2011 | Wass et al. |
| 7,996,286 B2 | 8/2011 | Kreiner et al. |
| 8,002,174 B2 | 8/2011 | Coyne, III et al. |
| 8,006,903 B2 | 8/2011 | Braun et al. |
| 8,009,913 B2 | 8/2011 | Greyshock |
| 8,031,347 B2 | 10/2011 | Edwards et al. |
| 8,042,738 B2 | 10/2011 | Cloix |
| 8,049,627 B1 | 11/2011 | Addante |
| 8,063,925 B2 | 11/2011 | Tainer et al. |
| 8,065,858 B2 | 11/2011 | Leu et al. |
| 8,072,635 B2 | 12/2011 | Roberts et al. |
| 8,077,041 B2 | 12/2011 | Stern et al. |
| 8,082,192 B2 | 12/2011 | Nycz et al. |
| 8,099,339 B1 | 1/2012 | Pinsonneault et al. |
| 8,108,068 B1 | 1/2012 | Boucher et al. |
| 8,111,159 B2 | 2/2012 | Andreasson et al. |
| 8,112,175 B2 | 2/2012 | Handfield et al. |
| 8,131,397 B2 | 3/2012 | Vahlberg et al. |
| 8,154,390 B2 | 4/2012 | Heath et al. |
| 8,174,392 B1 | 5/2012 | Sagbhini et al. |
| 8,186,587 B2 | 5/2012 | Zmood et al. |
| 8,212,677 B2 | 7/2012 | Ferguson |
| 8,219,413 B2 | 7/2012 | Martinez et al. |
| 8,224,483 B1 | 7/2012 | Ansari et al. |
| 8,231,749 B2 | 7/2012 | Dent et al. |
| 8,258,961 B2 | 9/2012 | Phillips et al. |
| 8,261,939 B2 | 9/2012 | Knoth |
| 8,271,128 B1 | 9/2012 | Schultz |
| 8,279,069 B2 | 10/2012 | Sawyer |
| 8,283,287 B2 | 10/2012 | Aihara et al. |
| 8,284,059 B2 | 10/2012 | Ross |
| 8,285,083 B2 | 10/2012 | Canessa et al. |
| 8,285,607 B2 | 10/2012 | Danilewitz |
| 8,286,222 B2 | 10/2012 | Silverbrook et al. |
| 8,292,173 B2 | 10/2012 | Yturralde et al. |

(56) References Cited

U.S. PATENT DOCUMENTS

| | | |
|---|---|---|
| 8,292,186 B2 | 10/2012 | Deloche et al. |
| 8,296,950 B2 | 10/2012 | Colbrunn et al. |
| 8,313,024 B2 | 11/2012 | Marino |
| 8,319,607 B2 | 11/2012 | Grimlund et al. |
| 8,328,082 B1 | 12/2012 | Bochenko et al. |
| 8,339,649 B2 | 12/2012 | Ohishi et al. |
| 8,341,041 B2 | 12/2012 | Hull |
| 8,346,632 B2 | 1/2013 | Saghbini |
| 8,355,753 B2 | 1/2013 | Bochenko et al. |
| 8,355,962 B2 | 1/2013 | Delaney et al. |
| 8,359,338 B2 | 1/2013 | Butterfield et al. |
| 8,371,448 B1 | 2/2013 | Reaux |
| 8,376,228 B2 * | 2/2013 | DeVet .................. G06Q 50/22 235/383 |
| 8,384,545 B2 | 2/2013 | Hussain et al. |
| 8,385,972 B2 | 2/2013 | Bochenko et al. |
| 8,386,070 B2 | 2/2013 | Eliuk et al. |
| 8,394,053 B2 | 3/2013 | Bochenko et al. |
| 8,403,212 B2 | 3/2013 | van Esch |
| 8,403,224 B2 | 3/2013 | Fedorko et al. |
| 8,405,508 B2 | 3/2013 | Burke |
| 8,438,067 B2 | 5/2013 | Omura et al. |
| 8,461,076 B2 | 6/2013 | Okada et al. |
| 8,483,550 B2 | 7/2013 | Wright et al. |
| 8,509,604 B2 | 8/2013 | Wright et al. |
| 8,515,251 B2 | 8/2013 | Wright et al. |
| 8,519,849 B2 * | 8/2013 | Ross-Messemer .......................... G02B 27/017 340/572.1 |
| 8,530,379 B2 | 9/2013 | Shimizu et al. |
| 8,564,416 B2 | 10/2013 | Steven et al. |
| 8,565,552 B2 | 10/2013 | Sommer et al. |
| 8,582,171 B2 | 11/2013 | Srnka et al. |
| 8,589,271 B2 | 11/2013 | Evans |
| 8,593,278 B2 | 11/2013 | Churbock et al. |
| 8,593,678 B2 | 11/2013 | Ohishi et al. |
| D694,817 S | 12/2013 | Adam et al. |
| 8,606,596 B1 | 12/2013 | Bochenko et al. |
| 8,636,202 B2 | 1/2014 | Keefe et al. |
| 8,639,525 B2 | 1/2014 | Levine et al. |
| 8,686,859 B2 | 4/2014 | Hussain et al. |
| 8,699,054 B2 | 4/2014 | Edwards et al. |
| 8,702,674 B2 | 4/2014 | Bochenko |
| 8,723,674 B2 | 5/2014 | Conley et al. |
| 8,749,356 B2 | 6/2014 | Hussain et al. |
| 8,755,056 B2 | 6/2014 | Edwards et al. |
| 8,825,680 B2 | 9/2014 | Burke et al. |
| 8,838,215 B2 | 9/2014 | John et al. |
| 8,868,616 B1 | 10/2014 | Otto et al. |
| 8,893,970 B2 | 11/2014 | Keefe et al. |
| 8,922,435 B2 | 12/2014 | Fontecchio et al. |
| 8,935,280 B2 | 1/2015 | Bauman et al. |
| 8,945,066 B2 | 2/2015 | Bochenko et al. |
| 8,948,478 B2 | 2/2015 | Keefe et al. |
| 8,985,388 B2 | 3/2015 | Ratnakar |
| 8,990,099 B2 | 3/2015 | MacDonald et al. |
| 9,037,479 B1 | 5/2015 | MacDonald et al. |
| 9,058,412 B2 | 6/2015 | MacDonald et al. |
| 9,058,413 B2 | 6/2015 | MacDonald et al. |
| 9,058,435 B2 | 6/2015 | Keefe et al. |
| 9,171,280 B2 | 10/2015 | Gitchell et al. |
| 9,189,769 B2 | 11/2015 | Caputo et al. |
| 9,367,665 B2 | 6/2016 | MacDonald et al. |
| 9,449,296 B2 | 9/2016 | MacDonald et al. |
| 9,539,374 B2 | 1/2017 | Halpern |
| 9,582,644 B2 | 2/2017 | Gitchell et al. |
| 9,734,294 B2 | 8/2017 | MacDonald et al. |
| 9,805,169 B2 | 10/2017 | MacDonald et al. |
| 10,083,766 B2 | 9/2018 | Gitchell et al. |
| 10,210,954 B2 * | 2/2019 | Caputo ................ G06Q 10/087 |
| 10,600,513 B2 | 3/2020 | Gitchell et al. |
| 10,609,845 B2 | 3/2020 | Elizondo, II |
| 9,058,413 C1 | 4/2020 | MacDonald et al. |
| 10,621,394 B2 | 4/2020 | Hussain et al. |
| 10,643,743 B2 | 5/2020 | Caputo et al. |
| 10,658,077 B2 | 5/2020 | Hussain et al. |
| 10,658,078 B2 | 5/2020 | Caputo et al. |
| 10,664,740 B2 | 5/2020 | Elizondo, II |
| 2002/0026330 A1 | 2/2002 | Klein |
| 2002/0049650 A1 | 4/2002 | Reff |
| 2002/0087360 A1 | 7/2002 | Pettit |
| 2002/0087362 A1 | 7/2002 | Cobb et al. |
| 2002/0087554 A1 | 7/2002 | Seelinger |
| 2003/0055685 A1 | 3/2003 | Cobb et al. |
| 2003/0074223 A1 | 4/2003 | Hickle et al. |
| 2003/0102970 A1 | 6/2003 | Creel et al. |
| 2003/0160698 A1 | 8/2003 | Andreasson et al. |
| 2003/0216974 A1 | 11/2003 | Browne |
| 2004/0008123 A1 | 1/2004 | Carrender et al. |
| 2004/0032330 A1 | 2/2004 | Hoffman |
| 2004/0051368 A1 | 3/2004 | Caputo et al. |
| 2004/0057609 A1 | 3/2004 | Weinberg |
| 2004/0081669 A1 | 4/2004 | Greeven et al. |
| 2004/0158507 A1 | 8/2004 | Meek et al. |
| 2004/0178071 A1 | 9/2004 | Harrison et al. |
| 2004/0215486 A1 | 10/2004 | Braverman |
| 2004/0225528 A1 | 11/2004 | Brock |
| 2005/0014849 A1 | 1/2005 | Pettit et al. |
| 2005/0060171 A1 | 3/2005 | Molnar |
| 2005/0062603 A1 | 3/2005 | Fuerst et al. |
| 2005/0108044 A1 | 5/2005 | Koster |
| 2005/0125097 A1 | 6/2005 | Chudy et al. |
| 2005/0127176 A1 | 6/2005 | Dickinson |
| 2005/0149378 A1 | 7/2005 | Cyr et al. |
| 2005/0149414 A1 | 7/2005 | Schrodt et al. |
| 2005/0184151 A1 | 8/2005 | DiMaggio et al. |
| 2005/0283259 A1 | 12/2005 | Wolpow |
| 2005/0285732 A1 | 12/2005 | Sengupta et al. |
| 2005/0285746 A1 | 12/2005 | Sengupta et al. |
| 2006/0006999 A1 | 1/2006 | Walczyk et al. |
| 2006/0043177 A1 | 3/2006 | Nycz et al. |
| 2006/0043179 A1 | 3/2006 | Nycz et al. |
| 2006/0065726 A1 | 3/2006 | Andreasson et al. |
| 2006/0109105 A1 | 5/2006 | Varner et al. |
| 2006/0132311 A1 | 6/2006 | Kruest et al. |
| 2006/0145871 A1 | 7/2006 | Donati et al. |
| 2006/0152338 A1 | 7/2006 | Hsu |
| 2006/0152364 A1 | 7/2006 | Walton |
| 2006/0152367 A1 | 7/2006 | Narayanaswamy |
| 2006/0208886 A1 | 9/2006 | Beamer |
| 2006/0267731 A1 | 11/2006 | Chen |
| 2007/0001809 A1 | 1/2007 | Kodukula et al. |
| 2007/0008399 A1 | 1/2007 | Botten et al. |
| 2007/0023512 A1 | 2/2007 | Miller et al. |
| 2007/0023513 A1 | 2/2007 | Andreasson et al. |
| 2007/0074722 A1 | 4/2007 | Giroux et al. |
| 2007/0114279 A1 | 5/2007 | Lessing et al. |
| 2007/0150382 A1 | 6/2007 | Danilewitz |
| 2007/0187475 A1 | 8/2007 | MacLeod |
| 2007/0188306 A1 | 8/2007 | Tethrake et al. |
| 2007/0200702 A1 | 8/2007 | Chung |
| 2007/0213659 A1 | 9/2007 | Trovato et al. |
| 2007/0213684 A1 | 9/2007 | Hickle et al. |
| 2007/0229268 A1 | 10/2007 | Swan et al. |
| 2007/0272746 A1 | 11/2007 | Ortiz et al. |
| 2008/0004908 A1 * | 1/2008 | Oh ........................ G06Q 50/22 705/2 |
| 2008/0012687 A1 | 1/2008 | Rubinstein |
| 2008/0045930 A1 | 2/2008 | Makin et al. |
| 2008/0046295 A1 | 2/2008 | Albrecht |
| 2008/0094214 A1 | 4/2008 | Azevedo et al. |
| 2008/0122878 A1 | 5/2008 | Keefe et al. |
| 2008/0128482 A1 | 6/2008 | Chen et al. |
| 2008/0129496 A1 | 6/2008 | Koblasz |
| 2008/0150722 A1 | 6/2008 | Jackson |
| 2008/0157967 A1 | 7/2008 | Jones et al. |
| 2008/0172253 A1 | 7/2008 | Chung et al. |
| 2008/0184719 A1 | 8/2008 | Lowenstein |
| 2008/0191013 A1 | 8/2008 | Liberatore |
| 2008/0218307 A1 | 9/2008 | Schoettle |
| 2008/0228160 A1 | 9/2008 | Harrison |
| 2008/0231456 A1 | 9/2008 | Matityaho |
| 2008/0243088 A1 | 10/2008 | Evans |
| 2008/0270178 A1 | 10/2008 | McRae et al. |

(56) References Cited

U.S. PATENT DOCUMENTS

| | | |
|---|---|---|
| 2008/0296373 A1 | 12/2008 | Smood et al. |
| 2008/0297356 A1 | 12/2008 | Oberle |
| 2008/0306772 A1 | 12/2008 | Shahrokh |
| 2008/0316045 A1* | 12/2008 | Sriharto .............. G06Q 50/22 340/10.1 |
| 2009/0002173 A1 | 1/2009 | Bergsten et al. |
| 2009/0020442 A1 | 1/2009 | Dietrich et al. |
| 2009/0058653 A1 | 3/2009 | Geissler et al. |
| 2009/0144087 A1 | 6/2009 | Kelsch et al. |
| 2009/0153290 A1 | 6/2009 | Bierach |
| 2009/0164042 A1 | 6/2009 | Handfield et al. |
| 2009/0194987 A1 | 8/2009 | Christie et al. |
| 2009/0224891 A1 | 9/2009 | Vishik et al. |
| 2009/0231138 A1 | 9/2009 | Cheung et al. |
| 2009/0267740 A1 | 10/2009 | Pizzuto et al. |
| 2009/0267772 A1 | 10/2009 | Dehnadi |
| 2009/0277815 A1 | 11/2009 | Kohl |
| 2009/0294521 A1 | 12/2009 | De La Huerga |
| 2010/0022953 A1 | 1/2010 | Bochenko et al. |
| 2010/0022987 A1 | 1/2010 | Bochenko |
| 2010/0036310 A1 | 2/2010 | Hillman |
| 2010/0036678 A1 | 2/2010 | Bray |
| 2010/0036755 A1 | 2/2010 | Saghbini |
| 2010/0042439 A1 | 2/2010 | Martinez et al. |
| 2010/0079337 A1 | 4/2010 | Hsu et al. |
| 2010/0098425 A1 | 4/2010 | Kewitsch |
| 2010/0108761 A1 | 5/2010 | Nycz et al. |
| 2010/0185458 A1 | 7/2010 | Calderwood et al. |
| 2010/0204659 A1 | 8/2010 | Bochenko |
| 2010/0217621 A1 | 8/2010 | Schoenberg et al. |
| 2010/0219097 A1 | 9/2010 | Ramasubramanian et al. |
| 2010/0238039 A1 | 9/2010 | Tethrake et al. |
| 2010/0268548 A1 | 10/2010 | Garrett et al. |
| 2010/0275625 A1 | 11/2010 | Lowenstein |
| 2010/0299158 A1 | 11/2010 | Siegel |
| 2010/0328474 A1 | 12/2010 | Hsieh |
| 2010/0332246 A1 | 12/2010 | Fedorko et al. |
| 2011/0006879 A1 | 1/2011 | Bartos |
| 2011/0063091 A1 | 3/2011 | Kang |
| 2011/0068922 A1 | 3/2011 | Ross |
| 2011/0112682 A1 | 5/2011 | Matsukawa et al. |
| 2011/0115612 A1 | 5/2011 | Kulinets et al. |
| 2011/0125315 A1 | 5/2011 | Handfield et al. |
| 2011/0131056 A1 | 6/2011 | Chudy et al. |
| 2011/0139871 A1 | 6/2011 | Yturralde et al. |
| 2011/0161112 A1 | 6/2011 | Keefe et al. |
| 2011/0163871 A1 | 7/2011 | Einav et al. |
| 2011/0166878 A1 | 7/2011 | Louie et al. |
| 2011/0184751 A1 | 7/2011 | Holmes |
| 2011/0187549 A1 | 8/2011 | Balasing |
| 2011/0225100 A1 | 9/2011 | Sangal et al. |
| 2011/0227722 A1 | 9/2011 | Salvat, Jr. |
| 2011/0240729 A1 | 10/2011 | Schuck |
| 2011/0257991 A1 | 10/2011 | Shukla |
| 2011/0270441 A1 | 11/2011 | Handfield et al. |
| 2011/0291809 A1 | 12/2011 | Niemiec et al. |
| 2011/0301446 A1 | 12/2011 | Kamen |
| 2011/0313395 A1 | 12/2011 | Krulevitch et al. |
| 2012/0037266 A1 | 2/2012 | Bochenko |
| 2012/0041778 A1 | 2/2012 | Kraft |
| 2012/0044054 A1* | 2/2012 | Hussain .............. G06F 19/00 340/10.1 |
| 2012/0061463 A1 | 3/2012 | Burke |
| 2012/0089411 A1 | 4/2012 | Srnka et al. |
| 2012/0089418 A1 | 4/2012 | Kamath et al. |
| 2012/0116798 A1 | 5/2012 | Heath et al. |
| 2012/0125994 A1 | 5/2012 | Heath et al. |
| 2012/0130534 A1 | 5/2012 | Wurm |
| 2012/0173673 A1 | 7/2012 | Becker et al. |
| 2012/0179132 A1 | 7/2012 | Valk et al. |
| 2012/0185951 A1 | 7/2012 | Bauman et al. |
| 2012/0209619 A1 | 8/2012 | Knotts et al. |
| 2012/0240067 A1 | 9/2012 | Bauman et al. |
| 2012/0273087 A1 | 11/2012 | Einy et al. |
| 2012/0278096 A1 | 11/2012 | Holness |
| 2012/0278228 A1 | 11/2012 | Rubinstein |
| 2012/0323208 A1 | 12/2012 | Bochenko et al. |
| 2012/0325330 A1 | 12/2012 | Prince et al. |
| 2013/0018356 A1 | 1/2013 | Prince et al. |
| 2013/0038452 A1 | 2/2013 | Sawyer |
| 2013/0041784 A1 | 2/2013 | Danilewitz |
| 2013/0092727 A1 | 4/2013 | Edwards et al. |
| 2013/0105568 A1 | 5/2013 | Jablonski et al. |
| 2013/0151005 A1 | 6/2013 | Gerold et al. |
| 2013/0191149 A1 | 7/2013 | Kolberg et al. |
| 2013/0221082 A1 | 8/2013 | Botten |
| 2013/0225945 A1 | 8/2013 | Prince et al. |
| 2014/0060729 A1 | 3/2014 | Srnka et al. |
| 2014/0066880 A1 | 3/2014 | Prince et al. |
| 2014/0117081 A1 | 5/2014 | Jablonski et al. |
| 2014/0136229 A1 | 5/2014 | Levine et al. |
| 2014/0142975 A1 | 5/2014 | Keefe et al. |
| 2014/0184390 A1 | 7/2014 | Elizondo, II |
| 2014/0184391 A1 | 7/2014 | Elizondo, II |
| 2014/0197954 A1 | 7/2014 | Caputo et al. |
| 2014/0210596 A1 | 7/2014 | Hussain et al. |
| 2014/0262919 A1 | 9/2014 | Hussain et al. |
| 2014/0263614 A1 | 9/2014 | Keefe et al. |
| 2014/0276213 A1 | 9/2014 | Bochenko |
| 2014/0282197 A1 | 9/2014 | Keefe et al. |
| 2014/0291397 A1 | 10/2014 | Caputo et al. |
| 2014/0367080 A1 | 12/2014 | Hussain et al. |
| 2015/0058182 A1 | 2/2015 | Kress-Spatz et al. |
| 2015/0235005 A1 | 8/2015 | MacDonald et al. |
| 2015/0339622 A1 | 11/2015 | MacDonald et al. |
| 2016/0132649 A1 | 5/2016 | Gitchell et al. |
| 2017/0212993 A1 | 7/2017 | Gitchell et al. |
| 2018/0039758 A1 | 2/2018 | MacDonald et al. |
| 2019/0088354 A1 | 3/2019 | Yanowitz et al. |
| 2019/0272396 A1 | 9/2019 | Clouser et al. |
| 2020/0013494 A1 | 1/2020 | Caputo et al. |
| 2020/0167534 A1 | 5/2020 | Elizondo, II |
| 2020/0357509 A1 | 11/2020 | Gitchell et al. |

FOREIGN PATENT DOCUMENTS

| | | |
|---|---|---|
| CN | 102791310 B | 12/2014 |
| EP | 2 496 283 | 9/2012 |
| IN | 2012/04914 P4 | 10/2013 |
| WO | WO 02/095675 | 11/2002 |
| WO | WO 03/071943 | 9/2003 |
| WO | WO 2006/026246 | 3/2006 |
| WO | WO 2006/135830 | 12/2006 |
| WO | WO 2010/074781 | 7/2010 |
| WO | WO 2011/056888 | 9/2011 |
| WO | WO 2011/115676 | 9/2011 |
| WO | WO 2011/150013 | 12/2011 |
| WO | WO 2013/082423 | 6/2013 |
| WO | WO 2013/116873 | 8/2013 |
| WO | WO 2013/134256 | 9/2013 |
| WO | WO 2014/159928 | 10/2014 |
| WO | WO 2014/189834 | 11/2014 |
| WO | WO 2015/026387 | 2/2015 |

OTHER PUBLICATIONS

Brown, Dennis E., "RFID Implementation", McGraw-Hill Communications, 2007, Ch. 3 & 7 (portions), pp. 62-65, 81, 92-96, 106-113, 188-193 & 429.

Garza, Anyssa, "The Future of Pharmacy Medication Kit Storage", Pharmacy Times, https://www.pharmacytimes.com/contributor/anyssa-garza/2014/12/the-future-of-pharmacy-medication-kit-storage, Dec. 12, 2014, 2 Pages.

Glover et al., "RFID Essentials", O'Reilly Media, 2006, pp. 2, 14, 24, 31, 33, 107-110, 113-114, 117, 137-143, 162-169, 178-179.

Hawkins-Simons, "RFID Streamlines Refilling of Drug Trays", Pharmacy Technology Report, https://www.pharmacypracticenews.com/Pharmacy-Technology-Report/Article/03-14/RFID-Streamlines-Refilling-of-Drug-Trays/26159, Mar. 21, 2014, 9 Pages.

Kinsella, Bret, "Premier, Inc. Identifies Kit Check as 'Technology Breakthrough Product'—Awards exclusive agreement for phar-

(56) References Cited

OTHER PUBLICATIONS macy kit medication tracking solution", Press Release, https://kitcheck.com/2014/04/premier-inc-identifies-kit-check-technology-breakthrough-product-awards-exclusive-agreement-pharmacy-kit-medication-tracking-solution/, Apr. 2, 2014, 5 Pages.
KitCheck,"PharMEDium Prefilled Syringes with Kit Check: ASHP Symposium Summary", Jun. 2016, https://kitcheck.com/wp-content/uploads/2016/06/pharmedium-prefilled-syringes-with-kit-check-download.pdf in 9 pages.
KitCheck,"St. Rita's Medical Center: 75% First-year ROI, Less Frustration", Case Study, 2016, https://kitcheck.com/learn-more/case-study/st-ritas-medical-center/ in 2 pages.
"Medication Tray Management" Pharmacy Purchasing & Products, Feb. 2018, pp. 18 & 20.
"Medication Tray Management" Pharmacy Purchasing & Products, Presentation, Nov. 2018, pp. 76 & 78.
"Medication Tray Management" Pharmacy Purchasing & Products, State of Pharmacy Automation, Aug. 2016, pp. 42 & 45.
"Medication Tray Management" Pharmacy Purchasing & Products, State of Pharmacy Automation, Aug. 2019, pp. 34-35.
"ODIN Innovation Lab: EasyTunnel RFID", as posted Jul. 13, 2009, archived via archive.org https://web.archive.org/web/20200316173502/https://www.youtube.com/watch?v=0rQhT4sIQnw, 1 page.
"ODIN RFID HQ Tour 2009", as posted Mar. 19, 2009, archived via archive.org https://web.archive.org/web/20200316180429/https://www.youtube.com/watch?v=4Y4XIID0B_Y, 1 page.
Summerfield, et al. "Evaluation of Medication Kit Processing Time Using Radio Frequency Identification (RFID) Technology", Innovations in Pharmacy, 2015, vol. 6, No. 2, Article 199, 7 Pages.
Swedberg, Claire, "North Carolina Hospital Identifies Recalled Drugs Via RFID", RFID Journal, http://www.rfidjournal.com/articles/view?10913, Aug. 14, 2013, 4 Pages.
Swedberg, Claire, "Zimmer Ohio to Use RFID to Manage Orthopedic Products", RFID Journal, May 12, 2010, pp. 3. https://www.rfidjournal.com/articles/pdf?7588.
"UPM Raflatac UHF EPC Gen2 RFID in ODIN Solution at Johnson-Johnson DePuyIn-Q-Tel", as posted Jun. 10, 2009, archived via archive.org https://web.archive.org/web/20200316174347/https://www.youtube.com/watch?v=JWGyR8BgfI8 , 1 page.
"Vizient, Inc. Awards Kit Check Contract for Pharmacy Kit Medication Inventory Tracking and Replenishment", Press Release, http://www.prweb.com/releases/2016/09/prweb13691526.htm, Sep. 19, 2016, 3 Pages.
Plaintiff Kit Check, Inc.'s Motion to Strike Insufficient Defenses, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jan. 19, 2018, 8 pages.
Defendant's Memorandum in Opposition to Plaintiff Kit Check, Inc.'s Mtion to Strike Insufficient Defenses, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Feb. 9, 2018, 6 pages.
Plaintiff's Answer to Defendant's First Amended Counterclaims, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Feb. 21, 2018, 14 pages.
Plaintiff Kit Check, Inc.'s Reply in Support of its Motion to Strike Insufficient Defenses, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Feb. 21, 2018, 6 pages.
Defendant Health Care Logistics, Inc.'s Motion for Judgment on the Pleadings Pursuant to Fed. R. Civ. P. 12(C), *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), May 25, 2018, 31 pages.
Exhibit A; U.S. Pat. No. 8,990,099, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), May 25, 2018, 12 pages.
Opinion & Order, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jun. 13, 2018, 9 pages.
Plaintiff Kit Check, Inc.'s Memorandum in Opposition to Defendant Health Care Logistics, Inc.'s Motion for Judgment on the Pleadings, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jun. 29, 2018, 35 pages.
Exhibit 1; Non-Final Office Action for U.S. Pat. No. 8,990,099, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jun. 29, 2018, 11 pages.
Exhibit 2; Notice of Allowance for U.S. Pat. No. 8,990,099, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jun. 29, 2018, 15 pages.
Exhibit 3; Non-Final Office Action for U.S. Pat. No. 9,367,665, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jun. 29, 2018, 12 pages.
Exhibit 4; Response to Non-Final Office Action for U.S. Pat. No. 9,367,665, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jun. 29, 2018, 18 pages.
Defendant Health Care Logistics, Inc.'s Reply in Support of Motion for Judgment on the Pleadings Pursuant to Fed. R. Civ. P. 12(C), *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jul. 20, 2018, 22 pages.
Exhibit A, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jul. 20, 2018, 43 pages.
Exhibit B; Plaintiff Kit Check, Inc.'s Disclosure of Asserted Claims and Infringement Contentions under Local Patent Rule 103.2, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jul. 20, 2018, 11 pages.
Plaintiff Kit Check, Inc.'s Motion to Strike Portions of Defendants' Reply or, in the Alternative, Motion for Leave to File a Sur-Reply, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Aug. 10, 2018, 6 pages.

(56) References Cited

OTHER PUBLICATIONS

Exhibit A; Plaintiff Kit Check, Inc.'s Sur-Reply in Opposition to Defendant's Motion for Judgment on the Pleadings, *Kit Check, Inc.* v. *Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Aug. 10, 2018, 5 pages.
Defendant Health Care Logistics, Inc.'s Memorandum in Opposition to Plaintiff Kit Check, Inc.'s Motion to Strike Portions of Defendant's Reply or, in the Alternative, Motion for Leave to File a Sur-Reply, *Kit Check, Inc.* v. *Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Aug. 31, 2018, 6 pages.
Plaintiff Kit Check, Inc.'s Reply in Support of its Motion to Strike Portions of Defendant's Reply or, in the Alternative, Motion for Leave to File a Sur-Reply, *Kit Check, Inc.* v. *Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Sep. 14, 2018, 7 pages.
Joint Claim Construction and Prehearing Statement, *Kit Check, Inc.* v. *Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Sep. 20, 2018, 21 pages.
Plaintiff Kit Check, Inc.'s Opening Claim Construction Brief, *Kit Check, Inc.* v. *Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Nov. 16, 2018, 50 pages.
Exhibit 1; Disputed Claim Terms Chart, *Kit Check, Inc.* v. *Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Nov. 16, 2018, 4 pages.
Declaration of Jeffrey Fischer, *Kit Check, Inc.* v. *Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Nov. 16, 2018, 24 pages.
Defendant Health Care Logistics, Inc.'s Opening Claim Construction Brief, *Kit Check, Inc.* v. *Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Nov. 16, 2018, 32 pages.
Exhibit 1002; File History of U.S. Pat. No. 9,367,665, *Health Care Logistics, Inc.* v. *Kit Check, Inc.*, Case No. PGR2019-00022, Nov. 30, 2018, 256 pages.
Exhibit 1003; Expert Declaration, *Health Care Logistics, Inc.* v. *Kit Check, Inc.*, Case No. PGR2019-00022, Nov. 30, 2018, 9 pages.
Exhibit 1013; Claim Construction Brief (Defendant), *Health Care Logistics, Inc.* v. *Kit Check, Inc.*, Case No. PGR2019-00022, Nov. 30, 2018, 32pages.
Exhibit 1014; Claim Construction Brief (Plaintiff), *Health Care Logistics, Inc.* v. *Kit Check, Inc.*, Case No. PGR2019-00022, Nov. 30, 2018, 50 pages.
Petition for Inter Partes Review of U.S. Pat. No. 8,990,099, *Health Care Logistics, Inc.* v. *Kit Check, Inc.*, Case No. IPR2019-00376, Nov. 30, 2018, 42 pages.

Exhibit 1002; File History of U.S. Pat. No. 8,990,099, *Health Care Logistics, Inc.* v. *Kit Check, Inc.*, Case No. IPR2019-00376, Nov. 30, 2018, 557 pages.
Exhibit 1003; Expert Declaration,*Health Care Logistics, Inc.* v. *Kit Check, Inc.*, Case No. IPR2019-00376, Nov. 30, 2018, 9 pages.
Exhibit 1010; Claim Construction Brief (Defendant), *Health Care Logistics, Inc.* v. *Kit Check, Inc.*, Case No. IPR2019-00376, Nov. 30, 2018, 32 pages.
Exhibit 1011; Claim Construction Brief (Plaintiff), *Health Care Logistics, Inc.* v. *Kit Check, Inc.*, Case No. IPR2019-00376, Nov. 30, 2018, 50 pages.
Petition for Inter Partes Review of U.S. Pat. No. 9,058,412, *Health Care Logistics, Inc.* v. *Kit Check, Inc.*, Case No. IPR2019-00385, Nov. 30, 2018, 75 pages.
Exhibit 1002; File History of U.S. Pat. No. 9,058,412, *Health Care Logistics, Inc.* v. *Kit Check, Inc.*, Case No. IPR2019-00385, Nov. 30, 2018, 75 pages.
Exhibit 1003; Expert Declaration, *Health Care Logistics, Inc.* v. *Kit Check, Inc.*, Case No. IPR2019-00385, Nov. 30, 2018, 9 pages.
Exhibit 1013; Claim Construction Brief (Defendant), *Health Care Logistics, Inc.* v. *Kit Check, Inc.*, Case No. IPR2019-00385, Nov. 30, 2018, 32 pages.
Exhibit 1014; Claim Construction Brief (Plaintiff), *Health Care Logistics, Inc.* v. *Kit Check, Inc.*, Case No. IPR2019-00385, Nov. 30, 2018, 50 pages.
Petition for Inter Partes Review of U.S. Pat. No. 9,058,413, *Health Care Logistics, Inc.* v. *Kit Check, Inc.*, Case No. IPR2019-00387, Dec. 1, 2018, 73 pages.
Exhibit 1002; File History of U.S. Pat. No. 9,058,413, *Health Care Logistics, Inc.* v. *Kit Check, Inc.*, Case No. IPR2019-00387, Dec. 1, 2018, 549 pages.
Exhibit 1003; Expert Declaration, *Health Care Logistics, Inc.* v. *Kit Check, Inc.*, Case No. IPR2019-00387, Dec. 1, 2018, 9 pages.
Exhibit 1009; Children's Hospital Boston Joins Others Using RFID to Track Implantables, *Health Care Logistics, Inc.* v. *Kit Check, Inc.*, Case No. IPR2019-00387, Dec. 1, 2018, 3 pages.
Exhibit 1012; The "Orange Book", *Health Care Logistics, Inc.* v. *Kit Check, Inc.*, Case No. IPR2019-00387, Dec. 1, 2018, 1103 pages.
Exhibit 1013; Claim Construction Brief (Defendant), *Health Care Logistics, Inc.* v. *Kit Check, Inc.*, Case No. IPR2019-00387, Dec. 1, 2018, 32 pages.
Exhibit 1014; Claim Construction Brief (Plaintiff), *Health Care Logistics, Inc.* v. *Kit Check, Inc.*, Case No. IPR2019-00387, Dec. 1, 2018, 50 pages.
Petition for Inter Partes Review of U.S. Pat. No. 9,805,169, *Health Care Logistics, Inc.* v. *Kit Check, Inc.*, Case No. IPR2019-00388, Dec. 1, 2018, 76 pages.
Exhibit 1002; File History of U.S. Pat. No. 9,805,169, *Health Care Logistics, Inc.* v. *Kit Check, Inc.*, Case No. IPR2019-00388, Dec. 1, 2018, 286 pages.
Exhibit 1003; Expert Declaration, *Health Care Logistics, Inc.* v. *Kit Check, Inc.*, Case No. IPR2019-00388, Dec. 1, 2018, 9 pages.
Exhibit 1009; Claim Construction Brief (Defendant), *Health Care Logistics, Inc.* v. *Kit Check, Inc.*, Case No. IPR2019-00388, Dec. 1, 2018, 32 pages.
Exhibit 1010; Claim Construction Brief (Plaintiff), *Health Care Logistics, Inc.* v. *Kit Check, Inc.*, Case No. IPR2019-00388, Dec. 1, 2018, 50 pages.
Petition for Inter Partes Review of U.S. Pat. No. 9,367,665, *Health Care Logistics, Inc.* v. *Kit Check, Inc.*, Case No. IPR2019-00394, Dec. 3, 2018, 69 pages.
Exhibit 1002; File History of U.S. Pat. No. 9,367,665, *Health Care Logistics, Inc.* v. *Kit Check, Inc.*, Case No. IPR2019-00394, Dec. 3, 2018, 256 pages.
Exhibit 1003; Expert Declaration, *Health Care Logistics, Inc.* v. *Kit Check, Inc.*, Case No. IPR2019-00394, Dec. 3, 2018, 9 pages.
Exhibit 1013; Claim Construction Brief (Defendant), *Health Care Logistics, Inc.* v. *Kit Check, Inc.*, Case No. IPR2019-00394, Dec. 3, 2018, 32 pages.
Exhibit 1014; Claim Construction Brief (Plaintiff), *Health Care Logistics, Inc.* v. *Kit Check, Inc.*, Case No. IPR2019-00394, Dec. 3, 2018, 50 pages.

(56) References Cited

OTHER PUBLICATIONS

Plaintiff Kit Check, Inc.'s Notice of Filing Deposition Transcript of Jeffrey Fischer, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jan. 3, 2019, 3 pages.
Exhibit A; Deposition of Jeffrey Fischer, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jan. 3, 2019, 86 pages.
Plaintiff Kit Check, Inc.'s Responsive Claim Construction Brief, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jan. 3, 2019, 23 pages.
Exhibit A, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jan. 3, 2019, 43 pages.
Exhibit B; Deposition of Jeffrey Fischer, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jan. 3, 2019, 22 pages.
Defendant Health Care Logistics, Inc.'s Response to Plaintiff Kit Check, Inc.'s Opening Claim Construction Brief, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jan. 3, 2019, 22 pages.
Plaintiff Kit Check, Inc.'s Memorandum in Opposition to Defendant Health Care Logistics, Inc.'s Motion for Stay, *Kit Check, Inc. v. Health Care Logistics, Inc.* (involving U.S. Pat. No. U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Feb. 11, 2019, 21 pages.
Exhibit 1; Defendant Health Care Logistics, Inc.'s Invalidity Contentions Pursuant to Local Patent Rule 103.4, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Feb. 11, 2019, 26 pages.
Defendant Health Care Logistics, Inc.'s Reply in Support of Motion for Stay, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Feb. 25, 2019, 10 pages.
Patent Owner's Preliminary Response, *Health Care Logistics, Inc. v. Kit Check, Inc.*, Case No. IPR2019-00376, U.S. Pat. No. 8,990,099, Mar. 8, 2019, 26 pages.
Patent Owner's Preliminary Response, *Health Care Logistics, Inc. v. Kit Check, Inc.*, Case No. IPR2019-00385, U.S. Pat. No. 9,058,412 B2, Mar. 8, 2019, 28 pages.
Patent Owner's Preliminary Response, *Health Care Logistics, Inc. v. Kit Check, Inc.*, Case No. IPR2019-00387, U.S. Pat. No. 9,058,413 B2, Mar. 13, 2019, 28 pages.
Patent Owner's Preliminary Response, *Health Care Logistics, Inc. v. Kit Check, Inc.*, Case No. IPR2019-00388, U.S. Pat. No. 9,805,169 B2, Mar. 13, 2019, 25 pages.
Patent Owner's Preliminary Response, *Health Care Logistics, Inc. v. Kit Check, Inc.*, Case No. IPR2019-00394, U.S. Pat. No. 9,367,668 B2, Mar. 13, 2019, 28 pages.
Opinion & Order, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Mar. 14, 2019, 17 pages.
Joint Stipulation of Partial Dismissal Without Prejudice, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Apr. 16, 2019, 2 pages.
Transcript of Markman Hearing Proceedings, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), May 6, 2019, 74 pages.
Decision Denying Institution of Inter Partes Review 35 U.S.C. §314, *Health Care Logistics, Inc. v. Kit Check, Inc.*, Case No. IPR2019-00385, U.S. Pat. No. 9,058,412 B2, Jun. 3, 2019, 28 pages.
Decision Denying Institution of Inter Partes Review 35 U.S.C. §314, *Health Care Logistics, Inc. v. Kit Check, Inc.*, Case No. IPR2019-00385, U.S. Pat. No. 9,805,169 B2, Jun. 3, 2019, 20 pages.
Decision Denying Institution of Inter Partes Review 35 U.S.C. §314, *Health Care Logistics, Inc. v. Kit Check, Inc.*, Case No. IPR2019-00376, U.S. Pat. No. 8,990,099 B2, Jun. 4, 2019, 18 pages.
Decision Denying Institution of Inter Partes Review 35 U.S.C. §314, *Health Care Logistics, Inc. v. Kit Check, Inc.*, Case No. IPR2019-00387, U.S. Pat. No. 9,058,413 B2, Jun. 7, 2019, 26 pages.
Decision Denying Institution of Inter Partes Review 35 U.S.C. §314, *Health Care Logistics, Inc. v. Kit Check, Inc.*, Case No. IPR2019-00394, U.S. Pat. No. 9,367,665 B2, Jun. 11, 2019, 25 pages.
Stipulation and [Proposed] Order Granting Leave to Amend Plaintiff's Infringement Contentions and Defendant's Invalidity Contentions, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jul. 3, 2019, 3 pages.
Defendant Health Care Logistics, Inc.'s Motion for Leave to File Second Amended Answer, Affirmative Defenses, and Counterclaims, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jul. 17, 2019, 5 pages.
Exhibit A; Defendant's Second Amended Answer, Affirmative Defenses, and Counterclaims to Plaintiff's Complaint, *Kit Check, Inc. v. Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jul. 17, 2019, 49 pages.
Request for ExParteReexamination Under 35 U.S.C. 302-307 and 37 C.F.R. 1.510, U.S. Pat. No. 8,990,099 B2, U.S. Appl. No. 13/554,342, filed Jul. 25, 2019 in 80 pages.
Request for ExParteReexamination Under 35 U.S.C. 302-307 and 37 C.F.R. 1.510, U.S. Pat. No. 9,058,412 B2, U.S. Appl. No. 14/603,730, filed Jul. 26, 2019 in 118 pages.
Request for ExParteReexamination Under 35 U.S.C. 302-307 and 37 C.F.R. 1.510, U.S. Pat. No. 9,058,413 B2, U.S. Appl. No. 14/603,828, filed Jul. 25, 2019 in 151 pages.
Request for ExParteReexamination Under 35 U.S.C. 302-307 and 37 C.F.R. 1.510, U.S. Pat. No. 9,805,169 B2, U.S. Appl. No. 14/701,958, filed Jul. 26, 2019 in 220 pages.
Request for ExParteReexamination Under 35 U.S.C. 302-307 and 37 C.F.R. 1.510, U.S. Pat. No. 9,367,665 B2, U.S. Appl. No. 14/818,113, filed Jul. 26, 2019 in 164 pages.

(56) References Cited

OTHER PUBLICATIONS

Opinion & Order, *Kit Check, Inc.* v. *Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Aug. 30, 2019, 26 pages.
Bryant, Blake, "Hacking SIEMs to Catch Hackers: Decreasing the Mean Time to Respond to Network Security Events with a Novel Threat Ontology in SIEM Software", Master's Thesis, University of Kansas, 2016, pp. 257.
Pace et al., "Distributed Ambulatory Research in Therapeutics Network (DARTNet): Summary Report", Effective Health Care Research Reports, No. 14, Agency for Healthcare Research and Quality, Jul. 2009, pp. 41.
"AmerisourceBergen Specialty Group Reconfigures Cubixx Medical Cabinet", Jan. 9, 2011, pp. 2, https://web.archive.org/web/20180620192642/http://pharmaceuticalcommerce.com/supply-chain-logistics/amerisourcebergen-specialty-group-reconfigures-cubixx-medical-cabinet/.
Bacheldor, Beth, "ASD Healthcare Deploys RFID Refrigerated Drug Cabinets", RFID Journal, Sep. 24, 2007, p. 1. http://www.rfidjournal.com/articles/view?3632.
Bacheldor, Beth, "Cardinal Health Readies Item-Level Pilot", RFID Journal, May 31, 2006, p. 1. http://www.rfidjournal.com/articles/view?2380.
Bacheldor, Beth, "UCSD Medical Center Expands Its RFID Deployment", RFID Journal, Oct. 29, 2008, pp. 2. http://www.rfidjournal.com/articles/view?4423.
Bacheldor, Beth, "UMass Med Center Finds Big Savings Through Tagging", RFID Journal, Nov. 21, 2007, pp. 2. http://www.rfidjournal.com/articles/view?3763/2.
Becker et al., "SmartDrawer: RFID-Based Smart Medicine Drawer for Assistive Environments", Conference: Proceedings of the 2nd International Conference on Pervasive Technologies Related to Assistive Environments, PETRA 2009, Corfu, Greece, Jun. 9-13, 2009, pp. 8.
Bendavid et al., "Using RFID to Improve Hospital Supply Chain Management for High Value and Consignment Items", Procedia Computer Science, vol. 5, 2011, pp. 849-856.
Bendavid et al., "Redesigning the Replenishment Process of Medical Supplies in Hospitals with RFID", Business Process Management Journal, 2010, vol. 16, No. 6, pp. 991-1013.
Cangialosi et al., "Leveraging RFID in Hospitals: Patient Life Cycle and Mobility Perspectives", IEEE Applications & Practice, Sep. 2007, pp. 18-23.
Chao et al., "Determining Technology Trends and Forecasts of RFID by a Historical Review and Bibliometric Analysis from 1991 to 2005", Technovation, vol. 27, 2007, pp. 268-279.
Collins, "RFID Cabinet Manages Medicine", RFID Journal, Aug. 12, 2004, p. 1. http://www.rfidjournal.com/articles/view?1081.
"Data Gathering Developments", Manufacturing Chemist, Feb. 1, 2005, p. 24. https://www.manufacturingchemist.com/news/article_page/Data_gathering_developments/35805.
Dutta et al., "RFID and Operations Management: Technology, Value, and Incentives", Production and Operations Management (POMS), vol. 16, No. 5, Sep.-Oct. 2007, pp. 646-655.
Edwards, John, "RFID Smart Shelves and Cabinets", RFID Journal, Aug. 24, 2009, pp. 4. http://www.rfidjournal.com/articles/view?5140/4.
Erdem et al., "Investigation of RFID Tag Readability for Pharmaceutical Products at Item Level", Drug Development and Industrial Pharmacy, 2009, vol. 35, No. 11, pp. 1312-1324.
Fahrni, Jerry, "More RFID Refrigerator Stuff—Cubixx and myCubixx", Sep. 3, 2012, pp. 4. http://jerryfahmi.com/2012/09/more-rfid-refrigerator-stuff-cubixx-and-mycubixx/.
"Faraday Cage", Wikipedia, last edited Apr. 12, 2018, pp. 5. https://en.wikipedia.org/wiki/Faraday_cage.
Floerkemeier et al., "The Smart Box Concept for Ubiquitous Computing Environments", The Smart Box Concept for Ubiquitous Computing Environments, 2004, pp. 4.

Green, Kathryn, "Doing the Wave: Inventory Management with RFID", Diagnostic & Interventional Services, UMass Memorial Medical Center, Worcester, MA, vol. 15, No. 9, Sep. 2007, pp. 7. https://www.cathlabdigest.com/articles/Doing-Wave-Inventory-Management-RFID.
Ho et al., "A Prototype on RFID and Sensor Networkds for Elder Healthcare: Progress Report", SIGCOMM '05 Workshops, Aug. 22-26, 2005, Philadelphia, PA, pp. 70-75.
Howard, JD, "Implementation of RFID in the Pharmaceutical Industry", Advisor: Dr. Jay Singh, California Polytechnic State University, San Luis Obispo, CA, Feb. 2009, pp. 11.
Humble, RN, Carol, "How RFID Freed Nurses From the Pain of Inventory Duties", Cath Lab Digest, Dec. 2009, vol. 17, No. 12. https://www.cathlabdigest.com/articles/How-RFID-Freed-Nurses-From-Pain-Inventory-Duties.
"Intel & Siemens Launch RFID Blood Bank in Malaysia", RFID Journal, Aug. 16, 2007, p. 1. https://www.rfidjournal.com/articles/view?6801.
Jones et al., "The Benefits, Challenges and Impacts of Radio Frequency Identification Technology (RFID) for Retailers in the UK", Marketing Intelligence & Planning, Mar. 2005, vol. 23, No. 4, pp. 395-402.
Juels, Ari, "RFID Security and Privacy: A Research Survey", IEEE Journal on Selected Areas in Communications, vol. 24, No. 2, Feb. 2006, pp. 381-394.
Lahtela et al., "RFID and NFC in Healthcare: Safety of Hospitals Medication Care", 2008 Second International Conference on Pervasive Computing Technologies for Healthcare, Tampere, Finland, Jan. 30-Feb. 1, 2008, pp. 4.
Lewis, Mark O., "RFID-Enabled Capabilities and their Impact on Healthcare Process Performance", 31st International Conference on Information Systems, St. Louis, 2010, pp. 1-20.
Liu et al., "Point-of-Care Support for Error-Free Medication Process" (Jun. 25, 2007), retrieved Aug. 21, 2017, 12 pages, available at http://ieeexplore.ieee.org/document/4438162/.
McCall et al., "RMAIS: RFID-based Medication Adherence Intelligence System" (Aug. 31, 2010), retrieved Aug. 21, 2017, 4 pages, available at http://ieeexplore.ieee.org/document/5627529/.
Mehrjerdi, Yahia Zare, "RFID-Enabled Healthcare Systems: Risk-Benefit Analysis", International Journal of Pharmaceutical and Healthcare Marketing, 2010, vol. 4, No. 3, pp. 282-300.
Meiller et al., "Adaptive Knowledge-Based System for Health Care Applications with RFID-Generated Information", Decision Support Systems, vol. 51, 2011, pp. 198-207.
Mowry, Mike, "A Survey of RFID in the Medical Industry: With Emphasis on Applications to Surgery and Surgical Devices", MAE188, Introduction to RFID, Dr. Rajit Gadh, UCLA, Jun. 9, 2008, pp. 22.
"New RFID Medical Cabinets Deployed at 50 Hospitals", RFID Journal, Sep. 17, 2007, pp. 2. https://www.rfidjournal.com/articles/view?6823.
O'Connor, Mary Catherine, "Drug Distributor Uses RFID to Vend Meds", RFID Journal, May 23, 2006, pp. 2. https://www.rfidjournal.com/articles/view?2363/2.
O'Connor, Mary Catherine, "GlaxoSmithKline Tests RFID on HIV Drug", RFID Journal, Mar. 24, 2006, pp. 2. https://www.rfidjournal.com/articles/view?2219/.
O'Connor, Mary Catherine, "Interrogators Start to Evolve", RFID Journal, Jun. 1, 2006, pp. 3. https://www.rfidjournal.com/purchase-access?type=Article&id=2398&r=%2Farticles%2Fview%3F2398.
O'Connor, Mary Catherine, "Johnson & Johnson Finds Value in Multiple RFID Apps", RFID Journal, Apr. 23, 2008, pp. 2. https://www.rfidjournal.com/articles/pdf?4046.
O'Connor, Mary Catherine, "McKesson Starts RFID Pilot for Viagra", RFID Journal, Feb. 17, 2005, pp. 2. https://www.rfidjournal.com/articles/view?2157.
O'Connor, Mary Catherine, "Pfizer Using RFID to Fight Fake Viagra", RFID Journal, Jun. 6, 2006, pp. 2. https://www.rfidjournal.com/articles/pdf?2075.
Parida et al., "Application of RFID Technology for In-House Drug Management System", 15th International Conference on Network-Based Information Systems, 2012, pp. 577-581.

(56) References Cited

OTHER PUBLICATIONS

"RFID Medical Cabinets Evaluated in New Benchmark", RFID Journal, Sep. 12, 2007, pp. 2. https://www.rfidjournal.com/articles/view?6819.
Roberti, Mark, "RFID Basics for Health Care, RFID in Health Care", Produced by RFID Journal, Sep. 17, 2009, The Westin Waltham-Boston, Waltham, MA, pp. 33.
Saygin, C., "Adaptive Inventory Management Using RFID Data", The International Journal of Advanced Manufacturing Technology, 2007, vol. 32, pp. 1045-1051.
Singh et al., "Versatility of Radio Frequency Identification (RFID) Tags in the Pharmaceutical Industry", Instrumentation Science and Technology, vol. 36, pp. 656-663, 2008.
Swedberg, Claire, "Tennessee Hospital Tracks High-Value Items", RFID Journal, Aug. 5, 2009, pp. 2. http://www.rfidjournal.com/articles/view?5106.
Tsai et al., "iMAT: Intelligent Medication Administration Tools" (Jul. 1, 2010), retrieved Aug. 21, 2017, 8 pages, available at http://ieeexplore.ieee.org/document/5556551/.
Tsai et al., "Smart Medication Dispenser: Design, Architecture and Implementation" (Sep. 27, 2010), retrieved Aug. 21, 2017, 12 pages, available at http://ieeexplore.ieee.org/document/5585838/.
Wang et al., "RFID Applications in Hospitals: A Case Study on a Demonstration RFID Project in a Taiwan Hospital", Proceedings of the 39th Hawaii International Conference on System Sciences, 2006, pp. 1-10.
Wasserman, Elizabeth, "Purdue Pharma to Run Pedigree Pilot", RFID Journal, May 31, 2005, pp. 2. http://www.rfidjournal.com/articles/view?1626.
Complaint, *Kit Check, Inc.* v. *Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Dec. 1, 2017, 45 pages.
Defendant's Answer, Affirmative Defenses and Counterclaims to Plaintiff's Complaint, *Kit Check, Inc.* v. *Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jan. 2, 2018, 43 pages.
Defendant's First Amended Answer, Affirmative Defenses and Counterclaims to Plaintiff's Complaint, *Kit Check, Inc.* v. *Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Feb. 9, 2018, 43 pages.
Defendant Health Care Logistics, Inc's Invalidity Contentions Pursuant to Local Patent Rule 103.4, *Kit Check, Inc.* v. *Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jun. 18, 2018, 25 pages.
Exhibit 1; Initial Invalidity Claim Chart for U.S. Pat. No. 8,990,099, *Kit Check, Inc.* v. *Health Care Logistics, Inc.*, Case No. 2:17-cv-01041-ALM-CMV (S.D. Ohio), Jun. 18, 2018, 51 pages.
Exhibit 2; Initial Invalidity Claim Chart for U.S. Pat. No. 9,058,413, *Kit Check, Inc.* v. *Health Care Logistics, Inc.*, Case No. 2:17-cv-01041-ALM-CMV (S.D. Ohio), Jun. 18, 2018, 94 pages.
Exhibit 3; Initial Invalidity Claim Chart for U.S. Pat. No. 9,058,412, *Kit Check, Inc.* v. *Health Care Logistics, Inc.*, Case No. 2:17-cv-01041-ALM-CMV (S.D. Ohio), Jun. 18, 2018, 83 pages.
Exhibit 4; Initial Invalidity Claim Chart for U.S. Pat. No. 9,734,294, *Kit Check, Inc.* v. *Health Care Logistics, Inc.*, Case No. 2:17-cv-01041-ALM-CMV (S.D. Ohio), Jun. 18, 2018, 58 pages.
Exhibit 5; Initial Invalidity Claim Chart for U.S. Pat. No. 9,805,169, *Kit Check, Inc.* v. *Health Care Logistics, Inc.*, Case No. 2:17-cv-01041-ALM-CMV (S.D. Ohio), Jun. 18, 2018, 251 pages.
Exhibit 6; Initial Invalidity Claim Chart for U.S. Pat. No. 9,037,479, *Kit Check, Inc.* v. *Health Care Logistics, Inc.*, Case No. 2:17-cv-01041-ALM-CMV (S.D. Ohio), Jun. 18, 2018, 43 pages.
Exhibit 7; Initial Invalidity Claim Chart for U.S. Pat. No. 9,367,665, *Kit Check, Inc.* v. *Health Care Logistics, Inc.*, Case No. 2:17-cv-01041-ALM-CMV (S.D. Ohio), Jun. 18, 2018, 109 pages.
Exhibit L; Fagron Academy, *Kit Check, Inc.* v. *Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Dec. 1, 2017, 2 pages.
Plaintiff's Answer to Defendant's Counterclaims, *Kit Check, Inc.* v. *Health Care Logistics, Inc.* (involving U.S. Pat. No. 8,990,099, U.S. Pat. No. 9,037,479, U.S. Pat. No. 9,058,412, U.S. Pat. No. 9,058,413, U.S. Pat. No. 9,367,665, U.S. Pat. No. 9,734,294, and U.S. Pat. No. 9,805,169), Case No. 2:17-cv-01041-ALM-CMV (S.D. Ohio), Jan. 19, 2018, 14 pages.
Barlas, Stephen, "Pharmacy Product Tracing Likely to Go National—Costs to Pharmacies Worrisome," Pharmacy & Therapeutics, Jan. 2009, vol. 34 No. 1, p. 14.
Belson, D., "Storage, Distribution, and Dispensing of Medical Supplies," CREATE Interim Report Under FEMA Grant EMW-2004-GR-0112, Apr. 21, 2005, pp. 1-36.
Çakici et al., "Using RFID for the management of pharmaceutical inventory-system optimization and shrinkage control," Decision Support Systems, 2011, pp. 842-852.
CPG Sec. 400.210, Radiofrequency Identification Feasibility Studies and Pilot Programs for Drugs Nov. 2004 Compliance Policy Guide available at: http://www.fda.goy/ICECI/ComplianceManuals/CompliancePolicyGuidanceManual/ucm074357.htm.
Crash Cart Inventory Checklist, Outpatient Surgery Magazine, Oct. 2004, "Outpatient Surgery", available at: http://www.outpatientsurgery.net/resources/forms/2004/pdf/OutpatientSurgeryMagazine_0410_crashCart.pdf, in 1 page.
Curtin et al., "Making the 'MOST' out of RFID: a research agenda for the study of the adoption, usage and impact of RFID," Information Technology Management, Apr. 2007, pp. 87-110.
Gonzalez, Stephanie, "Health Maintenance System (HMS) Hardware Research, Design, and Collaboration," NASA USRP—Internship Final Report, 2010, pp. 1-20.
Harrop et al., "RFID for Healthcare and Pharmaceuticals, 2008-2018," Securing Pharma, May 2008, pp. 1-12.
Houliston, Bryan, "Integrating RFID Technology into a Drug Administration System," Bulletin of Applied Computing and Information Technology, vol. 3, No. 1, May 2005, pp. 8. Retrieved Sep. 26, 2013 from http://citrenz.ac.nz/bacit/0301/2005Houliston_RFID.htm.
Jorgensen et al., "Executable Use Cases: Requirements for a Pervasive Health Care System," IEEE Software, Mar./Apr. 2004, pp. 34-41.
Lai et al., "Enhancing Medication Safety and Reduce Adverse Drug Events on Inpatient Medication Administration using RFID," WSEAS Transactions on Communications, Oct. 2008, vol. 7, No. 10, pp. 1045-1054.
Lampe et al., "The Smart Box Application Model," Advances in Pervasive Computing, 2004, pp. 1-6.
"McKesson's Announces New Touch-Screen Driven Medication Dispensing Solution", Business Wire, Jun. 15, 2009, pp. 2, Available at: http://www.businesswire.com/news/home/20090615005349/en/McKesson-Announces-Touch-Screen-Driven-Medication-Dispensing-Solution#.VR7quPnF_10.
"Medical Packaging Inc. Announces Clear Stem Flag Label System for Ampoules, Vials, and Syringes" Feb. 1, 2006 available at: http://www.medpak.com/v1/news/20060201_CSFLAG.pdf, in 1 page.
O'Connor, Mary Catherine, "To Keep Drugs from Expiring, Hospital Tests Intelliguard System", RFID Journal, Jan. 12, 2011, pp. 3. http://www.rfidjournal.com/articles/view?8123.
O'Driscoll et al, "RFID: An Ideal Technology for Ubiquitous Computing?" Dublin Institute of Technology School of Electronic and Communications Conference Papers, Jan. 1, 2008, pp. 1-17.
Pappu, Ph.D. et al., "RFiD in Hospitals: Issues and Solutions" Consortium for the Accelerated Deployment of RFID in Distribution, Sep. 2004, pp. 1-12.

(56) References Cited

OTHER PUBLICATIONS

Tzeng et al., "Evaluating the Business Value of RFID: Evidence from Five Case Studies," International Journal of Production Economics, 2008, vol. 112, pp. 601-613.
Wang et al., "Applying RFID Technology to Develop a Distant Medical Care Service Platform," International Journal of Electronic Business Management, 2010, vol. 8, No. 2, pp. 161-170.
International Search Report and Written Opinion in PCT Application No. PCT/US2014/053837 dated Nov. 24, 2014.
International Preliminary Report on Patentability and Written Opinion in PCT Application No. PCT/US2014/053837 dated Jan. 19, 2017.

* cited by examiner

Add Formulary Item to Segment

400

NDC: 0409-7241-61

Manufacturer: Hospira

Name: Epinephrine Injection USP (1:1000)

Strength: 1 mg/mL

Package: 2 mL syringe

Add to Segment: [Epinephrine ▶]

Add to Fill Option: ○ Preferred Fill Option
○ Alternative Fill Option

[Cancel]  [Save]

FIG.4

Edit Fill Option

Quantity: 2    Billing Code: 10468

Add Items

[ epi    ⊗ ]

| NDC | Manufacturer | Name | Strength | Package | |
|---|---|---|---|---|---|
| 0409-7241-61 | Hospira | Epinephrine Injection USP (1:1000) | 1 mg/mL | 2 mL syringe | + Add |
| 0409-3375-04 | Med Tools | Norepinephrine Bitartrate | 1 mg/mL | 4 mL syringe | + Add |
| 42023-101-10 | Acme Inc | EPINEPHrine 1:1000 | 1 mg/mL | 30 mL vial | + Add<br>In another fill option in this segment |
| 0409-7241-01 | Hospira | EPINEPHrine HCl | 1 mg/mL | 25 mL ampule | + Add<br>In this fill option |
| 49502-500-01 | Acme Inc | EpiPen | 0.3 mg | 0.3 mL auto-injector | + Add<br>In another fill option in this kit |

Items in Fill Option (3)

| NDC | Manufacturer | Name | Strength | Package | |
|---|---|---|---|---|---|
| 0409-7241-01 | Hospira | EPINEPHrine HCl | 1 mg/mL | 25 mL ampule | × Remove |
| 0409-7241-81 | Hospira | Epinephrine USP (1:1000) | 1 mg/mL | 25 mL vial | × Remove |
| 517113005 | Unknown | Epinephrine | | 25 mL vial | × Remove |

[ Cancel ]    [ Done ]

| Edit Segment | ⓘ |

General OR Kit

Segment Name: [ Epinephrine inj 1 mg/mL ]

Fill Options

If the items in your kit match any one of the fill options below, the segment will be considered complete; otherwise, Kit Check will show which items are missing or extra based on the preferred template.

[ + Add Fill Option ]

Preferred Fill Option  Edit

Quantity 3   Billing Code 10468   Created May 1, 2014

| NDC | Manufacturer | Name | Strength | Package |
|---|---|---|---|---|
| 0409-7241-01 | Hospira | EPINEPHrine HCl | 1 mg/mL | 25 mL ampule |
| 999-01-0296 | Hospital | Epinephrine | | 25 mL vial |

Alternative Fill Option  Set as Preferred  Delete  Edit

Quantity 2   Billing Code 10465   Created July 31, 2013

| NDC | Manufacturer | Name | Strength | Package |
|---|---|---|---|---|
| 0409-7241-01 | Hospira | EPINEPHrine HCl | 1 mg/mL | 25 mL ampule |
| 0409-7241-81 | Hospira | Epinephrine USp (1;1000) | 1 mg/mL | 25 mL vial |
| 517113005 | Unknown | Epinephrine | | 25 mL vial |

[ Delete Segment ]   [ Cancel ]  [ Save ]

FIG.6

Item Summary by Segment

700

| Segment | Item Count | Earliest Expiration Date | Used |
|---|---|---|---|
| Albuterol Sulfate HFA 6.7 g | 2 [Extra: 1] | | Nov 30, 2015 |
| Ampicillin 1 g<br>□□ Matched a non-preferred fill option | 3 [Extra: 1] | | Jul 31, 2014<br>[in 36 days] |
| Ampicillin/Sulbactam 1.5 gm | 2 | | Mar 31, 2015 |
| Artificial Tear Eye Ointment | 4 [Extra: 1] | | Jan 31, 2017 |
| Atropine 0.4 mg/mL | 2 [Extra: 1] | | Jun 30, 2015 |

| KITCHECK | SCAN | Inventory | Tags | Reports | KitCheck TechTeam |

Manage Kit Masters

Kit Master: Anesthesia C-Section Tray ▼   Rename Kit Master

Anesthesia C-Section Tray Segments

+ New Segment

| Segment ▲ | Quantity | Billing Code |
|---|---|---|
| ▫▫ Diphenhydramine 50 mg/ml vial    (Show alternatives) | 1 | 10920 |
| Ephedrine 50 mg/ml ampule | — | — |
| ▫▫ Epinephrine 1:10,000 syringe    (Hide alternatives) | 1 | 10975 |
| (Preferred Fill Option) | — | — |
| (Alternative Fill Option) | 1 | 10980 |
| Esmolol 100 mg/10 ml vial | 2 | 10981 |
| Fentanyl 50 mcg/ml 2 ml | 1 | 10985 |
| Glycopyrrolate 0.2 mg/ml 5 ml vial | 5 | 14335 |
| ▫▫ Hydralazine 20 mg/ml vial    (Show alternatives) | 1 | 11009 |

*This segment has multiple fill options*

FIG.8

| Scan Summary | Scan Details |

All Items by Segment

| Segment ▼ | Manufacturer | Item / NDC / Lot Number | Expiration |
|---|---|---|---|
| Amiodarone inj 150 mg/3 mL<br>☐☐ Matched a non-preferred fill option | APP PHARMACEUTICAL | Amiodarone HCl 150MG/3ML 3ML<br>NDC: 63323-616-03<br>Lot: 6006935 | Jan 31, 2015 |
| | BIONICHE PHARMA GROUP | Amiodarone HCl 150MG/3ML 3ML<br>NDC: 67457-153-03<br>Lot: 130525 | Oct 31, 2014 |
| | BIONICHE PHARMA GROUP | Amiodarone HCl 150MG/3ML 3ML<br>NDC: 67457-153-03<br>Lot: 130525 | Oct 31, 2014 |
| | BIONICHE PHARMA GROUP | Amiodarone HCl 150MG/3ML 3ML<br>NDC: 67457-153-03<br>Lot: 130525 | Oct 31, 2014 |

Items Expiring Soon

| Item ▼ | Manufacturer | NDC | Lot Num | Expiration |
|---|---|---|---|---|
| Naloxone HCl 0.4 mg/mL<br>EPC: D8ED | HOSPIRA | 0409-1215-01 | 20175EV | Aug 1, 2014 |

[Print Billing Sheet]

Missing Items

| | Expected | Actual | Shortage |
|---|---|---|---|
| ▱▱ Epinephrine inj 1 mg/mL | 3 | 2 | 1 |
| ▱▱ Naloxone HCl 0.4 mg/mL | 2 | 1 | 1 |

[This segment has multiple fill options] (callout pointing to Epinephrine row)

Extra Items

| Segment ▲ | Expected | Actual | Surplus |
|---|---|---|---|
| Saline Water | 10 | 11 | 1 |

Wrong Items for this Kit

| Item ▼ | Manufacturer | NDC | Lot Num | Expiration |
|---|---|---|---|---|
| Dextrose 50%<br>EPC: 9753 | INTRNTL MEDICATION SYSTEM | 76329-3301-1 | bd043d3 | Mar 31, 2015 |

+ Add Formulary Item to Segment

| Segment | Permissible Items | Quantity |
|---|---|---|
| Medicine Bottle 1 | Product A<br>Product B | 1 |
| Medicine Vial 2 | Product C<br>Product D<br>Product E | 3 |
| Medicine Bag 3 | Product F | 2 |
| Solution Bottle 4 | Product G<br>Product H | 3 |
| Etc. | . . . | . . . |

FIG. 11B

All Items by Segment 105

| Segment | Brand | Item/NDC/Lot | Strength | Expiration |
|---|---|---|---|---|
| Adenosine Vial | | Adenosine Injection NDC: 1001906302 Lot: 916136 | 6 mg/2 mL | Feb 28,2013 |
| | Adenosine Injection | Adenosine Injection NDC: 1001906302 Lot: 916136 | 6 mg/2 mL | Feb 28,2013 |
| | Adenosine Injection | Adenosine Injection NDC: 1001906302 Lot: 916136 | 6 mg/2 mL | Nov 30,2013 |
| Albuterol IPPB Sol. | Ipratropium Bromide And Albuterol Sulfate | Ipratropium Bromide and Albuterol Sulfate NDC: 0487-0201-60 Lot: 76AN1 | 3; .5mg/3mL; mg/3mL | Dec 31,2017 |
| | Ipratropium Bromide And Albuterol Sulfate | Ipratropium Bromide and Albuterol Sulfate NDC: 0487-0201-60 Lot: 76AN1 | 3; .5mg/3mL; mg/3mL | Dec 31,2017 |
| Albuterol MDI | VENTOLIN | VENTOLIN NDC: 0173-0682-54 Lot: 1ZP6940 | 108 ug/1 | Nov 30,2012 |
| Amiodarone Vial | Amiodarone Hydrochloride | Amiodarone Hydrochloride NDC: 67457-153-03 Lot: 101210 | 50 mg/mL | Oct 31,2012 |
| | Amiodarone Hydrochloride | Amiodarone Hydrochloride NDC: 67457-153-03 Lot: 101210 | 50 mg/mL | Oct 31,2012 |
| Atropine Bristojet | | Atropine NDC: 0548-3339-00 Lot: 1 | 1 mg/10 mL | Feb 28,2014 |
| | | Atropine NDC: 0548-3339-00 Lot: 1 | 1 mg/10 mL | Feb 28,2014 |
| Calcium Chloride Bristoject | | Calcium Chloride NDC: 0548-3304-00 Lot: BA00219 | 100 mg.mL | Aug 30,2012 |
| | | Calcium Chloride | 100 mg.mL | Aug 30,2012 |

FIG. 11C

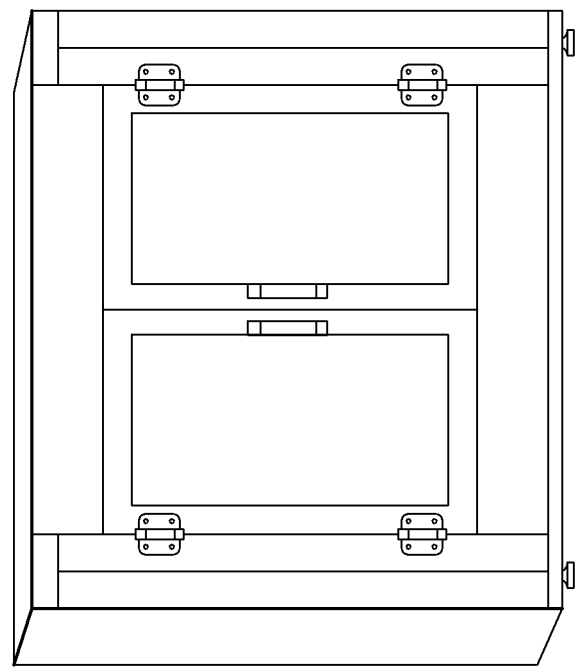
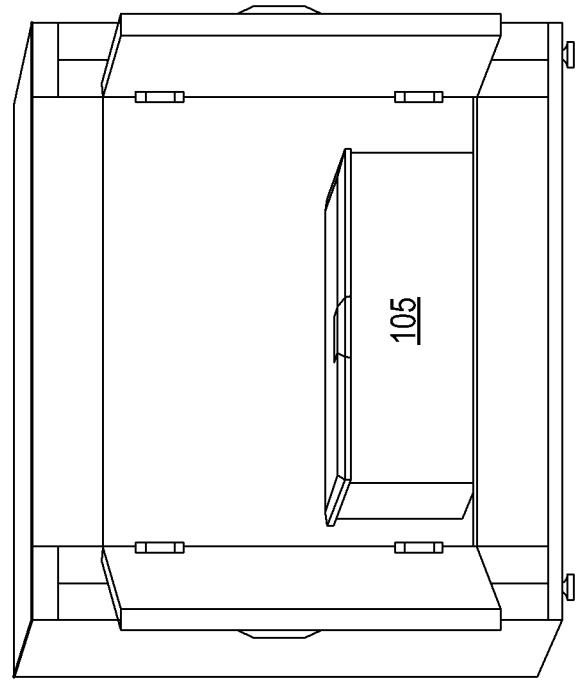
FIG. 12B

1001

905 — Pediatric Emergency Drug Tray | KitCheck-3
Drug Tray (3)

Scan | Kits | Reports | Print Tags

1005 — | 51 Total |
1010 — | 0 Extra | 1 Missing | 0 Expired | 2 Expiring |

Procainamide Hydrochloride on October 1, 2012

1015 — Last Scan   September 28, 2012   Scan History | Details

1020 — Items Expiring Soon

| Manufacturer | Item | Size | Item Num (NDC) | Lot Num | Expiration |
|---|---|---|---|---|---|
| Hospira, Inc. | Procainamide Hydrochloride | 500 mg/mL | 0409-1903-01 | 1 | October 1, 2012 |
| Hospira, Inc. | Procainamide Hydrochloride | 500 mg/mL | 0409-1903-01 | 1 | October 1, 2012 |

1025 — Missing Items

| Shortage | Item | Expected | Actual |
|---|---|---|---|
| 1 | Magnesium Sulfate Vial | 2 | 1 |

905 — Demo Kit Tray (9)

⚡ Scan  ◆ Kits  📊 Reports  🏷 Print Tags

1105 — | 26 Total | 0 Extra | 1 Missing | 1 Expired | 1 Expiring |

1110 — 💲 Bill to KRE1981  📍 Central Pharmacy  ⊞ Protopic on September 28, 2012  [Check Out] — 1135

1115 — Last Scan October 1, 2012  ▶ Show Scan History | Details

Expired Items — 1120

| Manufacturer | Item | Size | Lot Num | Expiration |
|---|---|---|---|---|
| Astellas | Protopic | 39487279 | 28841 | September 28, 2012 |

Items Expiring Soon — 1125

| Manufacturer | Item | Size | Item Num | Lot Num | Expiration |
|---|---|---|---|---|---|
| Alcon | Pataday Olopatadine Hydrochloride Opthalmic s | 1 Box | 650277224 | 174872F-1 | October 1, 2012 |

Extra Items — 1130

| Item | Expected | Actual | Surplus |
|---|---|---|---|
| Olopatadine Hydrochloride Opthalmic solution | 2 | 3 | 1 |
| Tacrolimus ointment 0.1% | 1 | 2 | 1 |

FIG. 20

Kits that needs rework

| Expand All | Collapse All | | | | |
|---|---|---|---|---|---|
| Demo Kit | | Qty Expected | Item Num (NDC) | Lot Num | Expiration |
| Fluticasone Propionate Nasal Spray 50 Mcg | Shortage:1 | 2 | | | January 1, 2012 |
| Gentamicin Sulfate USP 0.3% | | 1 | | | November 3, 2012 ⚠ |
| Bandage Kit – Gauge and overpacked | | Qty Expected | Item Num (NDC) | Lot Num | Expiration |
| Large Bandages | Shortage:3 | 3 | | | |
| Medium Bandages | Shortage:3 | 3 | | | |
| Round Bandages | Shortage:3 | 3 | | | |

FIG.22A

Select a Report: Kits containing a specific item or lot number ▶

Manufacturer Name

Item Name

Item Number (NDC)

Lot Number: PAA32

Kits containing a specific item or lot number

| Demo Kit | | Item Num (NDC) | Lot Num | Expiration |
|---|---|---|---|---|
| Teva | ProAir HFA | 1 Box | 5931057920 | PAA32A | January 1, 2012 |

| ⊙ Scan | ◆ Kits | ■ Reports | ◇ Print Tags | ✱ Admin | ⏻ |

Edit Item

Norepinephrine Bitartrate Injection, USP (Levophed™) (1 mg/mL)
NDC: 0409-3375-04
Lot # 112853a
Expiration: Apr 30, 2013

| | |
|---|---|
| Verification Status | Verified |
| Verified By | Mike |
| Verification Method | Batch Scan |
| Verified At | Aug 19, 2013 5:02 PM |

This item is not editable. Would you like to scan another item?

*Fig. 27*

Edit Item

⊙ Scan  ⧫ Kits  ▬ Reports  ⌖ Print Tags  ⚙ Admin  ⏻

2800

Adenosine

| | |
|---|---|
| Verification Status | Unverified |
| Verified By | - |
| Verification Method | - |
| Verified At | - |

To verify this item, read the NDC, lot number, and expiration date off of the drug's packaging and input it below.

NDC: [            ]

Lot Number: [            ] 🚫

Expiration Date: [            ] 🚫

[ Verify ]  [ Cancel ]

*Fig. 28*

Batch Item Verification

2900

⊙ Scan  ◈ Kits  ▦ Reports  ◇ Print Tags  ✱ Admin

It looks like you're trying to verify a batch of newly tagged items.

Please check that all items in the scanning station have the same NDC, Lot Number, and Expiration Date printed on the manufacture's label.

Please read the NDC, Lot Number, and Expiration Date off the manufacture's label and enter it in the fields below. Also, count the number of items present in the scanning station.

NDC
Lot Number
Expiration Date
Quantity

[ Submit ]

| Scan | Kits | Reports | Print Tags | Admin | ⏻ |

Edit Item

Adenosine

| Verification Status | Unverified |
| Verified By | - |
| Verification Method | - |
| Verified At | |

To verify this item, read the NDC, lot number, and expiration date off of the drug's packaging and input it below.

NDC: 25021-301-02
Lot Number: 7005414 🚫
Expiration Date: 2013-08-31 🚫

[ Verify ]  [ Cancel ]

⊙ Scan　◆ Kits　▦ Reports　◇ Print Tags　✱ Admin　⏻

Verification Required
Adult Anesthesia Kit | #1

There are items in this kit that need to verified. Please remove and verify the following:

- EPC# 80010000000000000000000060 – Thrombin – NDC 60793-2150-51 – Lot# 594671
- EPC# 80010000000000000000000087 – Thrombin – NDC 60793-2150-51 – Lot# 594671
- EPC# 80010000000000000000000187 – Procainamide Hydrochloride – NDC 0409-1903-01 – Lot# 23160EV

*Fig. 31*

MANAGEMENT OF PHARMACY KITS USING MULTIPLE ACCEPTANCE CRITERIA FOR PHARMACY KIT SEGMENTS

CROSS-REFERENCE TO RELATED APPLICATIONS

This application is a continuation of U.S. patent application Ser. No. 14/472,410, filed Aug. 29, 2014, which is a continuation-in-part of U.S. patent application Ser. No. 13/554,342, filed Jul. 20, 2012, now issued as U.S. Pat. No. 8,990,099, each of which is hereby incorporated by reference. U.S. patent application Ser. No. 13/554,342 claims priority benefit to U.S. Provisional Application No. 61/514,231, filed Aug. 2, 2011. U.S. patent application Ser. No. 14/472,410 also claims priority to U.S. Provisional Application No. 62/021,927, filed on Jul. 8, 2014, the subject matter of which is hereby incorporated by reference.

BACKGROUND

Hospital pharmacies often manage groups of medical items in the form of pharmacy kits. A pharmacy kit can be used, for instance, to provide a group of items for a specific medical procedure, a particular physician, or a designated location of a hospital. As an example, a pharmacy kit can be used to aggregate and transport a collection of medicines for treating a patient with a specific type of stroke, heart condition, or other ailment.

A pharmacy kit (or "kit") typically comprises a group of items specified by a template. For example, the template may specify that the kit requires three vials of adenosine, two containers of albuterol solution, two vials of amiodarone, and so on. The template may also specify ways in which individual items may be satisfied. For example, it may specify that the vials of adenosine may be satisfied by certain product brands. Pharmacy kits are usually stocked by a hospital pharmacy, but they may be stocked by another entity, such as an outsourced kit stocking company.

A kit is typically created by receiving specified items in a pharmacy, manually recording (e.g., on paper and/or electronic records) their product identifiers (e.g., National Drug Code (NDC) or Universal Product Code (UPC)), lot numbers, and expiration dates, and then loading the items into a container, such as a box, tray, or canister. During the kit's lifetime, it may be updated periodically to replace expired or consumed items. These updates are typically performed by inspecting the kit, comparing it to a corresponding template, modifying kit contents as required, and then manually recording any changes.

One challenge that may complicate the management of pharmacy kits is the rise of medication shortages across the country. From normal saline to propofol, any particular item can go into shortage almost inexplicably. As a result, hospitals are often forced to use different sizes or concentrations than what they normally stock or administer. This, unfortunately, may prevent accurate inventory monitoring and disrupt current processes of kit management.

Due to the above and other shortcomings of conventional approaches, there is a general need for improved techniques and technologies for managing pharmacy kits in the face of inventory shortages.

SUMMARY

In one embodiment of the inventive concept, a method of managing a pharmacy kit comprises determining whether a kit stocking contingency has occurred with respect to a segment of the pharmacy kit, as a consequence of determining that the kit stocking contingency has not occurred, determining whether the segment has been satisfactorily stocked according to a first acceptance criterion, and as a consequence of determining that the kit stocking contingency has occurred, determining whether the segment has been satisfactorily stocked according to a second acceptance criterion different from the first acceptance criterion.

In another embodiment of the inventive concept, a method of managing a pharmacy kit using an electronic information processing system comprises defining, in the electronic information processing system, multiple rules for determining whether a segment of a pharmacy kit is satisfactorily stocked, selecting, by the electronic information processing system, at least one rule among the multiple rules according to a kit stocking contingency, and prompting, by the electronic information processing system, a user to stock the segment of the pharmacy kit according to the selected at least one rule.

In one embodiment of the inventive concept, a method of operating an electronic system comprises receiving an input identifying one or more pharmacy items, accessing stored information corresponding to the one or more pharmacy items based on the received input, determining a value of at least one contextual attribute of the one or more pharmacy items based on the accessed information, and selectively executing, blocking, or modifying a workflow to control distribution of the one or more pharmacy items according to the value of the at least one contextual attribute.

In another embodiment of the inventive concept, a system comprises an input capture unit configured to receive an input identifying one or more pharmacy items, a contextual attribute identification unit configured to access stored information corresponding to the one or more pharmacy items based on the received input, and further configured to determine a value of at least one contextual attribute of the one or more pharmacy items based on the accessed information, and a workflow control component configured to selectively execute, block, or modify a workflow to control distribution of the one or more pharmacy items according to the value of the at least one contextual attribute.

BRIEF DESCRIPTION OF THE DRAWINGS

The drawings illustrate selected embodiments of the inventive concept. In the drawings, like reference labels denote like features.

FIG. 4 shows an interface for adding a fill option to a segment of a pharmacy kit according to an embodiment of the inventive concept.

FIG. 5 shows an interface for modifying fill options for a segment of a pharmacy kit according to an embodiment of the inventive concept.

FIG. 6 shows an interface for adding, removing, or modifying fill options for a segment of a pharmacy kit according to an embodiment of the inventive concept.

FIG. 7 shows an interface indicating that an alternate fill option has been used to stock a segment of a pharmacy kit, according to an embodiment of the inventive concept.

FIG. 8 shows an interface with icons indicating that alternate fill options exist for certain segments of a pharmacy kit, according to an embodiment of the inventive concept.

FIG. 9 shows an interface identifying the contents of a segment of a pharmacy kit, together with an indication that alternate fill options were used to stock the segment, according to an embodiment of the inventive concept.

FIG. 10 shows an interface displaying exceptions in a kit with an icon to indicate that missing items can be restocked to match one of multiple rules for a segment, according to an embodiment of the inventive concept.

FIGS. 11A, 11B, and 11C are diagrams illustrating a pharmacy kit according to an embodiment of the inventive concept.

FIGS. 12A and 12B are diagrams of a read station in the system of FIG. 1 according to an embodiment of the inventive concept.

FIG. 19 shows a report generated for a pharmacy kit using the system of FIG. 1 according to an embodiment of the inventive concept.

FIG. 20 shows another report generated for a pharmacy kit using the system of FIG. 1 according to an embodiment of the inventive concept.

FIGS. 22A and 22B show interfaces used to generate and view reports regarding pharmacy kits according to an embodiment of the inventive concept.

FIG. 27 shows a display interface confirming verification of a pharmacy item, according to an embodiment of the inventive concept.

FIG. 28 shows a display interface allowing input to verify a pharmacy item, according to an embodiment of the inventive concept.

FIG. 29 shows a display interface allowing input to verify multiple pharmacy items in batch mode, according to an embodiment of the inventive concept.

FIG. 30 shows a display interface with information used to verify a pharmacy item, according to an embodiment of the inventive concept.

FIG. 31 shows a display interface providing a warning that a scanned pharmacy kit contains unverified items, according to an embodiment of the inventive concept.

DETAILED DESCRIPTION

Figure 1:
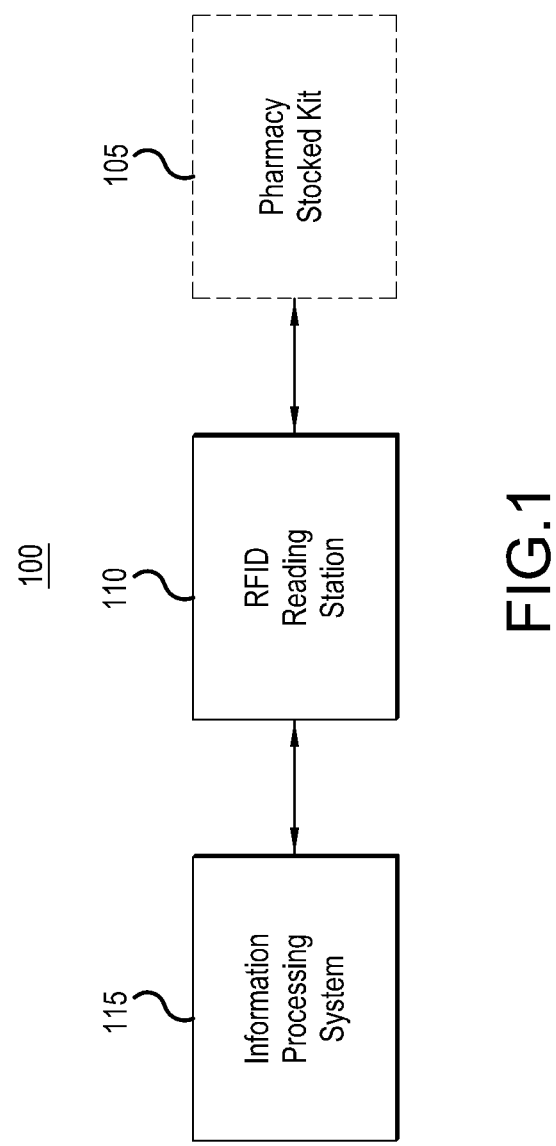
FIG. 1 is a block diagram of a system for managing pharmacy kits according to an embodiment of the inventive concept.

Embodiments of the inventive concept are described below with reference to the accompanying drawings. These embodiments are presented as teaching examples and are not to be construed as limiting the scope of the inventive concept.

The described embodiments relate generally to the management of pharmacy kits. Certain details of pharmacy kits and related methods of management are described in U.S. patent application Ser. No. 13/554,342 filed Jul. 20, 2012, published as U.S. Patent Application Publication No. 2013/0035950, and U.S. patent application Ser. No. 14/126,419 filed Dec. 14, 2013, the respective disclosures of which are hereby incorporated by reference.

In certain embodiments, a kit management system uses RFID technology to label and track the contents of a kit. The use of RFID technology can allow a pharmacy to accurately and efficiently determine whether items in the kit are consumed, missing, expired, or near expiration. These determinations can be used thereafter to verify and update the kit contents, track item usage patterns, generate patient billing information based on item consumption, and so on.

In certain embodiments, a hospital pharmacy begins by tagging items upon bulk receipt in the hospital, or when a kit is stocked. Alternatively, items may arrive at a hospital pre-tagged. One way to tag the items is by scanning bar codes present on most items used in a kit, printing RFID tags based on the scanned bar codes, and then applying the RFID tags to the items. The scanned bar codes typically provide item information such as product identifiers (e.g., NDC or UPC), lot numbers, and expiration dates. This information can be associated with the RFID tags in a computer database to allow subsequent identification and processing by RFID technology. In some embodiments, the RFID tags can be generated automatically when scanning the bar codes, e.g., through the use of an RFID tag printer operatively connected to a bar code scanning machine. Alternatively, the RFID tags may be non-printed tags.

A kit is typically built by placing tagged items in a container such as a box, tray, or canister, and optionally labeling the kit with an RFID tag having information such as a kit identifier, kit type, intended user, or location, for example. These steps are generally performed by a pharmacist or other competent medical professional.

Once a kit is built, its contents are verified by placing it in an RFID reading station, which reads all RFID tags within its sensing range to identify the kit type and any items present. In some embodiments, the RFID reading station includes an enclosure such as a metal box to allow scanning of the kit exclusive of other RFID devices that may be in the surrounding environment. Alternatively, the RFID reading station may omit such an enclosure, for instance, by performing reading in an open area such as table, or using a handheld RFID reader. If the kit has an RFID tag, the kit type can be determined from the tag. Otherwise, it may be inferred from the items present. Items are typically identified by recognizing their RFID tags and then accessing stored information that maps the RFID tags to specific item information.

The stored information may reside on electronic equipment located at the RFID reader station or a remote location such as a remote server, a personal computer (PC), a mobile device, etc. In addition to basic kit and item information, the electronic equipment may also store metadata related to kit processes, such as who built or rebuilt a kit, what items were replaced if the kit was restocked, when the items were inserted in the kit, when verification and update procedures were last performed or will next be performed, and so on.

After the kit and item information are determined by the kit management system, they are analyzed automatically with reference to one or more templates. For instance, a kit template may be located based on the kit type, and then the identified items may be compared with the kit template to determine whether any items are missing or require replacement based on use or expiration. Additionally, the information processing system may analyze item information to determine whether any items are expired or will soon expire. The kit can then be updated based on these analyses.

Kit templates are typically stored in a database within or associated with the information processing system. However, they can alternatively be stored within a memory associated within the RFID reading station or RFID reader, or they can be stored in a separate system accessible by the information processing system.

In general, expiration of an item may occur based on a fixed or variable timeframe. For example, some items may expire at a fixed date indicated by the manufacturer, while other items may expire after a certain amount of time out of the refrigerator, e.g., time of removal+X days. Whether the timeframe is fixed or variable can be indicated in the template at a master level for a particular item, or at a segment level for a segment including the item.

The automatic processing provided by RFID technology and associated electronic equipment allows kit management to be performed with greater efficiency and accuracy compared with conventional approaches. For instance, in some embodiments, kit contents and expiration dates can be validated in 15 seconds or less. Moreover, kit deficiencies can be reported to a pharmacist automatically, allowing them to be addressed in an efficient manner. This reporting can be accomplished, for instance, by an automatically generated charge sheet showing kit contents and expirations.

Once a kit is built and verified, it is ready to be sealed and deployed for use in the hospital. When a kit is used, the seal is broken and items may be removed or consumed. Accordingly, the kit may be subsequently returned to the RFID reading station for additional verification, monitoring, and updates. These additional procedures can be used, for example, to determine whether any items in the kit are missing (e.g., due to use), and whether any items are erroneously present in the kit. This information can then be used to generate a report indicating the status and any necessary updates for the kit, or for other purposes such as patient billing or supply ordering. Once the relevant information is collected, the kit can be rebuilt using the automatically generated report, and then redeployed for another use.

Stored item and kit information can also be used to perform various forms of monitoring and/or reporting related to inventory management. For instance, stored kit information can be analyzed to identify patterns of item consumption. Moreover, the stored information can be inspected to determine the location of kits containing expired items. These and other forms of monitoring and/or reporting can be performed either automatically or in response to user input. For instance, they can be performed according to a predetermined schedule or in response to certain event triggers. Alternatively, a user may simply request monitoring or a report as needed. For example, a pharmacy manager may log in to view consumption logs, usage logs and current inventory to make more informed decisions on which inventory to keep and which kits may require special attention.

The kit management system typically further comprises a user interface and one or more software applications allowing a user to access information regarding the status of kits. As an example, a software application may be used to generate and print a kit charge sheet or charge sheet with the contents and expiration dates of the items and a kit. As other examples, a software application may be used to generate inventory reports showing where kits are dispatched within a hospital, an expiration report indicating dispatched items that are expired or near expiration, consumption and usage reports with traceability to departments, code types, or patients. The kit management system can also comprise or be integrated with a real-time tracking system to maintain current information regarding kit locations. The real-time tracking system typically comprises electronic components associated with the kits and configured to transmit information from the kits to the information processing system to identify the kits' respective locations. Such tracking systems can also be combined with kit management software in order to update the information used to generate inventory reports.

As indicated by the foregoing, a kit management system according to certain embodiments can provide many potential benefits compared with conventional technologies. For example, the kit management system can provide more efficient verification and recording of kit contents, and more accurate monitoring of kits, items, and expiration dates. In certain embodiments, the kit management system may also provide data analysis capabilities for purposes such as patient billing, inventory tracking, and so on.

In certain embodiments described below, a pharmacy kit is managed using multiple acceptance criteria for at least one pharmacy kit segment. The use of multiple acceptance criteria means that a designated segment may be deemed to be satisfactorily stocked with different types, quantities, or concentrations of pharmacy items under different circumstances. For example, if there is a shortage of a pharmacy item typically used to stock the designated segment, one or more different pharmacy items may be accepted as alternatives during the shortage.

The described embodiments may facilitate the use of multiple acceptance criteria by providing an information processing system that allows users to define different rules for determining automatically whether a segment is successfully stocked under different circumstances. Such a definition may include one or more types of items and be associated with one or more operators to suggest how multiple types of items interact with each other. For example, if a designated segment of a pharmacy kit requires three vials of propofol at 20 ml each (e.g., a "first acceptance criterion"), but there was a shortage for that package size, a user could define a rule allowing two 50 ml packages (e.g., a "second acceptance criterion") or two 30 ml packages (e.g., a "third acceptance criterion") as alternative ways of stocking the kit. As another example, an alternate concentration or drug may be used where an alternate size is not available. In that situation, rules may be set to determine which alternate drug or drug combinations would satisfy the requirements of the kit. For instance, if there is no calcium chloride, calcium gluconate may be substituted.

The described embodiments may also allow these rules to be ranked in order of preference to avoid ambiguity of items in a pharmacy kit matching multiple rules at the same time. A pharmacy manager may define preferred rules that cause a system to prompt a user to stock a pharmacy kit in a suggested way. Such rules may be stored in a way that allows a user to query an amount of time that a secondary or tertiary rule is in effect for a particular segment. This information can further be used to suggest optimizations for a pharmacy kit template.

The described embodiments may also be used to generate various types of reports related to the management of pharmacy kits using multiple acceptance criteria. For example, one type of report may identify the most commonly used medications for particular kit segments, enabling a manager greater visibility into medication ordering based on what actually makes it into circulation. Another type of report may provide a history of changes made to kit templates, informing a pharmacy of volatility of certain templates and medication stock. Such a report may be helpful for many management and operational activities such as ordering drug inventory, for instance. Yet another type of report may be an inventory list (or "charge sheet") with specific billing codes. Such a report may show one of several billing codes for a segment depending on which acceptance criterion or stocking rule was used to stock the segment.

In certain embodiments, a system may also suggest a pharmacy kit configuration based on available inventory. For example, if a pharmacy kit allows for two different sizes of the same medication in a segment, and one size is on shortage, the system could guide a user to increase the medication in the segment based on the size that is not on shortage.

These and other embodiments may provide pharmacy managers with greater flexibly to handle situations related to shortages of pharmacy items, which may in turn increase efficiency in a hospital pharmacy. They may also increase safety by making kit processing more robust in the face of periodic variances in pharmaceutical inventory.

FIG. 1 is a block diagram of a system for managing pharmacy kits according to an embodiment of the inventive concept.

Referring to FIG. 1, system 100 comprises an information processing system 115 and an RFID reading station 110. System 100 is configured to automatically read and process information from a pharmacy kit 105. This allows relatively efficient monitoring and updating of the kit's contents.

RFID reading station 110 comprises an RFID reader configured to read RFID tags located on kit 105. During a typical read operation, the RFD reader interrogates RFID tags associated with respective items in kit 105, and it also interrogates any RFID tag associated with kit 105. As a consequence of the interrogation, the RFID reader receives information identifying each tag, and it conveys the information to information processing system 115. Based on the tag information, information processing system 115 identifies kit 105 and the items present. This can be accomplished, for instance, by relating the tag information to item or kit information stored in a computer database.

Once the kit and items are identified, information processing system 115 may process corresponding information in various ways, for example, by displaying it to a user, generating reports indicating missing or expired items, performing patient billing procedures based on any consumed items, or merely storing it for subsequent analysis. In certain embodiments, the kit and item information is managed as a list. For example, it can be stored and accessed in the form of a list in a computer database or other storage medium.

One of the most common ways of processing information captured from a kit is comparing the captured information with a template of the kit to determine whether the kit is satisfactorily stocked. The template of a kit defines items that are required to be placed in the kit. The template typically defines a plurality of item segments (or "segments") to be included in the kit, where each item segment corresponds to a class or type of items and/or additional segments to be included in specific quantities. For instance, an item segment may define a specific class of medications, such as ibuprofen, acetaminophen, adenosine, or albuterol. Where a segment includes one or more additional segments, the template is considered to have multiple segment "levels". In general, a template can have an arbitrary number of segment levels. An example of a template having multiple segment levels would be one containing a segment "analgesic", with the item "morphine" and a sub-segment "ibuprofen" containing items "Advil" and "Generic".

A segment of a kit is deemed to be satisfactorily stocked if the kit includes all of the items specified by at least one acceptance criterion associated with that segment. The term "acceptance criterion" here denotes a set of one or more rules that determines items that can be accepted (or required) as fulfilling the requirements for a particular segment under specified circumstances. For instance, one rule may define a "first acceptance criterion" that accepts a first type of medication to stock the segment under normal circumstances, and another rule may define a "second acceptance criterion" that accepts a second type of medication to be stocked in the segment where there is a shortage of the first type of medication. In other words, different rules may govern how a segment can be satisfactorily stocked under normal or shortage conditions. In general, the items that may be used to satisfactorily stock a segment may be, e.g., medications of different types (e.g., brands, formulations, etc.), concentrations, quantities, etc. These items are generally identifiable by distinct NDC or UPC identifiers. Circumstances that trigger the use of a different acceptance criteria are referred to as kit stocking contingencies. A shortage of items is one common example of a kit stocking contingency, but other contingencies are possible.

System 100 may occasionally aggregate last known status information for each kit that has been read, and it may then determine whether any action is required to resolve expiration issues, missing item issues, or extra item issues in all of the kits in a hospital or other facility. These actions can be performed, for example, on a periodic basis, in response to particular events, or in response to a user request.

System 100 may occasionally aggregate last known status information for each kit that has been read, and it may then determine whether any action is required to resolve expiration issues, missing item issues, or extra item issues in all of the kits in a hospital or other facility. These actions can be performed, for example, on a periodic basis, in response to particular events, or in response to a user request.

In addition to storing current or most recent information regarding kits, system 100 may also store a virtual history for each kit. Such a virtual history may include, for example, a record of each transaction involving the kit since the time it was tagged. Such transactions may include, for example, scans, database queries, updates such as restocking or removal of items, the occurrence of kit stocking contingencies and the use of alternative acceptance criteria when stocking segments, and so on. The virtual history may be maintained by information processing system 115, for example, and it may be output in the form of a report in response to a user request. In addition, the virtual history may be used to gather data or statistics that may be useful for planning future tasks such as kit updates, item restocking, and so on.

Kit 105 can be associated to a location or responsible person, such as a physician. This association can then be stored in system 100, and it can be used to quickly determine the location of kit 105 after deployment. The location of kit 105 can also be determined and/or updated by associating its RFID tag with a real time location system. In addition, kit 105 may be associated with a patient identifier or billing identifier and any missing items may be marked as being consumed by that billing or patient identifier. Such billing information may be stored either in system 100, in a separate system or in both system 100 and a separate system. System 100 may retrieve or update some or all of the billing information when a kit is read and items may or may not be consumed.

Where kit 105 contains prescription pharmaceuticals, the facility may be required to comply with requirements set by a state board of pharmacy. The precise regulations may vary from state to state, but can include requirements such as a mandatory visual inspection of kit 105 prior to deployment, or an item-by-item determination of each item type, lot number and expiration date. Other board of pharmacy requirements may include documentation to be included in kit 105 to verify completeness and accuracy of expiration data or a label on the outside of kit 105 to indicate the last check of the kit and the next expiring item in the kit.

In some embodiments, system 100 is configured to store relevant board of pharmacy requirements and verify that each step has been completed. System 100 can also be configured to compute steps automatically where allowed by regulations. Such steps may include, for example, printing documentation or labels, reading tags and verifying items, or requesting confirmation that a manual step has been completed. As these steps are completed, system 100 may record the name of the person who performed the steps. It may also confirm whether the person is authorized to perform the steps. In general, information regarding these and other steps can be recorded in system 100 using a log, database, or other storage format.

Although FIG. 1 shows RFID reading station 110 and information processing system 115 as separate features, they are not required to be physically or functionally separate. For instance, information processing features could be integrated with parts of RFID reading station 110, such as an RFID reader. In general, the physical and functional implementation of system 100 can be partitioned arbitrarily between various forms of hardware, software, firmware, etc., as will be recognized by those skilled in the art.

In addition, the physical and functional implementation of system 100 can be distributed arbitrarily across multiple devices, systems, or network components. For example, in some embodiments, information processing system 115 may include or be integrated with wireless mobile devices in order to convey information remotely. One potential use of such a configuration would be to transmit kit notifications to remote users via push email or SMS text messaging, or subscription based data feeds. Such notifications could be used, for instance, to alert users that an updated kit is available, that a kit should be returned to the pharmacy, that a checked-out kit requires updates due to item expiration, and so on. Another potential reason to integrate information processing system 115 with remote components is to receive updates of kit templates and item master data. For example, some or all of a kit template or item master data may be received from an external system. The received item master data could indicate, for example, that an item has been recalled or changed in some material respect.

Figure 2:
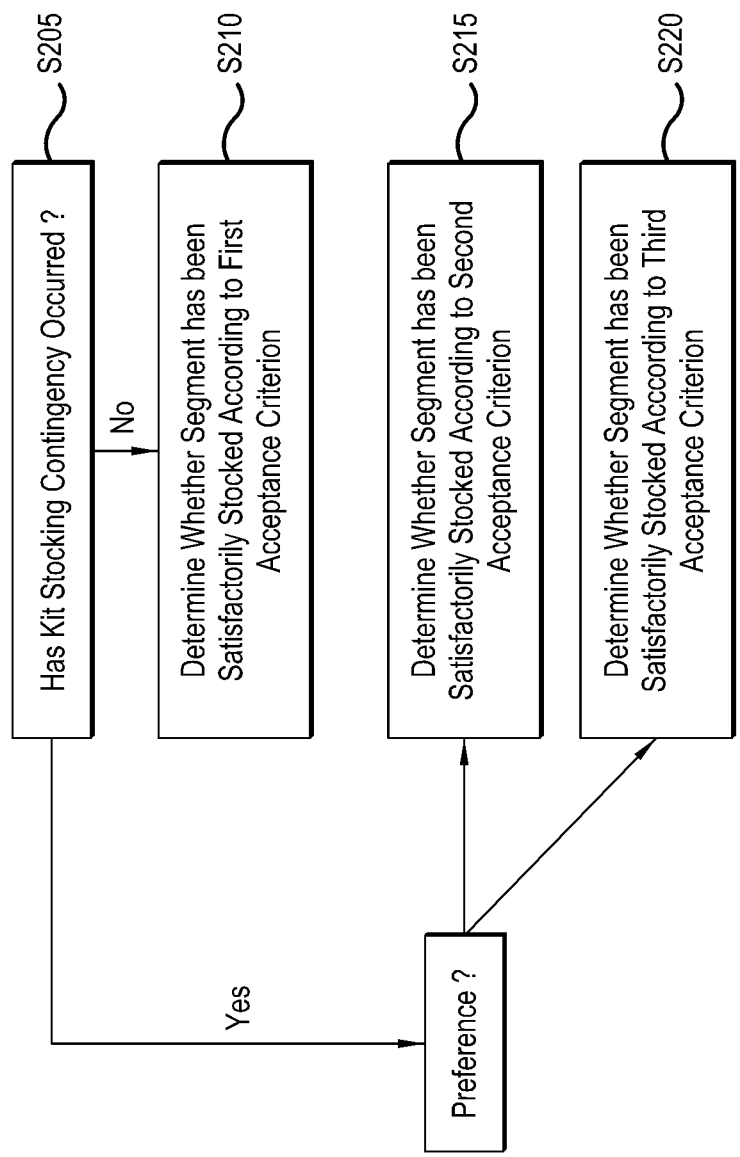
FIG. 2 is a flowchart illustrating a method of managing pharmacy kits according to an embodiment of the inventive concept.

FIG. 2 is a flowchart illustrating a method of managing pharmacy kits according to an embodiment of the inventive concept. The method of FIG. 2 is typically used to verify that a kit has been successfully stocked.

Referring to FIG. 2, the method comprises determining whether a kit stocking contingency has occurred with respect to a segment of the pharmacy kit (S205). The kit stocking contingency may be, for instance, a shortage of at least one pharmacy item corresponding to the first acceptance criterion. In general, a shortage may occur where there is inadequate supply of the at least one pharmacy item to meet current needs or expected needs of a medical facility served by a pharmacy. Determining that a kit stocking contingency has occurred may comprise, for instance, receiving a shortage notification for the at least one pharmacy item corresponding to the first acceptance criterion. Alternatively, it may comprise examining an inventory level and detecting a shortage where the inventory level falls below a defined threshold.

The method further comprises, as a consequence of determining that the kit stocking contingency has not occurred (S205=No), determining whether the segment has been satisfactorily stocked according to a first acceptance criterion (S210). This can be accomplished, for instance, by evaluating kit related information captured by a system such as that illustrated in FIG. 1. The evaluation may include, e.g., comparing the information with a list of required pharmacy items specified by a template under the first acceptance criterion, or comparing the information against one or more rules defined according to the first acceptance criterion.

The method still further comprises, as a consequence of determining that the kit stocking contingency has occurred (S205=Yes), determining whether the segment has been satisfactorily stocked according to a second or third acceptance criterion different from the first acceptance criterion (S215 or S220). In other words, where a kit stocking contingency arises, the method may use a different criterion to determine whether the segment is satisfactorily stocked. As illustrated by a box labeled "Preference?", the second or third criterion may be selected according to a user preference (or hierarchical ranking), which may be defined within a particular implementation of the method.

The first through third acceptance criteria may specify, for instance, different types, sizes, or concentrations of items (e.g., medications) that can be used to stock the segment. The different types of items may also be associated with different operators (e.g., different authorized professionals), such that where a kit is being stocked by one type of operator, the first through third acceptance criteria may be satisfied by a first type of pharmacy item, and where the kit is being stocked by another type of operator, the first through third acceptance criteria may be satisfied by a second type of pharmacy item different from the first type of pharmacy item.

The method may further comprise determining whether an additional kit stocking contingency has occurred, and as a consequence of determining that the additional kit stocking contingency has occurred, determining whether the segment of the pharmacy kit has been satisfactorily stocked according to one or more additional acceptance criterion different from the first and acceptance criteria. In other words, the method may be extended to use not only secondary acceptance criteria, but also tertiary acceptance criteria, and so on. In general, where multiple acceptance criteria are used under different circumstances, those additional acceptance criterion can be ranked in order of user preference. Moreover, those rankings may differ according to the user who is performing a stocking or kit checking procedure.

The method may still further comprise operations allowing a user to define the rules for determining whether a segment is satisfactory stocked. For instance, the method may comprise receiving a user input to define one or more such rules for the first criterion or the second criterion.

Figure 3:
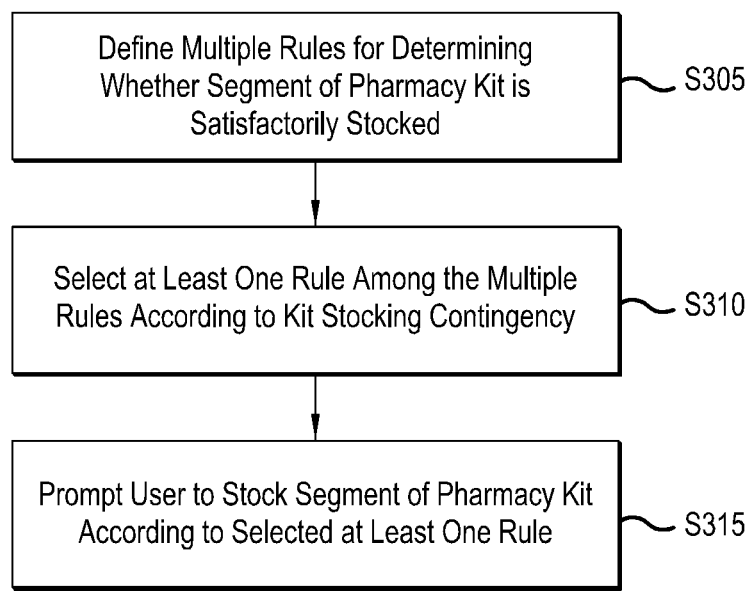
FIG. 3 is a flowchart illustrating a method of managing pharmacy kits according to another embodiment of the inventive concept.

FIG. 3 is a flowchart illustrating a method of managing pharmacy kits according to another embodiment of the inventive concept. The method of FIG. 3 is typically used to ensure proper stocking of a pharmacy kit.

Referring to FIG. 3, the method comprises defining, in an electronic information processing system (e.g., system 100), multiple rules for determining whether a segment of a pharmacy kit is satisfactorily stocked (S305). As an example, one rule may require that the segment be stocked with a first type, size, quantity, or concentration of a medical item when there is no shortage of that item, and another rule may require that the segment be stocked with something other than the first type, size, quantity, or concentration where there is a shortage.

The method further comprises selecting, by the electronic information processing system, at least one rule among the multiple rules according to a kit stocking contingency (S310). This selection is typically performed automatically when there is a shortage or other kit stocking contingency. It may be initiated, for instance, in response to reception of an automated shortage notification, in response to user input indicating a shortage, or in response to an inventory level falling below a defined threshold. Additionally, the multiple rules may be ranked in order of user preference and selected according to the ranking.

The method still further comprises prompting, by the electronic information processing system, a user to stock the segment of the pharmacy kit according to the selected at least one rule. (S315). For instance, the system may display an interface instructing the user to stock the segment with a particular type, size, concentration, or quantity of a pharmacy item. The system may then allow the user to rescan the kit to confirm proper stocking of the segment.

The methods of FIGS. 2 and 3 may each further comprise generating various types of reports or otherwise providing information to a user based on the use of alternative acceptance criteria or rules. The reports or other information may be generated or provided either automatically or in response to a user query. For instance, system 100 may receive a query from a user requesting an amount of time for which a selected rule is to be in effect and then display the requested amount of time to the user. This information may be a useful indicator of the duration of an item shortage, for instance. As other examples, the method may generate a report indicating relative quantities of pharmacy items used to stock the segment according to the multiple rules, a report indicating a history of changes made to a template of the pharmacy kit, or a charge sheet comprising billing information for pharmaceutical items corresponding to the selected at least one rule.

FIGS. 4 through 10 show various examples of interfaces that may be used to present and/or receive information from a user during the methods described above with reference to FIGS. 2 and 3. Such interfaces may be used in conjunction with a system such as that illustrated in FIG. 1, for example.

FIG. 4 shows an interface 400 for adding a fill option to a segment of a pharmacy kit according to an embodiment of the inventive concept. A fill option specifies one or more pharmacy items that can be used to satisfactorily stock the segment under designated circumstances. In other words, it corresponds to a rule for stocking the segment with the pharmacy items.

Referring to FIG. 4, interface 400 comprises fields allowing a user to enter information identifying a formulary item, including an NDC, manufacturer, item name, strength, and package size. It further comprises a field allowing the user to enter a segment that may be filled by the formulary item, and a field allowing the user to designate a rule for using the formulary item within the segment, namely a rule designating the formulary item as a "preferred fill option" or as an "alternate fill option". The preferred fill option status may be used, for instance, where the designated formulary item is to be included in a kit under default circumstances, and the alternate fill option status may be used, for instance, where the designated formulary item is to be included in a kit because of a shortage.

FIG. 5 shows an interface 500 for modifying fill options for a segment of a pharmacy kit according to an embodiment of the inventive concept.

Referring to FIG. 5, interface 500 comprises fields allowing a user to add or remove fill options to a segment, to specify the quantity associated with a fill option, or to set a billing code for a fill option. In the illustrated example, a user has searched for possible new fill options by entering the search term "epi" into a search field. As a result, the interface has displayed various search results that include the entered term. A user can include any of those search results as a fill option by clicking on "+Add". In the illustrated example, three fill options have already been added to the segment. Any of those fill options can be removed by clicking on "x Remove". Moreover, one of those options has been selected, as indicated by shading. The quantity and billing code at the top of interface 500 correspond to the selected fill option.

FIG. 6 shows an interface 600 for adding, removing, or modifying fill options for a segment of a pharmacy kit according to an embodiment of the inventive concept.

Referring to FIG. 6, interface 600 shows a segment that belongs to a general operating room (OR) kit. The segment is specified by entering or selecting a segment name in a field near the top of interface 600. In the illustrated example, the segment has two preferred fill options and three alternate fill options. The preferred and alternate fill options can be added, removed, or modified by clicking on appropriate portions of interface 600. The entire segment can be deleted by clicking "Delete Segment" at the bottom of interface.

FIG. 7 shows an interface 700 indicating that an alternate fill option has been used to stock a segment of a pharmacy kit, according to an embodiment of the inventive concept.

Referring to FIG. 7, interface 700 shows a partial summary of items included in various segments of a kit that has been scanned. In the summary of a segment "Ampicillin 1g", an icon indicates that a non-preferred fill option was used to stock the kit. This may indicate, for example, that the preferred fill option was on shortage.

FIG. 8 shows an interface 800 with icons indicating that alternate fill options exist for certain segments of a pharmacy kit, according to an embodiment of the inventive concept.

Referring to FIG. 8, interface 800 comprises a field that allows a user to select a kit master, which specifies the segments and corresponding items for a kit. In the illustrated example, the selected kit master is for an "Anesthesia C-section Tray" kit. Interface 800 further comprises a field displaying each of the segments of the selected kit master, with icons next to segments having multiple fill options. For instance, an icon to the left of the name label on a segment "Diphenhydramine 50 mg/ml vial" indicates that there is more than one fill option for this segment. For each of the segments, interface 800 displays the name of a primary fill option, and it also provides an option to hide or show alternative fill options for the segments with multiple fill options.

FIG. 9 shows an interface 900 identifying the contents of a segment of a pharmacy kit, together with an indication that alternate fill options were used to stock the segment, according to an embodiment of the inventive concept.

Referring to FIG. 9, interface 900 may be displayed to a user after the kit is scanned. It contains an icon below the segment name "Amiodarone inj 150 mg/3 ml" to indicate that at least one of the scanned items matches a non-preferred fill option for this segment.

FIG. 10 shows an interface 1000 displaying exceptions in a kit with an icon to indicate that missing items can be restocked to match one of multiple rules for a segment, according to an embodiment of the inventive concept.

Referring to FIG. 10, interface 1000 may be displayed after a kit is scanned. It displays exceptions in the scanned kit, which are features or occurrences that are deemed to require user notification. In the illustrated example, the exceptions include items that will expire soon, missing items, extra items, and wrong items. Next to the missing items, interface 1000 includes an icon indicating that multiple fill options are available. It also includes an indication of an expected quantity of those items (e.g., an amount that may be needed to fill expected demand), an actual quantity of those items in inventory, and a shortage, which is defined as a difference between the expected and actual quantities. This information may assist a user in taking appropriate action, such as either stocking the missing items using a primary fill option in the event that there is adequate supply, or stocking the missing items using an alternate fill option in the event that there is a shortage.

Figure 11A:
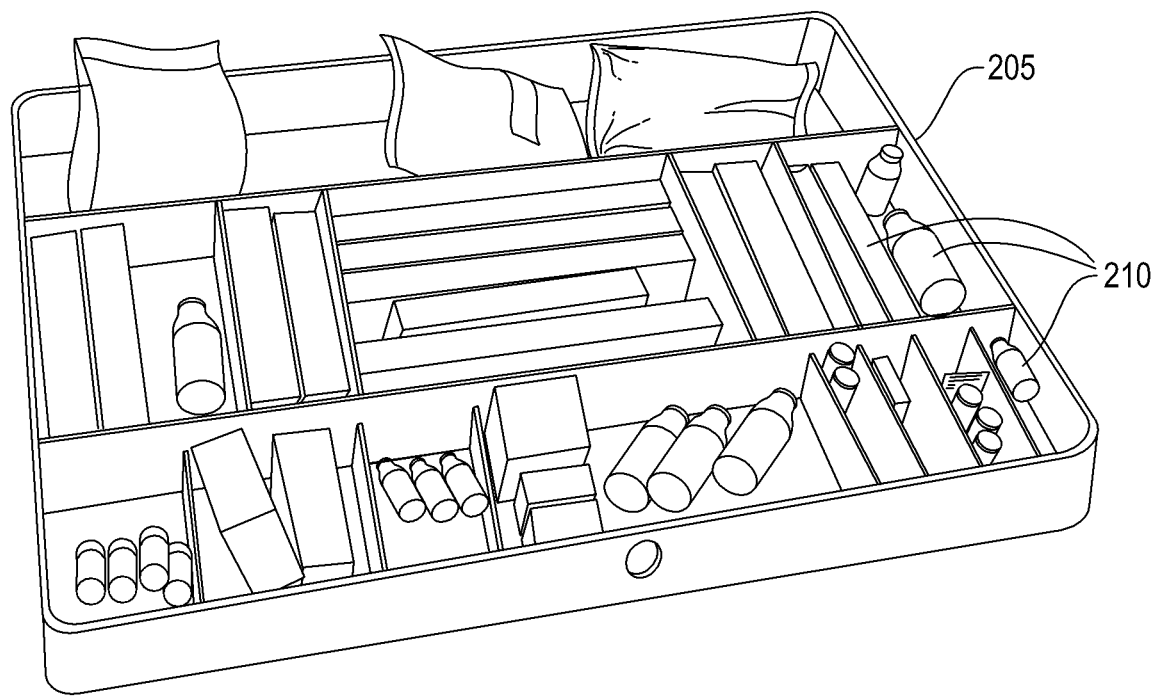

FIGS. 11A through 11C are diagrams illustrating a pharmacy kit according to an embodiment of the inventive concept. In particular, FIG. 11A shows an example of a kit tray comprising multiple items having RFID tags, FIG. 11B shows an example of a partial template associated with the kit, and FIG. 11C shows an example of a partial kit record for the kit. The kit of FIGS. 11A through 11C represents one example of pharmacy kit 105 shown in FIG. 1.

Referring to FIG. 1A, kit 105 comprises a container 205 and items 210. Container 205 is shown as a tray in FIG. 1A, but this is merely one example of a container that can be used to carry items 210. Alternative examples include boxes, canisters, bags, coolers, and various others. Although not shown in FIG. 11A, kit 105 could further comprise a cover, such as a lid, that can be used to enclose items 210 prior to deployment. Additionally, the cover can be sealed onto container 205 to prevent tampering between deployment and use of kit 105. In general, where kit 105 is susceptible to opening or closing (e.g., where it has a lid or other covering), it can be read in an open configuration or a closed configuration.

Items 210 typically include medicines or other medical supplies that may be stocked by a pharmacy. As shown in FIG. 11A, items 210 can have various different forms of packaging. For example, they can be packaged in vials, bags, boxes, bottles, and other forms. These different forms of packaging may also comprise different materials, such as glass, plastic, paper, cardboard, foam, or metal.

Due to the different types of packaging and materials, items 210 may be tagged with RFID tags having different shapes or types. As one example, RFID tags placed on metal bags may be subject to electromagnetic interference (EMI) from the metal. Accordingly, to prevent EMI, RFID tags connected to metal bags may have a foam backing or other form of insulation to create separation from the bags. Such tags may be referred to as metal-mount tags. As another example, RFID tags attached to small vials or bottles may potentially occlude label information on the vials. Accordingly, to prevent occlusion, RFID tags having a transparent adhesive portion may be attached to vials, bottles, or other types of packages. Such tags may be referred to as transparent tags.

Kit 105 is typically built by manually placing items 210 in container 205. This is typically accomplished by a pharmacist or other competent medical professional after items 210 have been labeled with RFID tags and stocked in the pharmacy. For example, a pharmacist may visit pharmacy shelves to collect items 210 and place them in container 205.

Referring to FIG. 11B, an example template defines items to be placed in kit 105. More specifically, the template defines a plurality of item segments (or "segments") to be included in kit 105, where each item segment corresponds to a class or type of items and/or additional segments to be included in specific quantities. For instance, an item segment may define a specific class of medications, such as ibuprofen, acetaminophen, adenosine, or albuterol. Where a segment includes one or more additional segments, the template is considered to have multiple segment "levels". In general, a template can have an arbitrary number of segment levels. An example of a template having multiple segment levels would be one containing a segment "analgesic", with the item "morphine" and a sub-segment "ibuprofen" containing items "Advil" and "Generic".

For simplicity, FIG. 11B shows example segments in generic form, i.e., "medicine bottle 1", "medicine vial 2", etc. The segment "medicine bottle 1", for example, indicates that kit 105 is to include one or more bottles of a first type of medicine (e.g., a bottle of ibuprofen). Similarly, the segment "medicine vial 2" indicates that kit 105 is to include one or more vials of a second type of medicine (e.g., a vial of adenosine), and so on. Although each segment in FIG. 11B is associated with a particular type of packaging, such as a bottle, vial, or bag, segments are not necessarily limited by package type. For instance, a segment could be defined more broadly based on medicine type alone.

The template further defines a set of permissible items that can be used to satisfy each segment. The permissible items may correspond to different brands or other forms of each item corresponding to the segment. These items are generally identifiable by distinct NDC or UPC identifiers. As an example, a segment defined as a "bottle of ibuprofen" may be satisfied by a either a bottle of Advil or a bottle of generic ibuprofen. For simplicity, FIG. 11B shows the items associated with each segment in generic form, i.e., "product A", "product B", etc. Accordingly, the segment "medicine bottle 1" may be satisfied by two different products "A" and "B", the segment "medicine vial 2" may be satisfied by three different products "C", "D", and "E", and so on.

The template still further defines a quantity of items to be included in kit 105 for each segment. For example, based on the template of FIG. 11B, kit 105 is to include one item corresponding to "medicine bottle 1" (e.g., one bottle of ibuprofen), three items corresponding to "medicine vial 2", two items corresponding to "medicine bag 3", and so on. As a more concrete example, a segment "Pain Medication" could have permissible items "Tylenol" or "Advil", with a quantity of two, which could be satisfied by two bottles of Tylenol, two bottles of Advil, or one of each, for instance.

In general, the quantity can be zero or more. Where the quantity is greater than one, each item of a particular segment can be satisfied by any combination of the permissible items for that segment. For example, if there are three permissible items and the required quantity is three, the requirement may be satisfied by three of the same permissible item, one of each, etc. For instance, some kits may allow the stock of adenosine vials to be satisfied by different product brands. Alternatively, the template may require that multiple instances of the same item be selected, or that only certain combinations of items are permitted. Moreover, the template may include restrictions on the items that can be included in combination from among different segments.

Although the template determines the contents to be included in the kit under most circumstances, there are occasions where deviation from the template will be permitted. One of these occasions is a national shortage of one or more items to be included in the kit. When there is a national shortage of a particular item, certain substitutions or omissions of the item may be allowed. For example, if sodium bicarbonate is on national shortage, a kit may be permitted to include a suitable substitute for sodium bicarbonate, or it may be permitted to be deployed without sodium bicarbonate or any substitute.

The procedure for managing items under shortage may be defined in a variety of ways. For example, allowable substitutes for national shortage conditions may be embedded in the template itself and then triggered by information processing system 115 when a shortage arises. As an alternative example, information processing system 115 may simply ignore certain restrictions in a template when a shortage arises.

Referring to FIG. 11C, a kit record comprises information regarding the contents of a kit that has been built in a pharmacy and verified through the use of RFID reading station 110. In the example of FIG. 11C, the information comprises the name of each segment in the kit, and specific details of each item in each segment. The specific item details include a brand name, an item name, an NDC identifier, a lot number, medicine strength or concentration, and an expiration date. The item details may further include information indicating whether an item has a fixed expiration date or one that varies based on time away from a refrigerator. Where the item has a variable expiration date, the item details may indicate whether the item has been removed from the refrigerator, and if so, at what time or date.

The kit record is typically generated by RFID reading station 110 or information processing system 115 upon verifying or re-verifying the kit. It can then be compared to a corresponding template to determine whether the kit has missing or expired items, or it can be stored in information processing system 115 for subsequent comparisons, updates, or analyses.

Figure 12A:
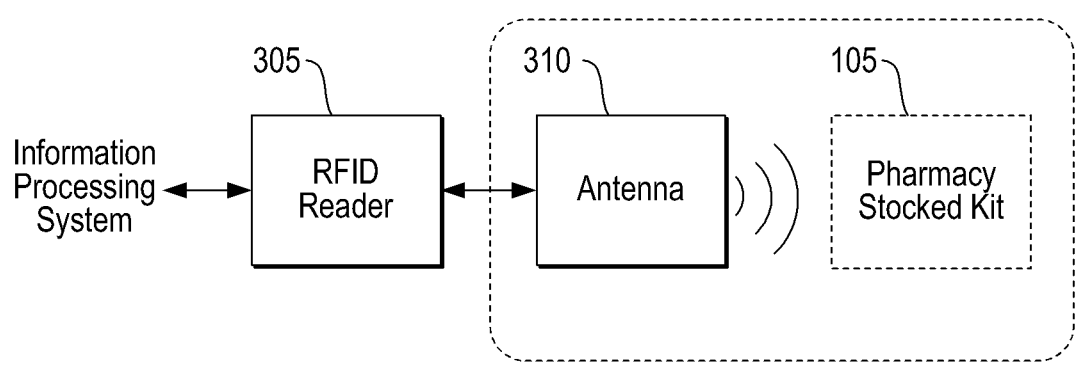

FIGS. 12A and 12B are diagrams of RFID reading station 110 of FIG. 1 according to an embodiment of the inventive concept. In particular, FIG. 12A is a block diagram illustrating electronic equipment associated with RFID reading station 110 according to an example embodiment, and FIG. 12B is a schematic diagram of a container configured to receive kit 105 during a read operation of RFID reading station 110.

Referring to FIG. 12A, RFID reading station 110 comprises an RFID reader 305 and an antenna 310. Antenna 310 is located within a container 315 designed to receive kit 105 during a read operation. RFID reader 305 controls antenna 310 to communicate with RFID tags associated with items of kit 105, as well as any RFID tag associated with the kit itself. In addition, RFID reader 305 receives and processes communications received by antenna 310 from kit 105. Although RFID reader 305 is shown outside of container 315, it could alternatively be included within container 315. Moreover, although RFID reader 305 and antenna 310 are shown as two separate components, they could alternatively be integrated into a single component or divided into additional components.

In a typical read operation, RFID reader 305 controls antenna 310 to interrogate any RFID tags within container 315. In response to the interrogation, the RFID tags communicate information to RFID reader 305 via antenna 310. The communicated information is typically associated with corresponding information stored in a database, such as NDC identifiers, lot numbers, and expiration dates for individual items, and a kit identifier for the kit as a whole. RFID reader 305 communicates the received information to information processing system 115 for storage and/or comparison with a template.

Referring to FIG. 12B, container 315 comprises an enclosed space for receiving kit 105. The left side of FIG. 12B shows container 315 with doors opened to receive kit 105, and the right side of FIG. 12B shows container 315 with doors closed to perform a read operation. The use of an enclosed space to allows RFID tags to be read without interference from objects in the surrounding environment, such as false positives from RFID tags on items not belonging to kit 105. Accordingly, container 315 may be formed of a material designed to provide electromagnetic shielding, such as a metal box.

In some embodiments, RFID reading station 110 is restricted to receiving only one kit at a time. This restriction may be imposed in a variety of ways, for instance, by configuring an enclosure to accommodate only one kit container or interrogating kit tags prior to scanning to ensure that no more than one kit tag is present. In certain alternative embodiments, RFID reading station 110 may be specifically configured to allow concurrent scanning of multiple kits. For example, two kits could be placed in RFID reading station 110, scanned concurrently, and then assigned to a common location or person, such as a particular cart, room, physician, etc. Moreover, such a common assignment may be recorded in information processing system 115 to allow joint analysis or tracking of more than one kit.

Figure 13:
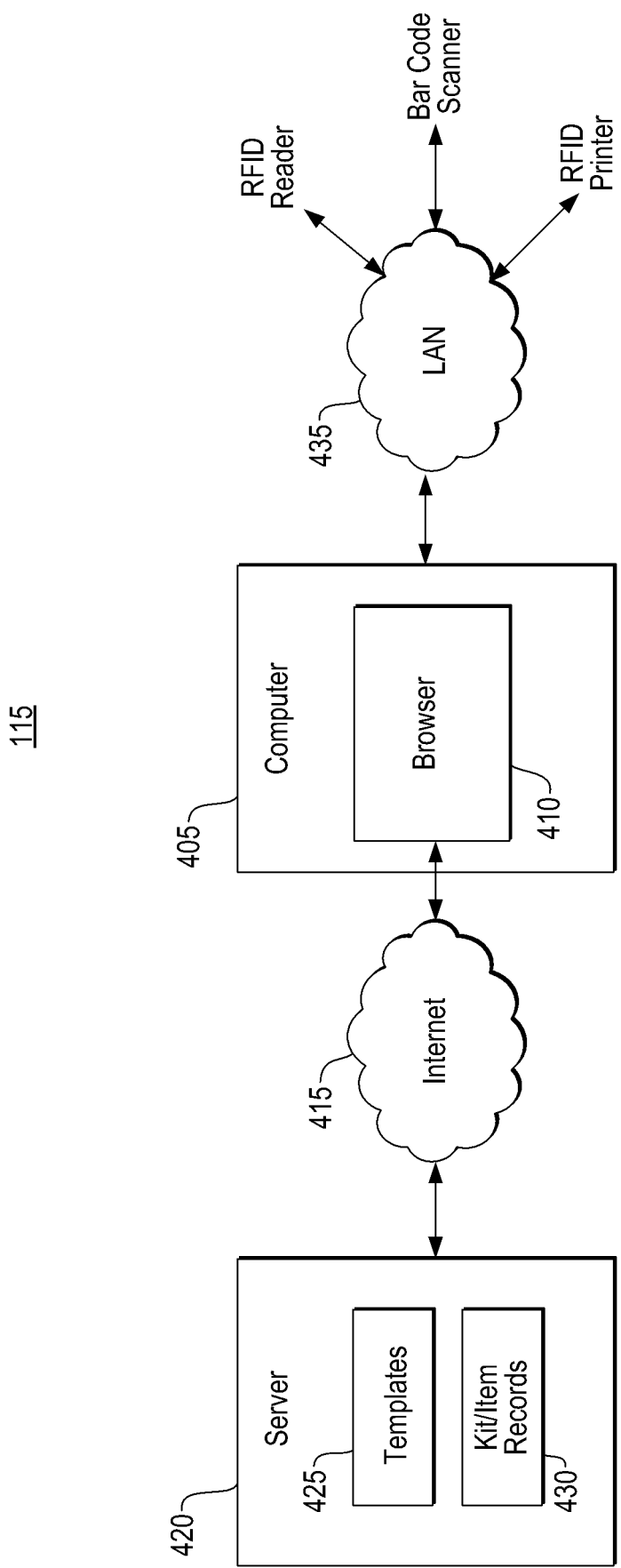
FIG. 13 is a diagram of an information processing system in the system of FIG. 1 according to an embodiment of the inventive concept.

FIG. 13 is a diagram of information processing system 115 according to an embodiment of the inventive concept. In the embodiment of FIG. 13, various features of information processing system 115 are connected in a networked configuration. However, in alternative embodiments these components could be in alternative configurations, e.g., with components directly connected, physically integrated, or functionally partitioned in other ways.

Referring to FIG. 13, information processing system 115 comprises a computer 405 and a server 420. Computer 405 and server 420 are connected to each other via the internet 415, and computer 405 is connected to an RFID reader, a bar code reader, and an RFID printer through a local area network (LAN) 435.

Computer 405 comprises a browser 410 that receives kit information from the RFID reader via LAN 435 and communicates with server 420 through the internet 415. Server 420 stores templates 425, which typically include kit master templates and item master templates. Server 420 also stores records 430, which include information regarding individual kits and items.

Although server 420 is shown as a single unit in FIG. 13, it may comprise more than one device, such as multiple local and/or central computers. In addition, although server 420 is shown to be connected with a single computer, it may be connected to additional or alternative devices, such as other local computers, mobile devices, and so on. Moreover, although server 420 is shown to receive information from a single RFID reader, it could also receive information from other RFID readers. For example, information processing system could be connected to multiple RFID reading stations through the internet 415.

The RFID printer can be used to print RFID tags automatically when a kit is being built or updated. For example, an RFID tag can be printed for a new item by scanning the item's bar code using a bar code scanner connected to computer 405, accessing server 420 to associate a particular RFID tag with the item, and then printing the RFID tag.

Figure 14:
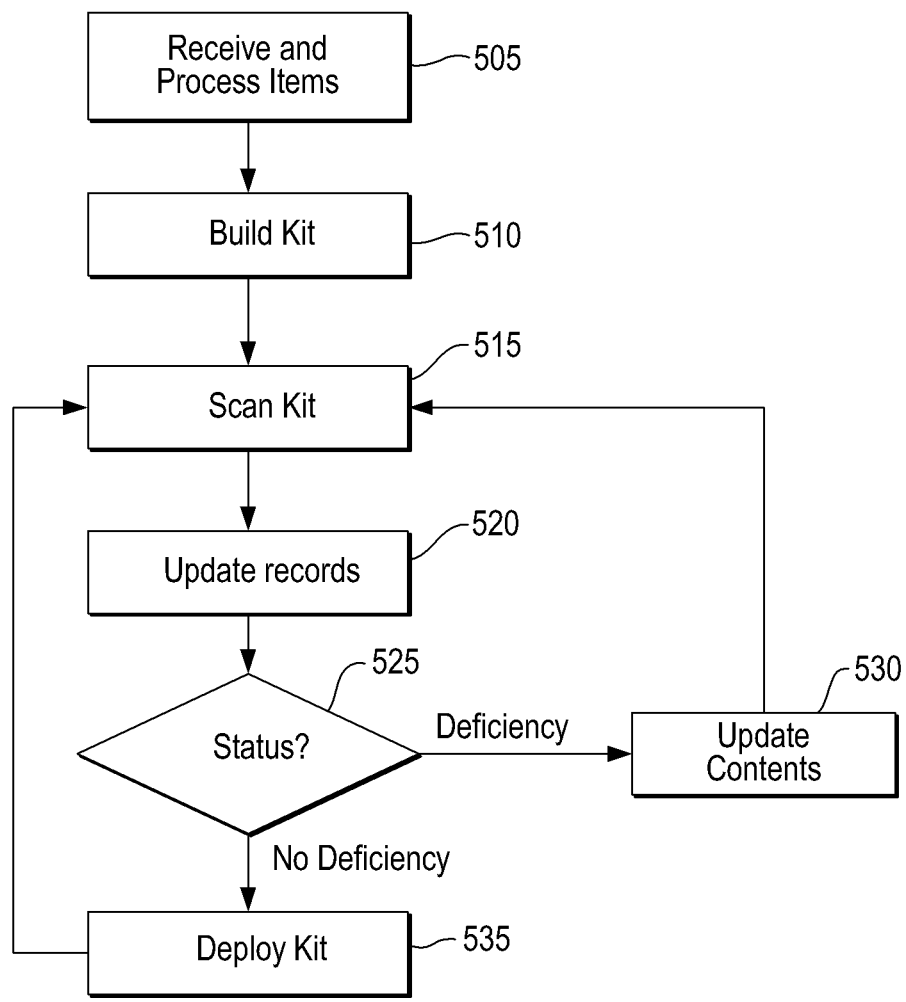
FIG. 14 is a flowchart illustrating a method of managing pharmacy kits according to an embodiment of the inventive concept.

FIG. 14 is a flowchart illustrating a method of managing pharmacy kits according to an embodiment of the inventive concept. The method of FIG. 14 is typically performed by a pharmacist or other medical professional associated with a hospital pharmacy. For explanation purposes, it will be assumed that the method of FIG. 14 is performed using system 100 of FIG. 1. However, the method is not limited to a particular system. In the description that follows, example method steps will be indicated by parentheses (XXX) to distinguish them from device or system components.

Referring to FIG. 14, the method begins with a pharmacy receiving and processing kit items (505). The items typically arrive in bulk at the pharmacy and are processed by tagging them with RFID tags and recording them in an inventory system. Next, a kit is built from tagged items in the pharmacy inventory (510), and the kit is scanned using RFID reading station 110 (515). The scan detects RFID tags of kit items and the kit itself and transmits corresponding information to information processing system 115.

Information processing system 115 updates stored records to reflect the scanning (520). In the update, a database in information processing system 115 is updated to reflect the scanned kit contents. For example, the database may be updated to reflect the presence of any new or replaced items, along with their expiration dates. The database may also be updated with other information, such as the name of the person who last modified the kit contents, a location to which the kit is to be deployed, a patient to be billed for consumption of kit items, and so on.

Based on the updated records, information processing system 115 performs a status check to verify the contents of the kit (525). The status check typically involves forming a list of items based on the transmitted information or updated records and comparing the list against a kit template. It may also involve comparing the updated kit information against information obtained in prior scans, or evaluating the kit information in light of certain business rules, such as billing protocols.

If the status check indicates a deficiency in the kit (525="Deficiency"), such as missing or expired items, the kit contents are updated (530), and the method returns to step 515 where the kit is re-scanned. The update can be performed, for example, by replacing any expired items or inserting missing items. Otherwise, if the status check indicates no deficiency in the kit (525="No Deficiency"), the kit is deployed for use in the hospital or other facility served by the pharmacy (535).

The updating of records and status check are typically performed any time the kit is scanned, as indicated by the flow of FIG. 14. This can take place under a variety of circumstances, such as when a kit is first built and verified, when the kit is checked-in to the pharmacy for storage, or when the kit is checked-out of the pharmacy for use.

Deployment of the kit may involve, for example, transporting it to a specific location of the hospital, checking it out to a particular individual, or merely storing it within the pharmacy. Following deployment, steps 515 through 535 may be repeated any number of times as needed. For example, the kit may be re-scanned and updated following each use or it may be periodically updated at specified times, such as daily, weekly, or whenever an expired item is noted in information processing system 115.

Figure 15:
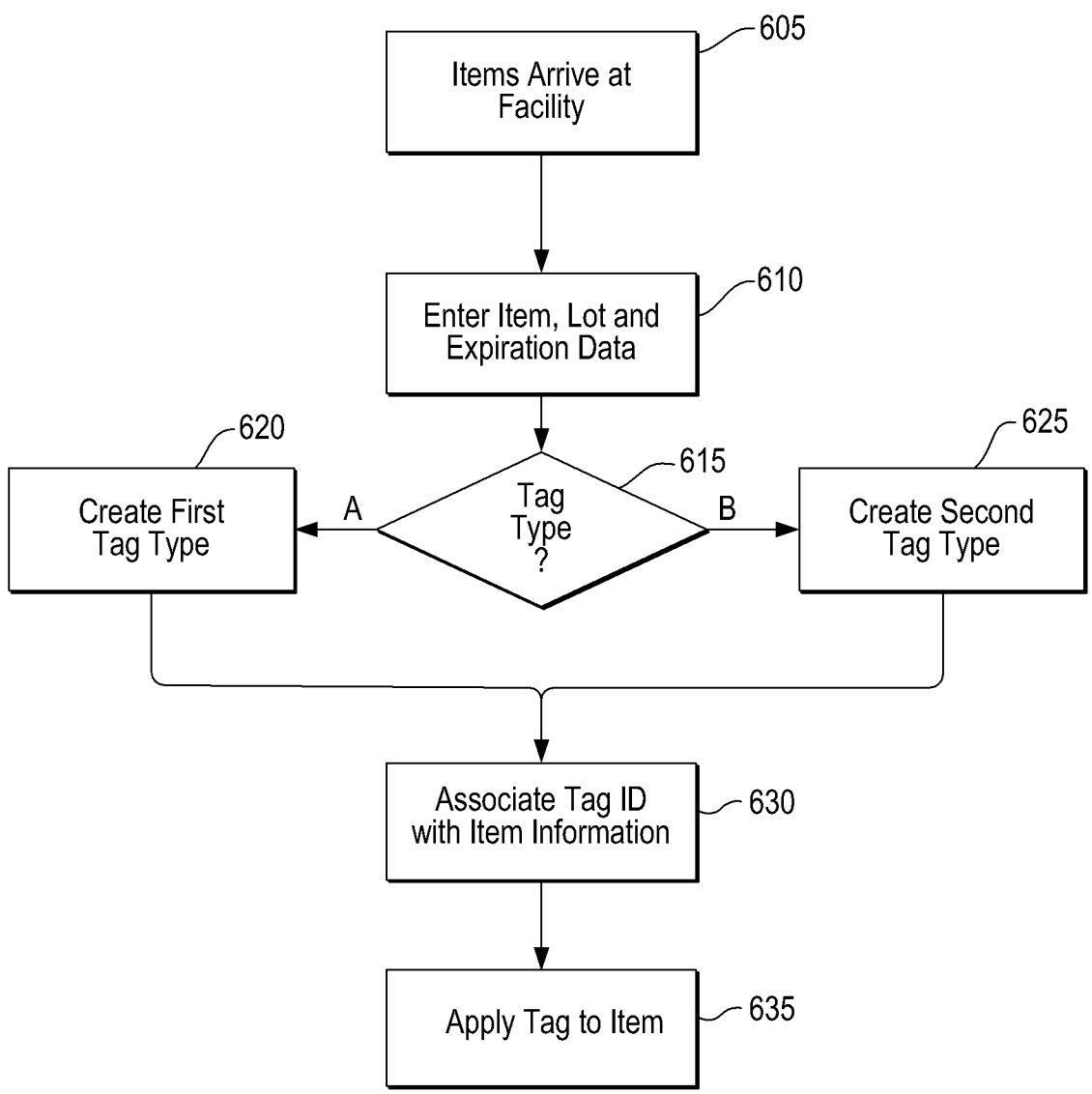
FIG. 15 is a flowchart illustrating a method of receiving and processing items for a pharmacy kit according to an embodiment of the inventive concept.

FIG. 15 is a flowchart illustrating a method of receiving and processing items for a pharmacy kit according to an embodiment of the inventive concept. The method of FIG. 15 is an example of step 505 of FIG. 14.

Referring to FIG. 15, items arrive at a facility (e.g., a hospital) from a third party manufacturer, distributor, or supplier (605). In some circumstances, the items may have RFID tags when they arrive at the facility. Accordingly, system 100 may scan the items and look up item information from the third party or an additional third party. Such information may include, for example, item master data, item lot data, and item expiration dates. If the items are not already tagged, item information may be entered into system 100 using a bar code scanner as described above, or by manual user input (610).

Based on the item information, system 100 determines whether each item requires a first type of tag (illustrated as type "A") or a second type of tag (illustrated as item type "B") (615). This determination is typically performed based on the type of the item or its packaging. For example, items having metal packaging such as metal bag, etc., may require an RFID tag having a thicker insulation layer (e.g., foam) to prevent it from experiencing EMI from the metal. Other types of items, such as glass or plastic packages, may not require such an RFID tag. Although the method of FIG. 15 shows an example using two different tag types, the described method is not limited to two tag types, and could be performed with additional tag types. Following the determination of the tag type, system 100 creates the first type of tag (620) or the second type of tag (625).

In creating the tags, system 100 may optionally perform automatic detection of whether it is attached to an RFID printer. If such an attachment is detected, it may control the RFID printer to print an RFID tag having a unique identifier for each item in the kit. Otherwise, a user may manually enter a unique tag identifier for each item into system 100. The manually entered identifiers can be determined, for example, based on the labeling of already printed RFID tags.

Next, system 100 associates the unique identifiers with the stored item information (630), allowing the item information to be retrieved subsequently when the RFID tags are scanned. Finally, the RFID tags are attached to corresponding items (635).

Figure 16:
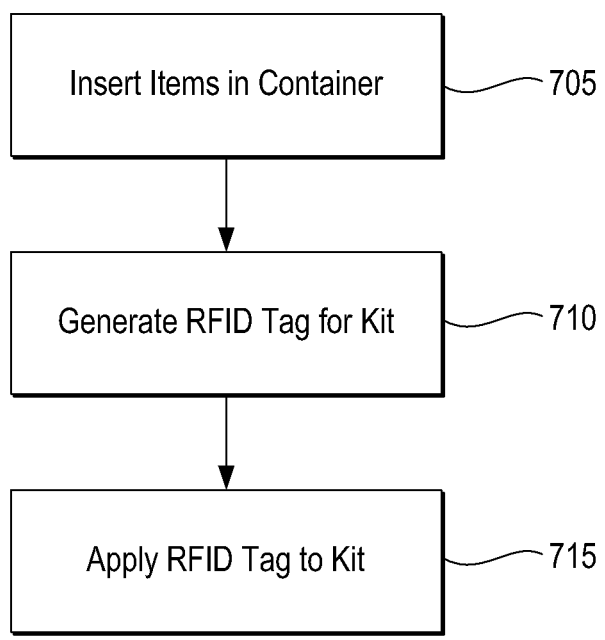
FIG. 16 is a flowchart illustrating a method of building a pharmacy kit according to an embodiment of the inventive concept.

FIG. 16 is a flowchart illustrating a method of building a pharmacy kit according to an embodiment of the inventive concept. The method of FIG. 16 is an example of step 510 of FIG. 14.

Referring to FIG. 16, the method comprises inserting tagged items into a container (705), generating an RFID tag for the kit (710), and applying the RFID tag to the kit (715). The method may further comprise sealing the kit; however, the sealing is typically performed after the kit has been scanned. Where system 100 is connected to an RFID printer, the kit's RFID tag can be generated using the printer, similar to the method of FIG. 15. Otherwise, a preprinted RFID tag can be used, and the tag's number can be manually entered into system 100 as in the method of FIG. 15. The sealing can be performed, for example, using a shrink wrap material, an adhesive, a sticker, or various other known techniques. In general, the term seal or sealing, as used herein, should not be construed in an overly formal sense—for example, it does not require an airtight seal—but rather it merely refers to a mechanism for ensuring that the contents of the kit are not tampered with as long as a seal remains in place or unbroken. Moreover, some seals used in conjunction with RFID technology may allow RFID based detection of whether a seal is broken.

Figure 17A:
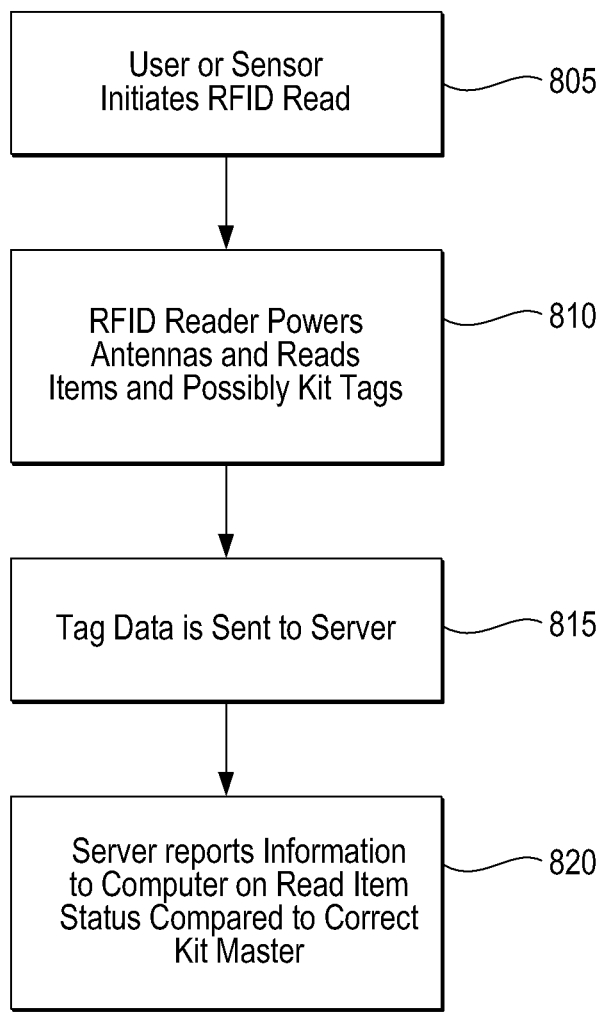
FIGS. 17A and 17B are flowcharts illustrating methods of operating the system of FIG. 1 according to an embodiment of the inventive concept.
Figure 17B:
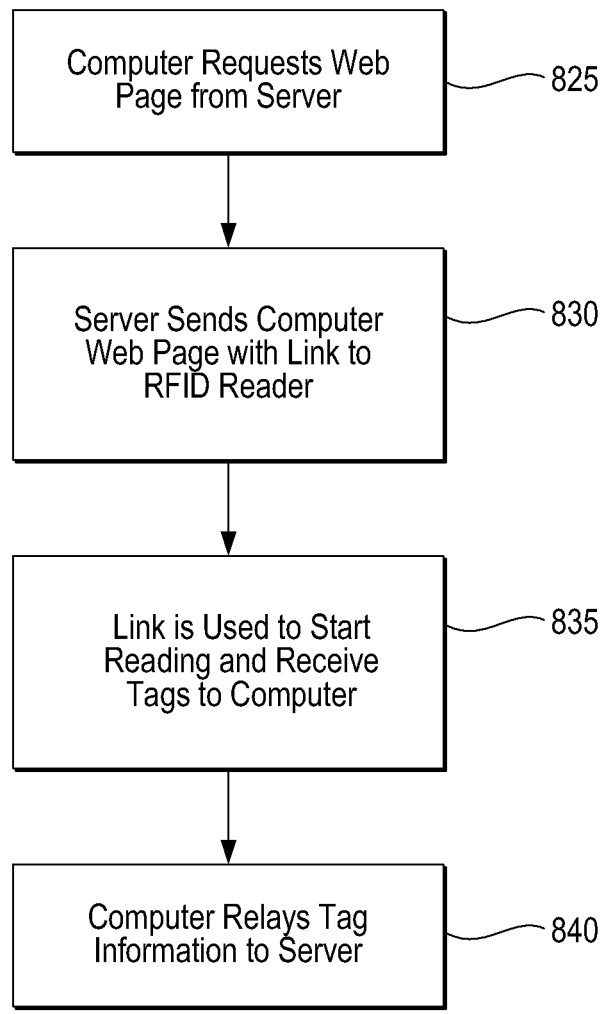

FIGS. 17A and 17B are flowcharts illustrating methods of operating kit management system 100 according to an embodiment of the inventive concept. In particular, FIG. 17A shows a method that can be used to implement step 515 of FIG. 14, and FIG. 17B shows a method that can be used to implement parts of the method of FIG. 17A.

Referring to FIG. 17A, a user or sensor initiates an RFID read operation (805). This can be accomplished, for instance, by merely placing kit 105 in RFID reading station 110, or by actuating specific controls on a user interface. In the read operation, RFID reader 305 powers antennas of RFID tags in kit 105, and it reads item tags and a kit tag, if present (810). The read operation may be used to perform an initial inventory of kit 105 following its assembly, or it can used for a re-inventory following use. Next, tag data is sent to a server in information processing system 115 or elsewhere (815). Finally, the server reports information to a user via an interface such as a computer display or a computer-generated printout (820).

Referring to FIG. 17B, steps 805 and 815 can be performed through the use of a web interface such as a web browser. For example, in some embodiments, a user directs a computer to request a web page from a server (825). This is typically accomplished through a web browser and it can be done in an encrypted or non-encrypted manner. For instance, the computer can communicate with the server using an encrypted protocol such as the secure sockets layer (SSL) protocol.

Next, the server returns instructions on how to scan which could take the form of a link allowing control of the RFID reader (830). In the example using a link, the user clicks on the link to start a read operation, and the RFID reader then captures tag information from kit 105 and transmits it to the computer (835). Finally, the computer relays the tag information to the server for validation, storage, and/or other forms of processing (840).

The server typically stores kit-related information such as master templates, item master templates, and information regarding individual kits and items, as in the example of FIG. 13. This information can be compared with the tag information relayed to the server in step 840, and then based on the comparison the server may generate a report on the status of the kit, such as whether any items are absent or whether any items have been erroneously included in the kit. The report may also include information relating to the expiration status of the items in kit 105, such as whether the items are expired or near expiration, or a summary of the expiration status of a set of items or the kit as a whole. The report may also include a charge sheet including the status of each item, such as its expiration date, which items have expired, which items are about to expire, and which item is going to expire next. In general, the information included in the report may be data that was read from a kit, item, or other source, or it may be data that was calculated based on rules, inputs, or other criteria.

Figure 18:
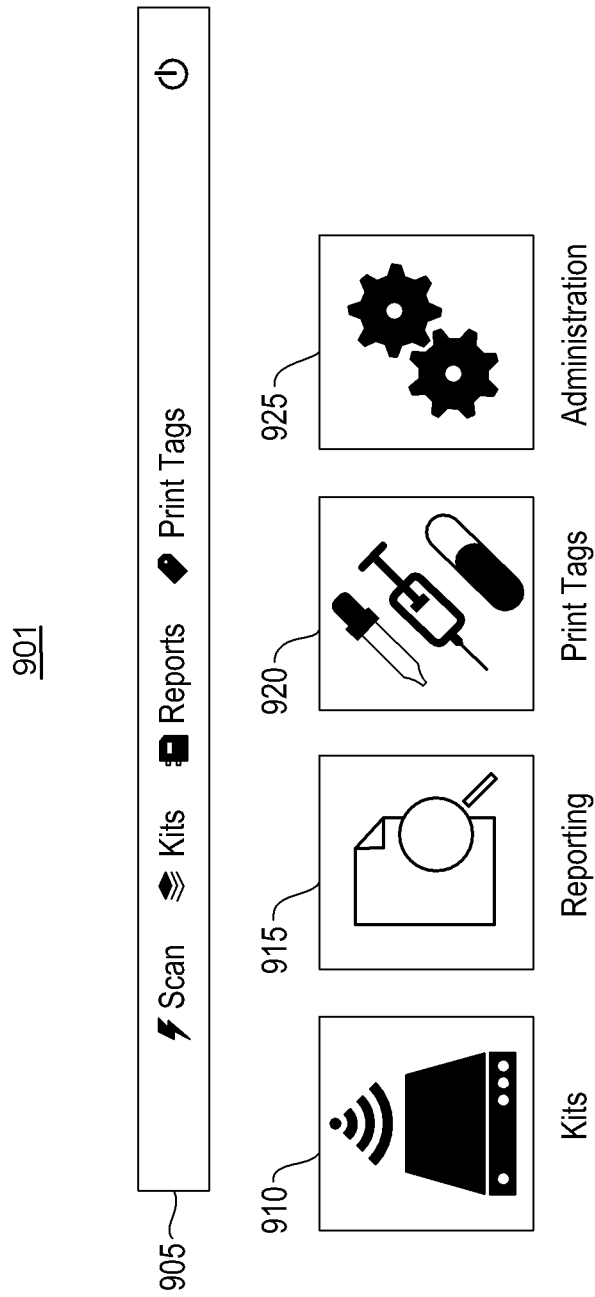
FIG. 18 shows an interface that can be used to control the system of FIG. 1 according to an embodiment of the inventive concept.

FIG. 18 shows an interface 901 that can be used to control system 100 according to an embodiment of the inventive concept. For example, interface 901 can be used to control various aspects of the methods illustrated in FIGS. 14 through 17. Interface 901 is typically accessed through a display connected to a computer or server such as those illustrated in FIG. 13.

Referring to FIG. 18, interface 901 comprises interactive graphical user interface (GUI) components including a menu bar 905 and buttons 910 through 925. These features allow a user to initiate various kit-related procedures, such as scanning a kit that has been placed in an RFID reading station, generating reports based on kit information, printing RFID tags for a kit, and performing administrative tasks. For example, a user may press button 910 (or alternatively, a scan button in menu bar 905) to initiate a read operation of RFID reading station 110 after kit 105 has been placed in a designated reading location such as a metal box. The user may press button 915 to generate a report comprising information similar to that illustrated in FIG. 11C. The user may press button 920 to initiate a procedure for capturing item information and printing RFID tags. Finally, the user may press button 925 to access various administrative controls for system 100 or interface 901.

FIG. 19 shows a report 1001 generated for a pharmacy kit using system 100 according to an embodiment of the inventive concept. Report 1001 corresponds to a pediatric emergency drug tray, which is a type of kit comprising items used for common pediatric emergencies. Such a kit can be deployed to a hospital emergency room, for example.

Referring to FIG. 19, report 1001 comprises a portion 1005 indicating the type of kit for which the report was generated, as well as the total number of items in the kit. In this example, the kit comprises 51 total items. Report 1001 further comprises a portion 1010 indicating the number of extra and missing items in the kit, as well as the number of expired or soon to expire items. In this example, one item is missing and two items are near expiration. The soon-to-expire items are listed as two containers of Procainamide Hydrochloride, which expire on Oct. 1, 2012. The date range of soon-to-expire items can be set arbitrarily, for example, using administrative tools accessible through button 925 in interface 901. Nevertheless, the date range is typically established in consideration of factors such as the anticipated delay between deployment of the kit and its use, as well as any regulatory considerations, such as rules from the board-of-pharmacy requirements or the joint commission (TJC).

Report 1001 also includes a portion 1015 indicating the date of a most recent scan, a portion 1020 showing additional details for the soon-to-expire items, and a portion 1025 showing additional details for missing items.

FIG. 20 shows another report 1100 generated for a pharmacy kit using system 100 according to an embodiment of the inventive concept. Report 1100 corresponds to a demonstration kit, which is a type of kit comprising items used for common pediatric emergencies. Such a kit can be deployed to a hospital emergency room, for example.

Report 1100 comprises a portion 1105 indicating the type of the kit and the total number of items in the kit. In this example, the kit comprises 26 total items. Report 1100 further comprises a portion 1010 indicating the number of extra and missing items in the kit, an entity to be billed for used items, and the number of expired or soon to expire items. In this example, there are two extra items, one expired item, and one soon-to-expire item. The entity to be billed is listed as KRE1981. The expired item is a box of Protopic, which is listed as having expired on Sep. 28, 2012.

Report 1100 further comprises a portion 1115 indicating the date of a most recent scan, a portion 1120 showing additional details for the expired items, a portion 1125 showing additional details for the soon-to-expire items, and a portion 1130 showing additional details for the extra items. Report 1100 still further comprises a portion 1135 indicating a current location of the kit and providing a "check out" button for assigning the kit to a specific location or person. In this example, the kit is currently assigned to the location "Central Pharmacy".

Figure 21:
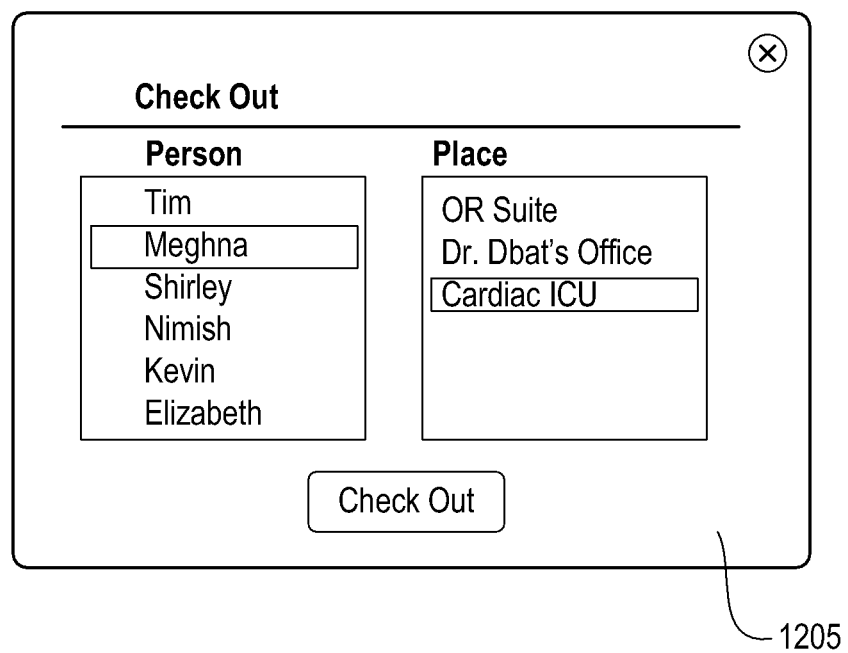
FIG. 21 shows an interface for checking out a kit to a user or location according to an embodiment of the inventive concept.

FIG. 21 shows an interface 1200 for checking out a kit to a user or location according to an embodiment of the inventive concept. Interface 1200 can be invoked, for instance, using the check out button in area 1135 of FIG. 20. In response to a user pressing the check out button, a dialog box 1205 appears within interface 1200. Dialog box 1205 allows a user to select a person or place to whom the kit may be assigned. This selection can be made, for example, as the kit is placed in possession of the selected person or an authorized delivery agent. Information regarding the selected person and location can then be stored in system 100 to facilitate subsequent recovery or further monitoring of the kit.

FIGS. 22A and 22B show interfaces 1300A and 1300B used to generate and view reports for pharmacy kits according to an embodiment of the inventive concept. In particular, FIG. 22A shows an example of an interface where a user has selected to view a report of kits that need re-working, and FIG. 22B shows an example of an interface where a user has selected to view a report of kits containing a specific lot number.

Referring to FIG. 22A, interface 1300A comprises a first area 1305A where a user selects a type of report to be generated. In this example, the user has selected from a drop down menu to generate a report of kits that need re-working. Once the selection is made the drop down menu, first area 1305A is further populated with options of details to include in the report. In this example, the options allow the user to select whether the report should include surplus items, shortages, expired items, expiring items, or all segments of the kit.

Interface 1300A further comprises a second area 1310A for displaying the report. According to the report in area 1310A, system 100 has information on two kits satisfying the specified options. In particular, a demo kit has a shortage of nasal spray, and it has a soon-to-expire container of Gentamicin Sulfate. A bandage kit has shortages of small, medium, and large bandages.

Referring to FIG. 22B, interface 1300B comprises a first area 1305B where a user selects the type of report to be generated. In this example, the user has selected from the drop down menu to generate a report of kits containing a specific item or lot number. Based on this selection, first area 1305B is populated with a form allowing the user to enter all or part of a lot number or other information for identifying the item. In the example of FIG. 22B, the user has entered a lot number.

Interface 1300B further comprises a second area 1310B for displaying the report. According to the report in area 1310B, a demo kit includes an item with the lot number specified in second area 1310A. Notably, in the example of FIG. 22B, only a partial lot number is entered first area in 1305B, so second area 1310B displays information related to items that begin with the partial lot number. However, system 100 could be modified to use the exact lot number only. It could also be modified to use multiple lot numbers.

In addition to generating reports such as those illustrated in FIGS. 19 through 13, system 100 may also generate reports on kit locations. Such locations can be determined, for example, through automatic kit tracking or some other mechanism. Moreover, system 100 may also provide mechanisms for automatically tracking inventory in the kits and the usage of items based on usage data. For example, by analyzing usage data of different items, system 100 could determine the level inventory to meet minimum requirements of all kits in a facility or a target level of inventory to be maintained. For example, if a type of kit requires a bottle of ibuprofen and the facility has 20 kits of that type, the facility has a minimum requirement of 20 bottles of ibuprofen. If the facility uses 19 bottles of ibuprofen during a specified time (e.g., a month), system 100 could then estimate or predict when the facility will run out of the current stock of ibuprofen. Accordingly, system 100 can be used to predict where inventory shortages may occur and then alert relevant personnel of potential existing or upcoming inventory shortages.

System 100 may also automatically inventory items in pharmacy kits to determine where anything is missing, extra, expired, or near expired. This can reduce the chance of manual kit stocking errors or related medical errors in a hospital or other facility. System 100 may also automatically find items for recall in the hospital or emergency medical field kits.

As indicated by the foregoing, embodiments of the inventive concept provide various systems and methods for managing pharmacy kits using multiple acceptance criteria for pharmacy kit segments. These and other embodiments may potentially improve the efficiency and accuracy of kit stocking procedures, kit verification procedures, and related reporting procedures, among other things.

The foregoing is illustrative of embodiments and is not to be construed as limiting thereof. Although a few embodiments have been described, those skilled in the art will readily appreciate that many modifications are possible in the embodiments without materially departing from the scope of the inventive concept. Accordingly, all such modifications are intended to be included within the scope of the inventive concept as defined in the claims.

The described embodiments relate generally to management of pharmacy items based on contextual attributes associated with the items. For example, in certain embodiments, one or more pharmacy items are inspected to identify one or more of their contextual attributes, and then a workflow associated with the items is executed, modified, or blocked based on the contextual attributes. As will be apparent from the following description, pharmacy items, workflows, and workflow execution, modification, or blocking can take many alternative forms.

In certain embodiments, pharmacy items are processed in several different stages before being distributed to locations inside a hospital such as smaller satellite pharmacies, dispensing stations, or pre-prepared groups of medications in kits and trays. A system as described below may halt or alter the process of advancing a kit, tray or bulk group of medications in the event that contextual attributes of the item do not meet the requirements of a rules engine evaluating the item's appropriateness for processing. For example, suppose a box of 24 vials of dopamine had been entered into inventory and tagged with radio frequency identification (RFID) tags. Where a user attempts to include one of those vials into a tray destined for use in an operating room, the system may evaluate every item in that tray and, finding that one of the vials had not been verified, stop the process of completing the tray and require an authorized user to verify the item or remove it from the tray before tray completion would be allowed.

To accomplish this, each pharmacy item may have a series of contextual attributes assigned to it, and those contextual attributes may be evaluated by the rules engine, which can be any functional apparatus capable of evaluating conditions related to the contextual attributes. Where an item is received into inventory, the system assigns it a discrete identifier in a database of all labeled items at that facility. This identifier may be programmed into an RFID tag that can be affixed to the container for the item. A database entry for that identifier may include other distinguishing information about the item, including what pharmaceutical product it represents, what lot or batch of that product it came from, a serial number, when it expires, how long it can stay unrefrigerated, what physical location it is stored in, and whether or not it has been verified by a qualified user.

The process of changing an item's status to indicate that an acceptable verification process had been followed could be accomplished in various alternative ways. For example, a batch processing option in which entire boxes or trays of unverified medications could be received into inventory through the use of a RFID scanning station that reads the discrete identifier off of each tag affixed to a medication in the reader and allows for bulk updates of the status to be made is perhaps the easiest. However, other methods of accomplishing this could include using an optical scanner or typing in the unique item identifier in order to update single items requiring status updates. In some embodiments, a first user performs an initial scan to enter an item into inventory, resulting in a verification attribute of the item being set to a status indicating it has not been verified. Thereafter, a second user who is authorized to perform verification changes the verification attribute on the item to indicate that it has been verified.

Where the system is able to distinguish between received items and verified items, a pharmacy could use computerized reporting tools to investigate the amount of received, verified, deployed and used inventory they have recorded, and manage the process of accepting new items into inventory and deploying them out to satellite pharmacy locations, patient care areas, or medications kits and trays.

As used herein, the term "pharmacy item" (or simply "item") refers to any type of item that is formally dispensed or distributed by way of a pharmacy. In a typical context, such items may include medications, medical instruments, and other materials used by medical professionals to treat patients. The more specific term "regulated pharmacy item" refers to a pharmacy item whose dispensing or distribution is governed by rules of inspection and verification, with such rules being promulgated by, e.g., a state pharmacy board or the hospital itself. In various alternative embodiments, pharmacy items may be processed individually or in groups, referred to as "pharmacy kits". For instance, inspection and verification procedures may be applied to a kit as a whole, or to individual items independent of a kit. In this context, the term "pharmacy kit" or "kit" denotes a group of items specified by a template. Examples of pharmacy kits, as well as various properties and management techniques for kits, are disclosed in U.S. patent application Ser. No. 13/554,342.

As used herein, the term "contextual attribute" refers to information that has been expressly associated with a pharmacy item or collection of items through a handling process such as labeling, data entry, scanning, tracking, or updating, for example. Contextual attributes may include, for instance, a verification status, current and/or previous item handlers, current and/or previous location(s), associated items, previous workflow steps performed in relation to the item, and so on. The value of a contextual attribute may be determined according to human and/or machine interaction with an item or items. For example, a medical professional may identify and record a contextual attribute by manually entering it into a computer, or the contextual attribute may be identified and recorded by a machine that scans a tag or label on the item. Some ways to associate a contextual attribute with an item include, for instance, linking the attribute and item together in database, or recording the attribute information in a label affixed to the item.

As used herein, the term "workflow" denotes a predetermined sequence of steps that governs the dispensing or distribution of pharmacy items. In general, it may refer to processes performed by humans, electronic systems, and/or various other forms of available equipment. For example, a workflow may comprise a pharmacist scanning a pharmacy item for verification, followed by a computer displaying and/or printing information related to the verification, and subsequent dispatching of the pharmacy item to a destination within a hospital. Typically, the ongoing execution of a workflow is controlled by way of an electronic system, such as a computer network, which may display or record information necessary to perform various processes.

A workflow may be said to be "blocked" where predetermined steps of the workflow are prevented from being performed due to contingencies in the workflow. For instance, where the workflow includes steps for verifying an item and then dispatching the item contingent upon successful verification, the dispatching and any subsequent steps may be prevented or "blocked" upon failed verification. The blocking of a workflow may be accompanied by additional steps, such as displaying a warning screen indicating that a problem has occurred during verification and providing information to fix the problem. Similarly, a workflow may be said to be "modified" where steps are added to or removed from the workflow due to contingencies in the workflow. For instance, where the workflow determines a location of an item, it may add or remove steps depending on the location. A workflow is said to be "executed" where its predetermined or modified steps are performed. In various alternative embodiments, the modification of a workflow may take the form of displaying various screens to a user. For instance, modifying a workflow may involve displaying a first screen to a user if an item is determined to be located in the pharmacy, or displaying a second screen to the user if the item is determined to be located in another location of a hospital.

Certain portions of a workflow, such as verification, may require actions to be performed by an "authorized professional". Such a professional may include, for instance, a pharmacist, a qualified technician, or some other person indicated by a relevant regulation. The regulation may include, for example, those having the force of law at a federal, state, or local level, or those stipulated by a medical facility's self imposed rules. In general, actions performed by an authorized professional may be accompanied by some form of logging to confirm such a professional's involvement. Such logging may comprise, for instance, signing a printed charge sheet or entering confirmation data for verified items.

Figure 23:
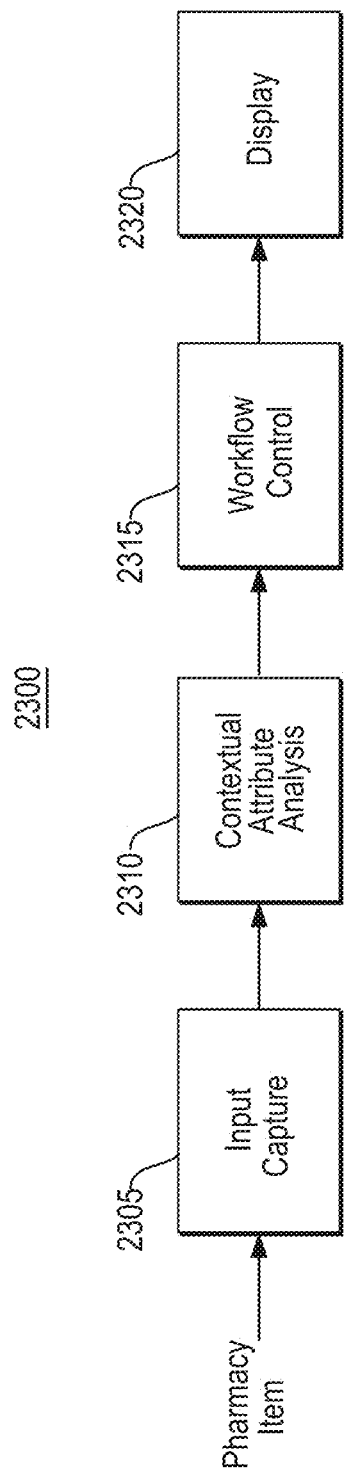
FIG. 23 is a block diagram of a system for managing pharmacy items based on contextual attributes, according to an embodiment of the inventive concept.

FIG. 23 is a block diagram of a system 2300 for managing pharmacy items based on contextual attributes, according to an embodiment of the inventive concept. System 2300 is typically implemented by a computer system and associated peripheral devices, but it can take other forms. In a typical hospital setting, multiple instances of system 2300, or portions thereof, may be located at different parts of the hospital so that pharmacy items can be managed at different checkpoints.

Referring to FIG. 23, system 2300 comprises an input capture component 2305, a contextual attribute analysis component 2310, a workflow control component 2315, and a display component 2320. Collectively, these components are designed to capture information for pharmacy items and to manage a workflow of the pharmacy items based on the captured information. Each of these components is typically implemented by a combination of hardware and software.

Input capture component 2305 typically comprises an RFID scanner or bar code scanner capable of capturing information from one or more pharmacy items. Such a device may operate automatically in response to the presence of one or more pharmacy items (e.g., by detecting and interrogating RFID tags), or it may operate in response to some form of user initiation, such as the pressing of a button, the handling of a bar code or RFID scanner, or the operation of a computer user interface. Input capture component 2305 may operate in batch mode to scan multiple items concurrently or in succession, or it may capture information for one item at a time. In addition, input capture component 2305 may comprise more than one device. For instance, it may comprise a collection of different input devices for capturing relevant information used to manage the pharmacy items.

During typical operation, a user presents one or more pharmacy items to input capture component 2305. Upon recognizing the presence of the one or more pharmacy items, input capture component 2305 receives input data identifying the one or more items and transmits the input data to contextual attribute analysis component 2310. Such input data can be, for instance, information encoded in a bar code label or RFID tag affixed to the one or more pharmacy items.

In addition to receiving the input data identifying the one or more pharmacy items, input capture component 2305 may also receive information used to update contextual attributes of the pharmacy items. For example, when a user scans an item, the user may also supply information indicating who performed the scanning, whether the item has been verified, and so on.

Contextual attribute analysis component 2310 accesses stored information corresponding to the one or more pharmacy items based on the received input data, and it determines a value of at least one contextual attribute of the one or more pharmacy items based on the accessed information. The stored information may be located in a database used by an institution to manage a collection of items. For instance, a hospital may use a central database to track pharmacy items throughout the hospital. Among other things, the contextual attribute may indicate whether labeling and contents of the one or more pharmacy items have been verified by one or more authorized pharmacy professionals, it may indicate a current or prior location of the one or more pharmacy items, or it may indicate a current or prior handler of the one or more pharmacy items. Additionally, where the one or more pharmacy items constitute a pharmacy kit, the at least one contextual attribute may correspond to the pharmacy kit as a whole, e.g., whether the kit has been verified, a location of the kit, etc.

Workflow control component 2315 selectively executes, blocks, or modifies a workflow to control distribution of the one or more pharmacy items according to the identified value of the at least one contextual attribute. Various examples of the selective execution, blocking, or modification are described below with reference to FIGS. 25 through 31.

Display component 2320 displays information related to the workflow. For example, it may display various screens indicating the values of contextual attributes, screens confirming or prompting inspection and verification of pharmacy items, screens providing warnings of failed verification, and so on. Display component 2320 may present screens for entering data related to verification or contextual attributes. Various examples of information to be displayed on display component 2320 are illustrated in FIGS. 27 through 31. In addition to display component 2320, system 2300 may provide other forms of output, such a printed charge sheet produced upon successful validation of one or more pharmacy items, or audio feedback such as alerts in the workflow.

Figure 24:
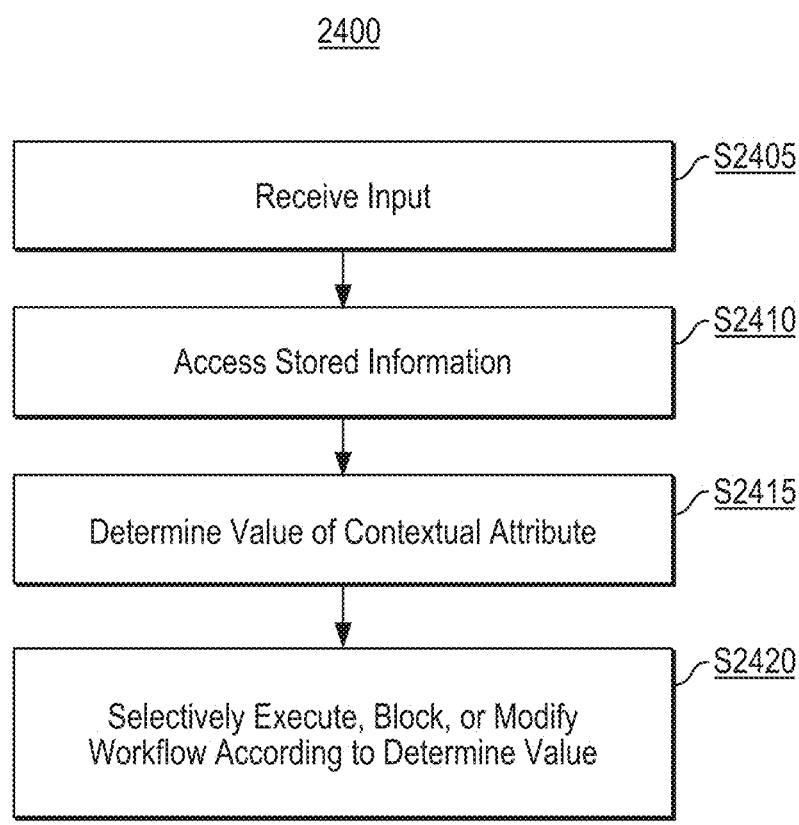
FIG. 24 is a flowchart illustrating a method of managing pharmacy items based on contextual attributes, according to an embodiment of the inventive concept.

FIG. 24 is a flowchart illustrating a method 2400 of managing pharmacy items based on contextual attributes, according to an embodiment of the inventive concept. The method of FIG. 24 could be performed by system 2300, for instance, although it is not limited to this or any other particular system implementation.

Referring to FIG. 24, the method comprises receiving an input identifying one or more pharmacy items (S2405). As indicated above, such an input may be received through an automated or quasi-automated process such as bar code scanning or RFID scanning. It can also be received through manual user input.

The method further comprises accessing stored information corresponding to the one or more pharmacy items based on the received input (S2410), and determining a value of at least one contextual attribute of the one or more pharmacy items based on the accessed information (S2415). These steps may be performed, for instance, by accessing a database containing values of contextual attributes for a large collection of items that have been registered with a system or institution. It may also involve analysis of information encoded in a bar code or RFID tag.

Finally, the method comprises selectively executing, blocking, or modifying a workflow to control distribution of the one or more pharmacy items according to the value of the at least one contextual attribute (S2420). As one example of this step, if the at least one contextual attribute indicates that a drug is expired or recalled, the method may block a user from performing a subsequent step of a workflow and/or display a warning. As another example, if the at least one contextual attribute indicates that a drug has already been used on a patient, the method may display information indicating the presence of a new patient and it may therefore prevent a user administering the drug to the new patient. As yet another example, if the at least one contextual attribute indicates that a drug is considered to be a substitute for another drug or has "abnormal strength", the method may allow a user to continue a workflow but may also display a warning indicating this is a change from normal procedure.

As still another example, if the at least one contextual attribute indicates that an item (e.g., a drug) has undergone secondary preparation within a pharmacy (e.g., mixing of a powder with a liquid or loading of a medication into a syringe), the method may allow a user to perform certain workflow functions that are only available on drugs with secondary preparation, or it may prevent the user from performing certain workflow functions that are available on drugs other than those with secondary preparation. In general, the term "secondary preparation" refers to any process that changes the state of an item as originally provided to a pharmacy into a different state to be used on a patient. In one example, suppose a drug and syringe have undergone secondary preparation by a process of loading the drug into the syringe. Under these circumstances, the method may inspect an item attribute (of the drug and/or the syringe) to determine that the drug is loaded into the syringe, and it may further inspect another item attribute to determine how long ago the drug was loaded into the syringe. If the syringe was prepared too long ago, the method may modify the workflow to prevent the syringe from being used on a patient. Still other examples of workflow variations corresponding to step S2420 are described below with reference to FIGS. 25 through 31.

Figure 25:
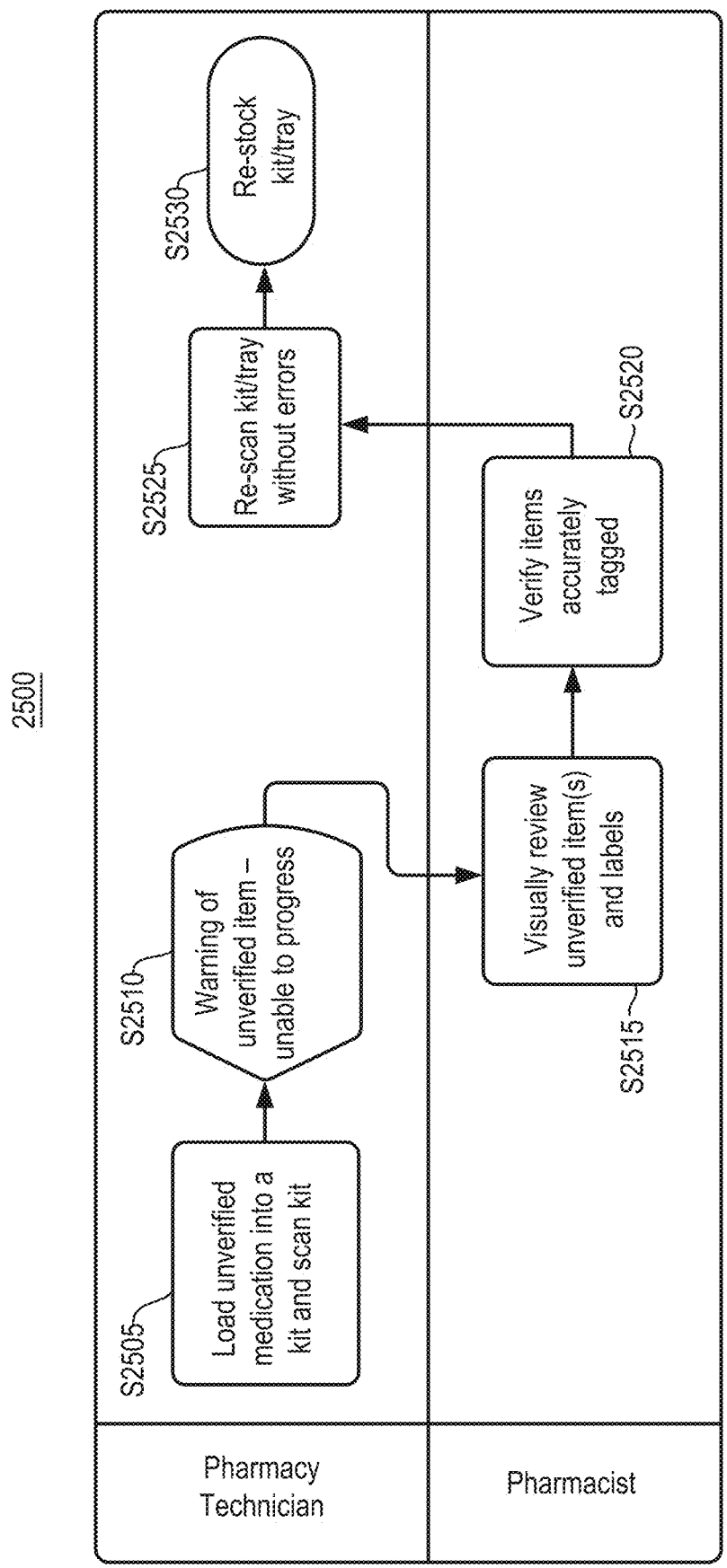
FIG. 25 is a workflow diagram illustrating a method of blocking the distribution of a pharmacy kit containing unverified items, according to an embodiment of the inventive concept.

FIG. 25 is a workflow diagram illustrating a method 2500 of blocking the distribution of a pharmacy kit containing unverified items, according to an embodiment of the inventive concept. In the method of FIG. 25, certain steps are performed through actions by a pharmacy technician and certain steps are performed through actions by a pharmacist. Alternatively, however, the steps could be performed by two different technicians, two different pharmacists, or two other types of pharmacy professionals, as provided by relevant laws, regulations, and/or institutional policies.

Referring to FIG. 25, the method begins with the pharmacy technician loading unverified pharmacy items (e.g., medications) into a kit and scanning the kit (S2505). This loading step typically occurs within a hospital pharmacy as part of an inventory stocking process, and the scanning typically involves applying a bar code scanner or RFID scanner to packaging or labeling materials affixed to items in the kit. In general, the scanning process may capture information associated with individual pharmacy items, as well as the kit in general. It may also store the information in a database, e.g., within system 22500. This information can include, e.g., descriptive attributes (e.g., National Drug Codes (NDCs) or Universal Product Codes (UPCs)) and contextual attributes, such as verification status, current or prior location, current or prior handler, lot number, and expiration date, and so on.

In the illustrated example, the scanning process is used to determine whether the items and/or kit have been verified by an authorized professional. This can be accomplished by comparing the captured information with previously stored information, such as one or more contextual attributes associated with the items and/or kit. Upon successful verification, the items and/or kit may be deployed to a location within a hospital or other facility. Upon failed verification, a warning is displayed on a screen to indicate the failure, and the user is advised that the distribution of the items cannot proceed (S2510). In other words, the workflow is blocked.

Following the warning, a pharmacist may visually review unverified items and labels among those that were previously scanned (S2515). This review process may be used to confirm that the items have the correct contents and labeling. The review process is deemed successful if the pharmacist is able to provide positive confirmation of the items as presented, or to fix any deficiencies that exist. In addition to inspecting the items themselves, the pharmacist may also compare the items with information stored in a computer system. For instance, the pharmacist may inspect a displayed list of recorded items and compare the list to the items actually presented.

Next, assuming a successful review process, the pharmacist provides formal verification that the items and/or kit have correct contents and labeling (S2520). This formal verification may involve, for instance, entering data in a computer system or signing papers. Typically, such verification will indicate the pharmacist's identity, as well as the circumstances of the verification, such as time, date, location, methodology, etc.

Following verification, the technician may re-scan and deploy the kit for use in the hospital or other facility (S2525). Because the kit has been verified at this point, the scanning does not produce an error or warning, and the workflow is not blocked. Finally, following use of the kit, it can be re-stocked by the technician (S2530). The restocking generally introduces unverified items into the kit, so it may result in a return to step S2505.

Figure 26:
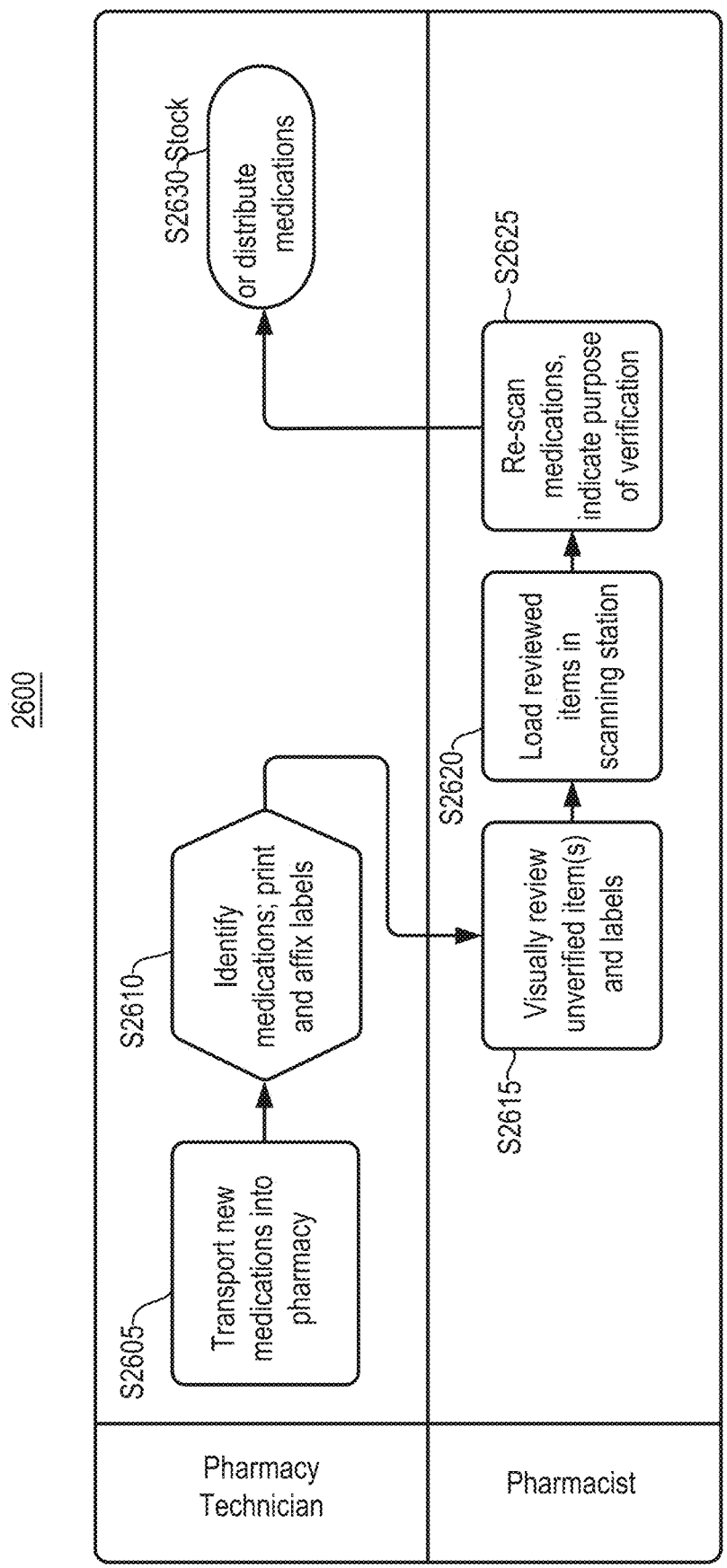
FIG. 26 is a workflow diagram illustrating a method of verifying multiple pharmacy items in batch mode, according to an embodiment of the inventive concept.

FIG. 26 is a workflow diagram illustrating a method of verifying multiple pharmacy items in batch mode, according to an embodiment of the inventive concept. This method is similar to that of FIG. 25 in that certain steps are performed by a technician while others are performed by a pharmacist. It differs from the method of FIG. 25 in that it involves the preparation and verification of individual items rather than kits.

Referring to FIG. 26, the technician transports or receives new items (e.g., medications) into a pharmacy (S2605), and then identifies and labels the items (S2610). The identification and labeling may involve automated processes, such as scanning existing barcode labels and/or printing and affixing RFID labels, although such processes are generally supervised by the technician to ensure accuracy. In this regard, step S2610 can be considered a first step of a two-step verification process, i.e., a process involving two different professionals. Additionally, the scanning and labeling is typically accompanied by operations for storing relevant information in a computer system. For instance, when an item is identified by scanning, the scanned information may be added to a database of inventory. The database may also store known contextual attributes associated with the scanned item.

Next, the pharmacist visually reviews the items and corresponding labels to confirm their accuracy (S2615). This step is similar to step S2515 of FIG. 25, and it may likewise require the pharmacist to address any inaccuracies that are found in the course of review. Upon successful review, the items are loaded into a scanning station, e.g., an RFID scanning station (S2620) and then re-scanned (S2625). Collectively, steps S2615 through S2625 constitute a second step of the two-step verification process. Prior to this second step, the items are considered to be unverified because they have not completed the two-step verification process.

When performing the re-scanning in step S2625, the pharmacist may provide input to a computer system to indicate that the re-scanned items have been formally verified for accuracy. Such input may be provided, for instance, through a user interface having a functional relationship with the scanning process. Additional inputs may be similarly provided to the computer system at various steps of the illustrated method to indicate other contextual attributes of the items being handled or otherwise processed. For instance, inputs may be provided to indicate who is handling the items, where the handling is being performed, and so on.

After the items have been verified by the two-step verification process, those items may be added to pharmacy stock or distributed within a hospital or other facility (S2630).

FIG. 27 shows a display interface 2700 confirming verification of a pharmacy item, according to an embodiment of the inventive concept. This interface provides examples of information that may be presented, captured, or otherwise used in the method of FIG. 227 or FIG. 26. For example, the display interface of FIG. 27 could be presented after re-scanning is performed in step S2525 or S2625 of FIG. 25 or 26, respectively.

Referring to FIG. 27, display interface 2700 contains the following general information for a pharmacy item that has been verified: the item's name, NDC, and lot number. It also shows values for the following contextual attributes associated with the item: expiration date, verification status, verifying party ("Verified By"), verification method, and verification location ("Verified At"). As indicated by the "Verification Status" attribute, the item is "Verified". Accordingly, the interface may be presented as part of process in which workflow is not blocked.

The attribute values shown in FIG. 27 are typically populated through manual data entry or by an automated process such as item scanning. These values can be entered, for instance, by a technician when preparing items in step S2505 or S2610, and they can be reviewed or updated, for instance, by a pharmacist when performing verification in step S2515 or S2615.

FIG. 28 shows a display interface 2800 allowing input to verify a pharmacy item, according to an embodiment of the inventive concept. This interface can be presented to a user for manual and/or automated data entry, e.g., in step S2505 or S2610.

Referring to FIG. 28, display interface 2800 contains the item name and shows contextual attributes, similar to display interface 2700, but it is missing the item's NDC and values for the contextual attributes. As indicated above, the missing information can be entered into provided fields either by manual or automated data entry, e.g., in steps S2505 or S2610. Basic instructions for entering the missing information are shown in display interface 2800. Once the missing information is entered into the fields, an authorized professional may verify the pharmacy item by pressing a button labeled "Verify". This button may be pressed, for instance, by a pharmacist when performing verification in step S2515 or S2615. Doing so would change the value of the "Verification Status" attribute from "Unverified" to "Verified".

FIG. 29 shows a display interface 2900 allowing input to verify multiple pharmacy items in batch mode, according to an embodiment of the inventive concept. Display interface 2900 is similar to display interface 2800, except that it contains instructions for multiple items rather than a single item, and it also allows a user to enter a quantity of an item.

FIG. 30 shows a display interface 3000 with information used to verify a pharmacy item, according to an embodiment of the inventive concept. Display interface 3000 is the same as display interface 2800, except that a user has entered an NDC, lot number, and expiration date for an item yet to be verified.

FIG. 31 shows a display interface 3100 providing a warning that a scanned pharmacy kit contains unverified items, according to an embodiment of the inventive concept. This interface can be presented to a user when a workflow is blocked due to the presence of unverified items. For example, it could be presented to a user in step S2510.

Referring to FIG. 31, display interface 3100 includes a warning that a kit contains certain unverified items. It identifies those items by name as well as identifying numbers, and it provides instructions for verifying those items. Such verification could be performed through display interface 2800, for example.

As indicated by the foregoing, pharmacy inventory management often requires multiple individuals reviewing and verifying an item is correctly tagged before it can be safely and accurately incorporated into the supply chain. The described embodiments provide systems and methods to guide users towards the appropriate tools to manage incompletely documented pharmaceutical products and to bar users from including medications that have not been verified as being accurately labeled from being deployed outside of the pharmacy where they could cause harm or waste. By using these and other embodiments, a hospital pharmacy may allow medications to be deployed with relative safety and accuracy throughout the hospital.

The foregoing is illustrative of various embodiments and is not to be construed as limiting the inventive concept. Although a few embodiments have been described, those skilled in the art will readily appreciate that many modifications are possible in the embodiments without materially departing from the novel teachings and advantages of the inventive concept. Accordingly, all such modifications are intended to be included within the scope of the inventive concept as defined in the claims.

What is claimed is:

1. A method for associating a plurality of pharmacy items with an identical pharmacy item attribute, the method comprising:
    causing an antenna coupled to an enclosure to emit a radio signal at least within the enclosure;
    receiving, in response to the antenna emitting the radio signal, a plurality of unique identifiers corresponding to a plurality of radio frequency identification (RFID) tags located within the enclosure, the plurality of RFID tags coupled to a plurality of pharmacy item containers configured to store different groups of the same pharmacy item,
    wherein a particular RFID tag of the plurality of RFID tags is coupled to a particular pharmacy item container of the plurality of pharmacy item containers and the particular pharmacy item container is configured to store one group of the different groups of the same pharmacy item, and
    wherein a particular unique identifier of the plurality of unique identifiers uniquely identifies the particular RFID tag from other RFID tags of the plurality of RFID tags; and
    in response to said receiving the plurality of unique identifiers corresponding to the plurality of RFID tags located within the enclosure, creating multiple associations between an identical pharmacy item attribute and the plurality of unique identifiers in a database such that each of the plurality of unique identifiers is associated with the identical pharmacy item attribute in the database.

2. The method of claim 1, wherein the particular RFID tag comprises an adhesive portion for affixing the particular RFID tag to the particular pharmacy item container, wherein the adhesive portion is formed of a transparent material that enables visualization of label information of the particular pharmacy item container when the adhesive portion is located on top of the label information.

3. The method of claim 1, wherein said creating the association between the identical pharmacy item attribute and each of the plurality of unique identifiers in the database comprises:
identifying entries of the database based at least in part on the plurality of unique identifiers; and
updating at least some of the identified entries to include the identical pharmacy item attribute or an indication of the identical pharmacy item attribute.

4. The method of claim 1, wherein the identical pharmacy item attribute comprises one or more of a drug name, an expiration date, an NDC number, or a lot number.

5. The method of claim 1, further comprising receiving user input comprising an indication of the identical pharmacy item attribute.

6. The method of claim 1, further comprising causing a display to display results of said creating the multiple associations.

7. A system for associating a plurality of pharmacy items with an identical pharmacy item attribute, the system comprising:
a reading station comprising an enclosure and an antenna; and
one or more processors in communication with the reading station and configured to:
cause the antenna to emit a radio signal at least within the enclosure,
receive, in response to the antenna emitting the radio signal, a plurality of unique identifiers corresponding to a plurality of radio frequency identification (RFID) tags located within the enclosure, the plurality of RFID tags coupled to a plurality of pharmacy item containers configured to store different groups of the same pharmacy item,
wherein a particular RFID tag of the plurality of RFID tags is coupled to a particular pharmacy item container of the plurality of pharmacy item containers and the particular pharmacy item container is configured to store one group of the different groups of the same pharmacy item, and
wherein a particular unique identifier of the plurality of unique identifiers uniquely identifies the particular RFID tag from other RFID tags of the plurality of RFID tags, and
in response to receiving the plurality of unique identifiers corresponding to the plurality of RFID tags located within the enclosure, create multiple associations between an identical pharmacy item attribute and the plurality of unique identifiers in a database such that each of the plurality of unique identifiers is associated with the identical pharmacy item attribute in the database.

8. The system of claim 7, wherein the particular RFID tag comprises an adhesive portion for affixing the particular RFID tag to the particular pharmacy item container, wherein the adhesive portion is formed of a transparent material that enables visualization of label information of the particular pharmacy item container when the adhesive portion is located on top of the label information.

9. The system of claim 7, wherein to create the multiple associations between the pharmacy item attribute and the plurality of unique identifiers in the database the one or more processors are further configured to:
identify entries of the database based at least in part on the plurality of unique identifiers; and
update at least some of the identified entries to include the identical pharmacy item attribute or an indication of the identical pharmacy item attribute.

10. The system of claim 7, wherein the identical pharmacy item attribute comprises one or more of a drug name, an expiration date, an NDC number, or a lot number.

11. The system of claim 7, wherein the one or more processors are further configured to receive user input comprising an indication of the identical pharmacy item attribute.

12. The system of claim 7, wherein the one or more processors are further configured to cause a display to display results of the multiple associations.

13. A non-transitory computer-readable storage medium storing computer-executable instructions that when executed by one or more processors cause the one or more processors to:
cause an antenna coupled to an enclosure to emit a radio signal at least within the enclosure;
receive, in response to the antenna emitting the radio signal, a plurality of unique identifiers corresponding to a plurality of radio frequency identification (RFID) tags located within the enclosure, the plurality of RFID tags coupled to a plurality of pharmacy item containers configured to store different groups of the same pharmacy item,
wherein a particular RFID tag of the plurality of RFID tags is coupled to a particular pharmacy item container of the plurality of pharmacy item containers and the particular pharmacy item container is configured to store one group of the different groups of the same pharmacy item, and
wherein a particular unique identifier of the plurality of unique identifiers uniquely identifies the particular RFID tag from other RFID tags of the plurality of RFID tags; and
in response to receiving the plurality of unique identifiers corresponding to the plurality of RFID tags located within the enclosure, create multiple associations between an identical pharmacy item attribute and the plurality of unique identifiers in a database such that each of the plurality of unique identifiers is associated with the identical pharmacy item attribute in the database.

14. The non-transitory computer-readable storage medium of claim 13, wherein the particular RFID tag comprises an adhesive portion for affixing the particular RFID tag to the particular pharmacy item container, wherein the adhesive portion is formed of a transparent material that enables visualization of label information of the particular pharmacy item container when the adhesive portion is located on top of the label information.

15. The non-transitory computer-readable storage medium of claim 13, wherein to create the multiple associations between the identical pharmacy item attribute and the plurality of unique identifiers in the database, the computer-executable instructions, when executed, further cause the one or more processors to:
identify entries of the database based at least in part on the plurality of unique identifiers; and
update at least some of the identified entries to include the identical pharmacy item attribute or an indication of the identical pharmacy item attribute.

16. The non-transitory computer-readable storage medium of claim 13, wherein the identical pharmacy item attribute comprises one or more of a drug name, an expiration date, an NDC number, or a lot number.

17. The non-transitory computer-readable storage medium of claim 13, wherein the computer-executable instructions, when executed, further cause the one or more processors to receive user input comprising an indication of the identical pharmacy item attribute.

18. The non-transitory computer-readable storage medium of claim 13, wherein the computer-executable instructions, when executed, further cause the one or more processors to cause a display to display results of the multiple associations.

* * * * *